(12) United States Patent
Wardell et al.

(10) Patent No.: US 11,779,552 B2
(45) Date of Patent: *Oct. 10, 2023

(54) METHOD OF TREATING CANCER USING SELECTIVE ESTROGEN RECEPTOR MODULATORS

(71) Applicant: Duke University, Durham, NC (US)

(72) Inventors: Suzanne E. Wardell, Durham, NC (US); Erik R. Nelson, Champaign, IL (US); Donald P McDonnell, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/558,731

(22) Filed: Dec. 22, 2021

(65) Prior Publication Data

US 2022/0110893 A1 Apr. 14, 2022

Related U.S. Application Data

(63) Continuation of application No. 16/549,828, filed on Aug. 23, 2019, now abandoned, which is a continuation of application No. 15/129,197, filed as application No. PCT/US2015/023216 on Mar. 28, 2015, now Pat. No. 10,420,734, which is a continuation-in-part of application No. 14/512,061, filed on Oct. 10, 2014, now Pat. No. 9,421,264.

(60) Provisional application No. 62/129,379, filed on Mar. 6, 2015, provisional application No. 61/971,627, filed on Mar. 28, 2014.

(51) Int. Cl.
| | |
|---|---|
| *A61K 31/137* | (2006.01) |
| *A61K 9/00* | (2006.01) |
| *A61K 31/136* | (2006.01) |
| *A61K 31/138* | (2006.01) |
| *A61K 31/40* | (2006.01) |
| *A61K 31/4196* | (2006.01) |
| *A61K 31/4535* | (2006.01) |
| *A61K 31/565* | (2006.01) |
| *A61K 31/5685* | (2006.01) |
| *A61K 45/06* | (2006.01) |
| *C07C 217/78* | (2006.01) |
| *C07C 217/84* | (2006.01) |

(52) U.S. Cl.
CPC .......... *A61K 31/137* (2013.01); *A61K 9/0019* (2013.01); *A61K 31/136* (2013.01); *A61K 31/138* (2013.01); *A61K 31/40* (2013.01); *A61K 31/4196* (2013.01); *A61K 31/4535* (2013.01); *A61K 31/565* (2013.01); *A61K 31/5685* (2013.01); *A61K 45/06* (2013.01); *C07C 217/78* (2013.01); *C07C 217/84* (2013.01); *A61K 2121/00* (2013.01)

(58) Field of Classification Search
CPC .............. A61K 2121/00; A61K 31/136; A61K 31/137; A61K 31/138; A61K 31/40; A61K 31/4196; A61K 31/4535; A61K 31/565; A61K 31/5685; A61K 45/06; A61K 9/0019; A61P 35/00; A61P 35/04; C07C 217/78; C07C 217/84
See application file for complete search history.

(56) References Cited

U.S. PATENT DOCUMENTS

| | | |
|---|---|---|
| 3,274,213 A | 9/1966 | Lednicer |
| 4,133,814 A | 1/1979 | Jones et al. |
| 4,418,068 A | 11/1983 | Jones |
| 5,567,233 A | 10/1996 | Beck et al. |
| 5,681,835 A | 10/1997 | Willson |
| 6,204,286 B1 | 3/2001 | Cameron et al. |
| 6,410,516 B1 | 6/2002 | Baltimore et al. |
| 7,612,114 B2 | 11/2009 | Hamaoka et al. |
| 7,960,412 B2 | 6/2011 | Hamaoka et al. |
| 8,399,520 B2 | 3/2013 | Hamaoka et al. |
| 8,592,452 B2 | 11/2013 | Yamamoto et al. |
| 8,933,130 B2 | 1/2015 | Lyttle et al. |
| 9,421,264 B2 | 8/2016 | Wardell et al. |
| 10,071,066 B2 | 9/2018 | Wardell et al. |
| 10,420,734 B2 | 9/2019 | Wardell et al. |
| 2003/0065008 A1 | 4/2003 | Labrie |
| 2003/0143276 A1 | 7/2003 | Hsia et al. |
| 2004/0210080 A1 | 10/2004 | Meng et al. |
| 2006/0116364 A1 | 6/2006 | Hamaoka et al. |
| 2007/0155664 A1 | 7/2007 | Ranklove et al. |
| 2007/0213543 A1 | 9/2007 | Rodriguez |
| 2008/0114048 A1 | 5/2008 | Sui et al. |

(Continued)

FOREIGN PATENT DOCUMENTS

| | | |
|---|---|---|
| DE | 2909754 A1 | 9/1980 |
| EP | 0226508 A1 | 6/1987 |

(Continued)

OTHER PUBLICATIONS

Wardell et al., "Evaluation of the pharmacological activities of RAD1901, a selective estrogen receptor degrader," Endocrinology Related Cancer, 2015, 22(5): 713-724.

(Continued)

*Primary Examiner* — Kara R McMillian
(74) *Attorney, Agent, or Firm* — Michael Best & Friedrich LLP

(57) ABSTRACT

Disclosed herein are methods of treating subjects suffering from estrogen receptor positive cancer of the brain by administering a selective estrogen receptor degrader (SERM). Also disclosed are methods of treating a cancer that is resistant to an estrogen receptor modulator by administering a SERM.

14 Claims, 13 Drawing Sheets

(9 of 13 Drawing Sheet(s) Filed in Color)

(56) References Cited

U.S. PATENT DOCUMENTS

| | | |
|---|---|---|
| 2009/0325930 A1 | 12/2009 | Hamaoka et al. |
| 2010/0105733 A1 | 4/2010 | Lyttle et al. |
| 2010/0152236 A1 | 6/2010 | Yamamoto et al. |
| 2011/0009387 A1 | 1/2011 | Basso-Porcaro |
| 2011/0124617 A1 | 5/2011 | Lyttle et al. |
| 2013/0053448 A1 | 2/2013 | O'Dea et al. |
| 2015/0231134 A1 | 8/2015 | Erichsen |
| 2015/0274640 A1 | 10/2015 | Wardell et al. |
| 2019/0083421 A1 | 3/2019 | Wardell et al. |
| 2020/0009084 A1 | 1/2020 | Wardell et al. |
| 2020/0368184 A1 | 11/2020 | Wardell et al. |

FOREIGN PATENT DOCUMENTS

| | | |
|---|---|---|
| EP | 0406734 A2 | 1/1991 |
| EP | 0580459 A1 | 1/1991 |
| EP | 0802183 A1 | 10/1997 |
| EP | 0916652 A1 | 5/1999 |
| EP | 1199069 A2 | 4/2002 |
| EP | 1911743 A1 | 4/2008 |
| GB | 1547758 A | 6/1975 |
| GB | 2460672 A | 12/2009 |
| JP | H0324069 A | 2/1991 |
| JP | 6016957 B2 | 10/2016 |
| WO | WO 1994/027989 A1 | 12/1994 |
| WO | WO 1996/041793 A1 | 12/1996 |
| WO | WO 1997/049709 A1 | 12/1997 |
| WO | WO 2001/032631 A2 | 5/2001 |
| WO | WO 2001/049673 A2 | 7/2001 |
| WO | WO 2002/016310 A1 | 2/2002 |
| WO | WO 2002/016316 A1 | 2/2002 |
| WO | WO 2003/011824 A1 | 2/2003 |
| WO | WO 2003/063859 A1 | 8/2003 |
| WO | WO 2003/068217 A1 | 8/2003 |
| WO | WO 2003/091239 A1 | 11/2003 |
| WO | WO 2003/096980 A2 | 11/2003 |
| WO | WO 2003/099292 A1 | 12/2003 |
| WO | WO 2004/041277 A1 | 5/2004 |
| WO | WO 2004/041782 A1 | 5/2004 |
| WO | WO 2004/045518 A2 | 6/2004 |
| WO | WO 2004/058682 A1 | 7/2004 |
| WO | WO 2004/080377 A2 | 9/2004 |
| WO | WO 2004/110978 A2 | 12/2004 |
| WO | WO 2005/000309 A2 | 1/2005 |
| WO | WO 2005/000794 A1 | 1/2005 |
| WO | WO 2005/000795 A2 | 1/2005 |
| WO | WO 2005/040136 A1 | 5/2005 |
| WO | WO 2005/042464 A1 | 5/2005 |
| WO | WO 2005/049574 A1 | 6/2005 |
| WO | WO 2005/049580 A1 | 6/2005 |
| WO | WO 2005/060956 A1 | 7/2005 |
| WO | WO 2005/073204 A1 | 8/2005 |
| WO | WO 2005/077925 A1 | 8/2005 |
| WO | WO 2005/085185 A1 | 9/2005 |
| WO | WO 2005/086735 A2 | 9/2005 |
| WO | WO 2005/087232 A1 | 9/2005 |
| WO | WO 2005/089118 A2 | 9/2005 |
| WO | WO 2005/090282 A1 | 9/2005 |
| WO | WO 2005/094810 A2 | 10/2005 |
| WO | WO 2005/099707 A1 | 10/2005 |
| WO | WO 2005/102998 A1 | 11/2005 |
| WO | WO 2005/108351 A1 | 11/2005 |
| WO | WO 2005/111028 A1 | 11/2005 |
| WO | WO 2006/039243 A1 | 4/2006 |
| WO | WO 2006/044359 A2 | 4/2006 |
| WO | WO 2006/044707 A1 | 4/2006 |
| WO | WO 2006/055184 A2 | 5/2006 |
| WO | WO 2006/060108 A1 | 6/2006 |
| WO | WO 2006/076317 A2 | 7/2006 |
| WO | WO 2006/113552 A2 | 10/2006 |
| WO | WO 2006/124447 A2 | 11/2006 |
| WO | WO 2006/133216 A2 | 12/2006 |
| WO | WO 2007/002181 A2 | 1/2007 |
| WO | WO 2007/005887 A2 | 1/2007 |
| WO | WO 2007/015567 A1 | 2/2007 |
| WO | WO 2007/034846 A1 | 3/2007 |
| WO | WO 2007/067490 A1 | 6/2007 |
| WO | WO 2007/087518 A2 | 8/2007 |
| WO | WO 2007/099200 A1 | 9/2007 |
| WO | WO 2007/146914 A1 | 12/2007 |
| WO | WO 2008/002490 A2 | 1/2008 |
| WO | WO 2008/008433 A2 | 1/2008 |
| WO | WO 2008/011072 A2 | 1/2008 |
| WO | WO 2008/011073 A2 | 1/2008 |
| WO | WO 2008/024456 A2 | 2/2008 |
| WO | WO 2008/042571 A2 | 4/2008 |
| WO | WO 2008/044033 A1 | 4/2008 |
| WO | WO 2008/063867 A2 | 5/2008 |
| WO | WO 2008/121602 A1 | 10/2008 |
| WO | WO 2008/124000 A2 | 10/2008 |
| WO | WO 2008/124922 A1 | 10/2008 |
| WO | WO 2008/127717 A1 | 10/2008 |
| WO | WO 2008/128100 A1 | 10/2008 |
| WO | WO 2009/002034 A2 | 12/2008 |
| WO | WO 2009/020234 A2 | 2/2009 |
| WO | WO 2009/082437 A2 | 7/2009 |
| WO | WO 2009/105214 A2 | 8/2009 |
| WO | WO 2009/133861 A1 | 11/2009 |
| WO | WO 2009/137104 A1 | 11/2009 |
| WO | WO 2009/140448 A1 | 11/2009 |
| WO | WO 2010/118287 A1 | 10/2010 |
| WO | WO 2011/097496 A1 | 8/2011 |
| WO | WO 2011/143469 A1 | 11/2011 |
| WO | WO 2012/047617 A1 | 4/2012 |
| WO | WO 2014/085318 A1 | 6/2014 |
| WO | WO 2014/203129 A1 | 12/2014 |
| WO | WO 2016/176664 A1 | 11/2016 |
| WO | WO 2016/176665 A1 | 11/2016 |
| WO | WO 2016/176666 A1 | 11/2016 |

OTHER PUBLICATIONS

United States Patent Office Action for U.S. Appl. No. 16/986,492 dated Sep. 15, 2022 (24 pages).

Abe et al., "CGS20267 (Letrozole), a new aromatase inhibitor: late phase II study for postmenopausal women with advanced or recurrent breast cancer (No. 1)—investigation of recommended clinical dose CGS20267 Study Group," Gan To Kagaku Ryoho, 2002, 29(5):729-40.

Acevedo et al., "Selective Androgen Receptor Modulators Antagonize Apolipoprotein E4-Induced Cognitive Impairments," Letters in Drug Design & Discovery, 2008, 5, 271-276.

ACOG, "Selective Estrogen Receptor Modulators," International Journal of Gynecology & Obstetrics, 2002, 79:289-298.

Agrawal et al., "Biological effects of fulvestrant on estrogen receptor positive human breast cancer: short, medium and long-term effects based on sequential biopsies," Int. J. Cancer, 2016, 138:146-159.

Ahn et al., "Genetic Screen Identifies Insulin-like Growth Factor Binding Protein 5 as a Modulator of Tamoxifen Resistance in Breast Cancer," Cancer Research, 2010, 70(8):3013-3019.

Ali et al., "Antiestrogens and Their Therapeutic Applications in Breast Cancer and Other Diseases," Annu. Rev. Med., 2011, 62:217-32.

Ali et al., "Endocrine-Responsive Breast Cancer and Strategies for Combating Resistance," Cancer, 2002, 2:101-115.

Allan et al., "A selective androgen receptor modulator that reduces prostate tumor size and prevents orchidectomy-induced bone loss in rats," Journal of Steroid Biochemistry & Molecular Biology, 2007, 103, 76-83.

Allan et al., "A selective androgen receptor modulator with minimal prostate hypertrophic activity enhances lean body mass in male rats and stimulates sexual behavior in female rats," Endocr., 2007, 32:41-51.

Alluri et al., "Estrogen receptor mutations and their role in breast cancer progression," Breast Cancer Research, 2014, 16:494, 8 pages.

Anderson, "The Process of Structure-Based Drug Design," Chemistry & Biology, 2003, vol. 10, 787-797.

(56) References Cited

OTHER PUBLICATIONS

Angus et al., "ESR1 mutations: Moving towards guiding treatment decision-making in metastatic breast cancer patients," Cancer Treatment Reviews, 2017, 52:33-40.
Anonymous: "Radius (RDUS) Announced Today That it Has Acquired The License to Develop and Market RAD1901 in Japan", MPM—Globe Newswire, Mar. 10, 2015 (Mar. 10, 2015), pp. 1-5.
Anonymous: "Radius Presents Positive Results from Phase IB Clinical Trial of BA058 and Preclinical Study of RAD1901 at the Endocrine Society 2007 Annual Meeting, Evaluate", Jun. 8, 2007 (Jun. 8, 2007), pp. 1-2.
Argenta et al., "Predicting response to the anti-estrogen fulvestrant in recurrent," Gynecologic Oncology, 2013, 131:368-373.
Arlt et al., "Elacestrant (RAD1901) demonstrates anti-tumor activity in a fulvestrant-resistant PDX model," San Antonio Breast Cancer Symposium, Dec. 5-9, 2017.
Arpino et al., "Crosstalk between the Estrogen Receptor and the HER Tyrosine Kinase Receptor Family: Molecular Mechanism and Clinical Implications for Endocrine Therapy Resistance," Endocrine Reviews, 2008, 29(2):217-233.
Arun et al., "The search for the ideal SERM," Expert Opin. Pharmacother., 2002, 3(6):681-691.
Augereau et al., "Hormonoresistance in advanced breast cancer: a new revolution in endocrine therapy," Ther Adv Med Oncol., 2017, 9(5):335-346.
Awada et al., "The oral mTOR inhibitor RAD001 (everolimus) in combination with letrozole in patients with advanced breast cancer: Results of a phase I study with pharmacokinetics," European Journal of Cancer, 2008, 44:84-91.
Bardia et al., "Elacestrant, oral selective estrogen receptor degrader (SERD) in patients with ER positive (ER+)/HER2—advanced breast cancer: Updated phase 1 efficacy and pharmacodynamic results," San Antonio Breast Cancer Symposium—Dec. 5-9, 2017.
Barraja et al., "Indolo[3,2-c]cinnolines with Antiproliferative, Antifungal, and Antibacterial Activity," Bioorganic & Medicinal Chemistry, 1999, 7:1591-1596.
Baselga et al., "Buparlisib plus fulvestrant versus placebo plus fulvestrant in postmenopausal, hormone receptor-positive, HER2-negative, advanced breast cancer (BELLE-2): a randomised, double-blind, placebo-controlled, phase 3 trial," The Lancet, 2017, 13 pages.
Baselga et al., "PIK3CA Status in Circulating Tumor DNA Predicts Efficacy of Buparlisib Plus Fulvestrant in Postmenopausal Women With Endocrine-resistant HR+/HER2—Advanced Breast Cancer: First Results From the Randomized, Phase III BELLE-2 Trial," San Antonio Breast Cancer Symposium, 2015.
Baumann et al., "Estrogen Receptor Modulators and Down Regulators, Optimal Use in Postmenopausal Women With Breast Cancer," Drugs 2007; 67 (16): 2335-2353.
Beelen et al., "Phosphorylated p-7S6K predicts tamoxifen resistance in postmenopausal breast cancer patients randomized between adjuvant tamoxifen versus no systemic treatment," Breast Cancer Research, 2014, 16:R6.
Beelen et al., "PI3K/AKT/mTOR pathway activation in primary and corresponding metastatic breast tumors after adjuvant endocrine therapy," Int. J. Cancer, 2014, 135:1257-1263.
Begam et al., "Estrogen receptor agonists/antagonists in breast cancer therapy: A critical review," Bioorganic Chemistry, 2017, 18 pages.
Beilstein Registry No. 173027 (2010).
Beilstein Registry No. 2109126 (2010).
Beilstein Registry No. 8619569 (2010).
Beith et al., "Hormone receptor positive, HER2 negative metastatic breast cancer: A systematic review of the current treatment landscape," Asia-Pacific Journal of Clinical Oncology 2016, 12(Suppl. 1): 3-18.
Bell et al., "Genetic Engineering of Hybridoma Glutamine Metabolism," Enzyme and Microbial Technology, 1995, 17:98-106.

Bencze et al., "Synthetic Estrogens, Implantation Inhibitors, and Hypocholesterolemic Agents. I. Tetrahydronaphthalene Series," Estrogenic Tetrahydronaphthalene Derivatives, 1967, pp. 138-144.
Bentzon et al., "Prognostic effect of estrogen receptor status across age in primary breast cancer," Int. J. Cancer, 2008, 122:1089-1094.
Benz et al., "Estrogen-dependent, tamoxifen-resistant tumorigenic growth of MCF-7 cells transfected with HER2/neu," Breast Cancer Research and Treatment, 1992, 24:85-95.
Berge et al., "Pharmaceutical Salts," Journal of Pharmaceutical Sciences, 1977, 66(1):1-19.
Berrodin et al., "Differential Biochemical and Cellular Actions of Premarin Estrogens: Distinct Pharmacology of Bazedoxifene-Conjugated Estrogens Combination," Mol Endocrinol, 2009, 23(1):74-85.
Bihani et al., "Elacestrant (RAD1901), a Selective Estrogen Receptor Degrader (SERD), Has Antitumor Activity in Multiple ER+ Breast Cancer Patient-derived Xenograft Models," Clinical Cancer Research, AACR, 2017, OF1-OF12.
Bihani et al., "RAD1901 demonstrates anti-tumor activity in multiple models of ER-positive breast cancer treatment resistance," San Antonio Breast Cancer Symposium—Dec. 6-10, 2016.
Bihani et al., "RAD1901, an orally available selective estrogen receptor degrader (SERD), has potent anti-tumor activity in in vitro and in vivo models of ER+ breast cancer," Abstract: C100, Poster Session: PO.C12. Hormonal Agents and Therapy, Nov. 8, 2015. Presented at the AACR-NCI-EORTC International Conference on Molecular Targets and Cancer Therapeutics, Boston, MA.
Bihani et al., "RAD1901, an orally available SERD, as an effective combination partner in ER+ breast cancer," AACR 2016, Poster Session 1: Molecular Endocrinology of Hormone-dependent Malignancies; Apr. 18, 2016.
Bisagni et al., "Letrozole, a new oral non-steroidal aromatase inhibitor in treating postmenopausal patients with advanced breast cancer. A pilot study," Annals of Oncology, 1996, 7:99-102.
Bogani et al., "mTOR Inhibitors Alone and in Combination with JAK2 Inhibitor Effectively Inhibit Cells of Myeloproliferative Neoplasms," PLOS One, 2013, vol. 8, Issue 1, e54826.
Bohl et al., "Structural Basis for Accommodation of Nonsteroidal Ligands in the Androgen Receptor," The Journal of Biological Chemistry, 2005, vol. 280, No. 45, pp. 37747-37754.
Bohl et al., "Structural basis for antagonism and resistance of bicalutamide in prostate cancer," PNAS, 2005, vol. 102, No. 17, 6201-6206.
Bosch et al., "Delineating novel molecular pathways driving endocrine resistance in breast cancer," Poster No. P3-04-27, SABCS 2016.
Bostner et al., "Activation of Akt, mTOR, and the estrogen receptor as a signature to predict tamoxifen treatment benefit," Breast Cancer Res Treat, 2013, 137:397-406.
Boyer et al., "Cyclization from Aryl Formamides in Phosphorus Oxychloride and Tin(IV) Chloride," International Journal of Methods in Synthetic Organic Chemistry, 1978, No. 3, p. 205.
Brankovic-Magic et al., "Progesterone receptor status of breast cancer metastases," J Cancer Res Clin Oncol, 2002, 128:55-60.
Browne, "Isotope Effect: Implications for Pharmaceutical Investigations," Stable Isotopes in Pharmaceutical Research, 1997, vol. 26, Chapter 2, pp. 13-18.
Brufsky, "Long-term management of patients with hormone receptor-positive metastatic breast cancer: Concepts for sequential and combination endocrine-based therapies," Cancer Treatment Reviews, 2017, 59:22-32.
Brzozowski et al., "Molecular basis of agonism and antagonism in the oestrogen receptor," Nature, 1999, 389:753-758.
Burstein et al., "Adjuvant Endocrine Therapy for Women With Hormone Receptor-Positive Breast Cancer: American Society of Clinical Oncology Clinical Practice Guideline Focused Update," Journal of Oncology, 2014, 16 pages.
Butt et al., "Downstream targets of growth factor and oestrogen signalling and endocrine resistance: the potential roles of c-Myc, cyclin D1 and cyclin E," Endocrine-Related Cancer, 2005, 12:S47-S59.

(56) References Cited

OTHER PUBLICATIONS

Caceres et al., "Flutamide reduced tumor progression and altered steroid hormone secretion in human and canine inflammatory breast cancer cell lines," Poster No. P3-05-07, SABCS 2016.

Cadoo et al., "Palbociclib: an evidence-based review of its potential in the treatment of breast cancer," Breast Cancer: Targets and Therapy, 2014, 6:123-133.

Callis et al., "A Screening Assay Cascade to Identify and Characterize Novel Selective Estrogen Receptor Downregulators (SERDs)," Journal of Biomolecular Screening, 2015, 20(6):784-759.

Campbell et al., "Phosphatidylinositol 3-Kinase/AKT-mediated Activation of Estrogen Receptor α," The Journal of Biological Chemistry, 2001, 276(13):9817-9824.

Cantin et al., "Structural Characterization of the Human Androgen Receptor Ligand-biding Domain Complexed with EM5744, a Rationally Designed Steroidal Ligand Bearing a Bulky Chain Directed toward Helix 12," The Journal of Biological Chemistry, 2007, vol. 282, No. 42, pp. 30910-30919.

Cardoso et al., "ESO-ESMO 2nd international consensus guidelines for advanced breast cancer (ABC2)," Annals of Oncology, 2014, 25:1871-1888.

Carlson et al., "Altered Ligand Binding Properties and Enhanced Stability of a Constitutively Active Estrogen Receptor: Evidence That an Open Pocket Conformation is Required for Ligand Interaction," Biochemistry, 1997, 36, 14897-14905.

Carlson, "The History and Mechanism of Action of Fulvestrant," Clinical Breast Cancer, 2005, 6(1):S5-S8.

Cesnjaj et al., "In Vivo Models in the Study of Osteopenias," Eur. J. Clin. Chem. Clin. Biochem., 1991, vol. 29, pp. 211-219.

Chang et al., "Application of Random Peptide Phage Display to the Study of Nuclear Hormone Receptors," Methods Enzymol. (2003) 364:118-42.

Chang et al., "Dissection of the LXXLL Nuclear Receptor-Coactivator Interaction Motif Using Combinatorial Peptide Libraries: Discovery of Peptide Antagonists of Estrogen Receptors α and β," Mol Cell Biol. (1999) 19(12):8226-39.

Clarke et al., "Endocrine resistance in breast cancer—an overview and update," Mol Cell Endocrinol, 2015, 418(03):220-234.

Compston, "Sex Steroids and Bone," Physiological Reviews, 2001, 81(1):419-447.

Connor et al., "Circumventing Tamoxifen Resistance in Brest Cancers Using Antiestrogens That Induce Unique Conformational Changes in the Estrogen Receptor," Cancer Res. (2001) 61(7):2917-22.

Cosman et al., "Selective estrogen-receptormodulators," Clin Geriatr Med, 2003, 19:371-379.

Creevey et al., "The impact of circulating androgens on the androgen receptor in aromatase inhibitor resistant breast cancer," Poster No. P3-04-18, SABCS 2016.

Cristofanilli et al., "Fulvestrant plus palbociclib versus fulvestrant plus placebo for treatment of hormone-receptor-positive, HER2-negative metastatic breast cancerthat progressed on previous endocrine therapy (PALOMA-3): final analysis of the multicentre, double-blind, phase 3 randomised controlled trial," Lancet Oncol, 2016, 15 pages.

Cummings et al., "The effect of Raloxifene on Risk of Breast Cancer in Postmenopausal Women," JAMA, 1999, 281 (23):2189-2197.

Dave et al., "The pharmacokinetics of letrozole in brain and brain tumor in rats with orthotopically implanted C6 glioma, assessed using intracerebral microdialysis," Cancer Chemother Pharmacol, 2013, 72:349-357.

Dawson et al., "Analysis of Circulating Tumor DNA to Monitor Metastatic Breast Cancer," The New England Journal of Medicine, 2013, 368:1199-209.

De Savi et al., "Optimization of a novel binding motif to (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid (AZD9496), a potent and orally bioavailable selective estrogen receptor downregulator and antagonist," Journal of Medicinal Chemistry, 2015, 38 pages.

DeFriend et al., "Investigation of a New Pure Antiestrogen (ICI 182780) in Women with Primary Breast Cancer," Cancer Research, 1994, 54:408-414.

DeMichele et al., "CDK 4/6 Inhibitor Palbociclib (PD0332991) in Rb+ Advanced Breast Cancer: Phase II Activity, Safety, and Predictive Biomarker Assessment," Clinical Cancer Research, 2014, 21(5):995-1001.

Deshmane et al., "Phase III Double-Blind Trial of Arzoxifene Compared With Tamoxifen for Locally Advanced or Metastatic Breast Cancer," Journal of Clinical Oncology, 2007, vol. 25, No. 31, pp. 4967-4973.

Di Leo et al., "Final Overall Survival: Fulvestrant 500 mg vs 250 mg in the Randomized Confirm Trial," J Natl Cancer Inst, 2014, 106(1): djt337.

Dienstmann et al., "Picking the Point of Inhibition: A Comparative Review of PI3K/AKT/mTOR Pathway Inhibitors," Mol. Cancer Ther., 2014, pp. 1021-1031.

Dowsett et al., "Assessment of Ki67 in Breast Cancer: Recommendations from the International Ki67 in Breast Cancer Working Group," J Natl Cancer Inst, 2011, 103:1656-1664.

Dowsett et al., "Endocrine Therapy, New Biologicals, and New Study Designs for Presurgical Studies in Breast Cancer," J Natl Cancer Inst Monogr, 2011,43:120-123.

Dowsett et al., "Meta-Analysis of Breast Cancer Outcomes in Adjuvant Trials of Aromatase Inhibitors Versus Tamoxifen," Journal of Clinical Oncology, 2010, 28(3):509-518.

Duka et al., "The effects of 3-week estrogen hormone replacement on cognition in elderly healthy females," Psychopharmacology, 2000, 149:129-139.

Dutertre et al., "Molecular Mechanisms of Selective Estrogen Receptor Modulator (SERM) Action," The Journal of Pharmacology and Experimental Therapeutics, 2000, 295(2):431-437.

Eisenhauer et al., "New response evaluation criteria in solid tumours: Revised RECIST guideline (version 1.1)," European Journal of Cancer, 2009, 45:228-247.

Ellis et al., "Fulvestrant 500 mg Versus Anastrozole 1 mg for the First-Line Treatment of Advanced Breast Cancer: Overall Survival Analysis From the Phase II First Study," Journal of Clinical Oncology, 2015, 33(32): 3781-3787.

Encyclopaedia Britannica Online, "Deuterium," <http://www.britannica.com/EBchecked/topic/159684/deuterium> Feb. 18, 2009.

Ettinger et al., "Reduction of Vertebral Fracture Risk in Postmenopausal Women With Osteoporosis Treated With Raloxifene," JAMA, 1999, 262(7):637-646.

Evans et al., "Prevalence of Alzheimer's Disease in a Community Population of Older Persons," JAMA, 1989, 262(18):2551-2556.

Fan et al., "Endocrine therapy resistance in breast cancer: current status, possible mechanisms and overcoming strategies," Future Med. Chem., 2015, 7(12):1511-1519.

Fanning et al., "Estrogen receptor alpha somatic mutations Y537S and D538G confer breast cancer endocrine resistance by stabilizing the activating function-2 binding conformation," eLife, 2016, 5:e12792.

Finn et al., "Efficacy and safety of palbociclib in combination with letrozole as first-line treatment of ER-positive, HER2-negative, advanced breast cancer: Expanded analyses of subgroups from the randomized pivotal trial PALOMA-1/TRIO-18," Breast Cancer Research, 2016, 18:67.

Fowler et al., "Small-Animal PET of Steroid Hormone Receptors Predicts Tumor Response to Endocrine Therapy Using a Preclinical Model of Breast Cancer," J Nucl Med, 2012, 53:1119-1126.

Fox et al., "A Kinome-Wide Screen Identifies the Insulin/IGF-I Receptor Pathway as a Mechanism of Escape from Hormone Dependence in Breast Cancer," Cancer Res, 2011, 71:6773-6784.

Francis et al., "Adjuvant Ovarian Suppression in Premenopausal Breast Cancer," N Engl J Med., 2015, 372(5):436-446.

Fribbens et al., "Plasma ESR1 Mutations and the Treatment of Estrogen Receptor-Positive Advanced Breast Cancer," Journal of Clinical Oncology, 2016, 10 pages.

Friend et al., "The Changing Landscape of Breast Cancer" How Biology drives Therapy, Medicines, 2016, 3(2):14 pages.

(56) References Cited

OTHER PUBLICATIONS

Fu et al., "Connections to the Directed Ortho Metalation Strategy. Pd(0)-Catalyzed Cross Coupling of Aryl Boronic Acids with Aryl Triflates," Tetrahedron Letters, 1990, vol. 31, No. 12, pp. 1665-1668.

Gajdos et al., "Selective Estrogen Receptor Modulators as a New Treatment Drug Group: Concept to Reality in a Decade," Clinical Breast Cancer, 2002, pp. 272-281.

Gao et al., "Comparison of the Pharmacological Effects of a Novel Selective Androgen Receptor Modulator, the 5α-Reductase Inhibitor Finasteride, and the Antiandrogen Hydroxyflutamide in Intact Rats: New Approach for Benign Prostate Hyperplasia," Endocrinology, 2004, 145(12):5420-5428.

Gao et al., "Expanding the therapeutic use of androgens via selective androgen receptor modulators (SARMs)" Drug Discovery Today, 2007, vol. 12, No. 5/6, pp. 241-248.

Gao et al., "Ockham's Razor and Selective Androgen Receptor Modulators (SARMs): Are We Overlooking the Role of 5α-Reductase?" Molecular Interventions, 2007, vol. 7, Issue 1, 10-13.

Gao et al., "Selective Androgen Receptor Modulator Treatment Improves Muscle Strength and Body Composition and Prevents Bone Loss in Orchidectomized Rats," Endocrinology, 2005, 146(11):4887-4897.

Garcia-Becerra et al., "Mechanisms of Resistance to Endocrine Therapy in Breast Cancer: Focus on Signaling Pathways, miRNAs and Genetically Based Resistance," Int. J. Mol. Sci, 2013, 14:108-145.

Garner et al., "RAD1901, a novel oral, selective estrogen receptor degrader (SERD) with single agent and combination efficacy in wild-type and mutant ER+ patient-derived xenograft (PDx) models," Poster No. P3-05-07. Poster Session 3: Tumor Cell and Molecular Biology. Endocrine Therapy and Resistance. Presented at the San Antonio Breast Cancer Symposium on Dec. 10, 2015.

Garner et al., "RAD1901: a novel, orally bioavailable selective estrogen receptor degrader that demonstrates antitumor activity in breast cancer xenograft models," Anti-Cancer Drugs, 2015, 9 pages.

Giessrigl et al., "Fulvestrant induces resistance by modulating GPER and CDK6 expression: Implication of methyltransferases, deacetylases and the hSWI/SNF chromatin remodelling complex," British Journal of Cancer, 2013, 109:2751-2762.

Gitto et al., "Recent insights into the pathophysiology of mTOR pathway dysregulation," Research and Reports in Biology, 2015, 6:1-16.

Glück, "Extending the Clinical Benefit of Endocrine Therapy for Women With Hormone Receptor-Positive Metastatic Breast Cancer: Differentiating Mechanisms of Action," Clinical Breast Cancer, 2014, 14(2):75-84.

Goetz et al., "Window-of-Opportunity Trials in the Preoperative Settings: Insights Into Drug Development for Estrogen Receptor-Positive Breast Cancer," Journal of Oncology, 2016 34(17): 1970-1972.

Goldstein et al., "A pharmacological review of selective oestrogen receptor modulators," Human Reproduction Update, 2000, 6(3):212-224.

Gopinath et al., "Synthesis of Some 1: 2- and 7: 8-Benzophenanthridines," J. Chem. Soc., 1958, 1144: 504-509.

Gottardis et al., "Effect of Steroidal and Nonsteroidal Antiestrogens on the Growth of a Tamoxifen-stimulated Human Endometrial Carcinoma (EnCa101) in Athymic Mice," Cancer Research, 1990, 50:3189-3192.

Gradishar et al., "Effects of High Dose Raloxifene in Selected Patients with Advanced Breast Carcinoma," Cancer, 2000, vol. 88, No. 9, pp. 2047-2053.

Gross et al., "Multiple Progesterone Receptor Assays in Human Breast Cancer," Cancer Research, 1984, 44:836-840.

Haddow et al., "Influence of Synthetic Oestrogens Upon Advanced Malignant Disease," British Medical Journal, 1944, pp. 394-368.

Hamann, "Discovery and Preclinical Profile of a Highly Potent and Muscle Selective Androgen Receptor Modulator (SARM)" 227th National Meeting of the American Chemical Society Medicinal Chemistry Division, 2004, 42 pages.

Hamaoka et al., "Design, synthesis and structure-activity relationships of novel tetrahydronaphthalene SERMs derivatives," Drugs of the future, 2004, v. 29, suppl. A, p. 177.

Hamel et al., "Unexpected Acid-catalyzed Rearrangement of Certain 3-(Arylthio)indoles to 2-(2-Aminophenyl)benzothiophenes," J. Chem. Soc. Chem. Commun., 1990, pp. 1072-1074.

Hammond et al., "American Society of Clinical Oncology/College of American Pathologists Guideline Recommendations for Immunohistochemical Testing of Estrogen and Progesterone Receptors in Breast Cancer," Ach Pathol Lab Med., 2010, 134(6):907-922.

Hanada et al., "Bone Anabolic Effects of S-40503, a Novel Nonsteroidal Selective Androgen Receptor Modulator (SARM), in Rat Models of Osteoporosis," Biol. Pharm. Bull., 2003, 26(11):1563-1569.

Harb et al., "A Phase 1 study of RAD1901, a novel, orally available, selective estrogen receptor degrader, for the treatment of ER positive advanced breast cancer," Poster No. OT2-01-01. Presented at San Antonio Breast Cancer Symposium. Dec. 10, 2015.

Hattersley et al., "A Phase 1 dose escalation study of RAD1901, an oral selective estrogen receptor degrader, in healthy postmenopausal women," Poster No. P6-13-02, Poster Session: 6—Treatment: New Drugs and Treatment Strategies. Presented at San Antonio Breast Cancer Symposium on Dec. 12, 2015.

Hattersley et al., (2007) "RAD-1901, a Novel SERM, has Efficacy in an Animal Model of Vasomotor Symptoms," Radius Health, Inc. (1 pages).

He et al., "Comparison of $^{18}$F-FES, $^{18}$F-FDG, and $^{18}$F-FMISO PET Imaging Probes for Early Prediction and Monitoring of Response to Endocrine Therapy in a Mouse Xenograft Model of ER-Positive Breast Cancer," PLoS ONE, 2016, 11(7):e0159916.

Heldring et al., "Estrogen Receptors: How Do They Signal and What are Their Targets," Physiol Rev, 2007, 87:905-931.

Henderson, "Estrogen Replacement Therapy for the Prevention and Treatment of Alzheimer's Disease," CNS Drugs, 1997, 8(5):343-351.

Henderson, "The epidemiology of estrogen replacement therapy and Alzheimer's disease," Neurology, 1997, 48(Suppl 7) S27-S35.

Higuchi et al., "Novel Series of Potent, Nonsteroidal, Selective Androgen Receptor Modulators Based on 7H-[1,4]Oxazino[3,2-g]quinolin-7-ones," J. Med. Chem., 2007, 50, 2486-2496.

Hörig et al., "From bench to clinic and back: Perspective on the 1$^{st}$ IQPC Translational Research Conference," Journal of Translational Medicine, 2004, 2:44.

Hosford et al., "ER reactivation rapidly elicits cell death effects in anti-estrogen-resistant breast cancer," Poster No. P3-04-06, SABCS 2016.

Howell et al., "Comparison of Fulvestrant Versus Tamoxifen for the Treatment of Advanced Breast Cancer in Postmenopausal Women Previously Untreated With Endocrine Therapy: A Multinational, Double-Blind, Randomized Trial," Journal of Clinical Oncology, 2004, 22(9):1605-1613.

Howell et al., "The use of selective estrogen receptor modulators and selective estrogen receptor down-regulators in breast cancer," Best Practice & Research Clinical Endocrinology & Metabolism, 2004, 18(1):47-66.

Huang et al., "A Newfound Cancer-Activating Mutation Reshapes the Energy Landscape of Estrogen-Binding Domain," J. Chem. Theory Comput., 2014, 10, 2897-2900.

Huang et al., "Identification of a Negative Regulatory Surface within Estrogen Receptor a Provides Evidence in Support of a Role for Corepressors in Regulating Cellular Responses to Agonists and Antagonists," Mol. Endocrinol. (2002) 16(8):1778-92.

Huang et al., "Mechanisms of resistance to selective estrogen receptor down-regulator in metastatic breast cancer," BBA—Reviews on Cancer, 2017, 1868:148-156.

Huijts et al., "Differential effects of inhibitors of the PI3K/mTOR pathway on the expansion and functionality of regulatory T cells," Clinical Immunology, 2016, 36 pages.

Hutcheson et al., "Fulvestrant-induced expression of ErbB3 and ErbB4 receptors sensitizes oestrogen receptor-positive breast cancer cells to heregulin β1," Breast Cancer Research, 2011, 13:R29.

(56) References Cited

OTHER PUBLICATIONS

Iwamoto et al., "Estrogen Receptor (ER) mRNA and ER-Related Gene Expression in Breast Cancers That are 1% to 10% ER-Positive by Immunohistochemistry," Journal of Clinical Oncology, 2012, 30(7):729-734.

Jeng et al., "Estrogen Receptor Expression and Function in Long-Term Estrogen-Deprived Human Breast Cancer Cells," Endocrinology, 1998, 139(10):4164-4174.

Jeselsohn et al., "Emergence of Contitutively Active Estrogen Receptor-α Mutations in Pretreated Advanced Estrogen Receptor-Positive Breast Cancer," Clinical Cancer Research, 2014, 20:1757-1767.

Jeselsohn et al., "ESR1 mutations as a mechanism for acquired endocrine resistance in breast cancer," Nat Rev Clin Oncol., 2015, 12(10):573-583.

Jeyakumar et al., "Exploration of Dimensions of Estrogen Potency," The Journal of Biological Chemistry, 2011, 286(15):12971-12982.

Johnson et al., "Steroid Receptor Coactivators 1,2, and 3: Critical Regulators of Nuclear Receptor Activity and Steroid Receptor Modulator (SRM)-based Cancer Therapy," Mol Cell Endocrinol., 2012, 348(2):430-439.

Johnston et al., Comparison of Estrogen Receptor DNA Binding in Untreated and Acquired Antiestrogen-resistant Human Breast Tumors, Cancer Research, 1997, 57:3723-3727.

Johnston et al., "Endocrine Manipulation in Advanced Breast Cancer: Recent Advances with SERM Therapies," Clinical Cancer Research, 2001, vol. 7, pp. 4376s-4387s.

Johnston, "Enhancing Endocrine Therapy for Hormone Receptor-Positive Advanced Breast Cancer: Cotargeting Signaling Pathways," JNCI J Natl Cancer Inst, 2015, 107(10):djv212.

Jones et al., "Antiestrogens. 2. Structure-Activity Studies in a Series of 3-Aroyl-2-arylbenzo[b]thiophene Derivatives Leading to [6-Hydroxy-2-(4-hydroxyphenyl)benzo[b]thien-3-yl] [4-[2-(1-piperidinyl)ethoxy]-phehyl]methanone Hydrochloride (LY156758), a Remarkably Effective Estrogen Antagonist with Only Minimal Intrinsic Estrogenicity," J. Med. Chem., 1984, 27:1057-1066.

Jordan et al., "Effects of anti-estrogens on bone in castrated and intact female rats," Breast Cancer Research and Treatment, 1987, 10:31-35.

Jordan, "The secrets of selective estrogen receptor modulation: Cell-specific coregulation" Cancer Cell, 2002, 215-217.

Joseph et al., "The selective estrogen receptor downregulator GDC-0810 is efficacious in diverse models of ER+ breast cancer," eLife, 2016, 5:e15828.

Kaklamani et al., "A phase 1 study of RAD1901, a novel, oral selective estrogen degrader, for the treatment of ER positive advanced breast cancer," San Antonio Breast Cancer Symposium—Dec. 6-10, 2016.

Kaplan et al., "Strategies for the management of adverse events associated with mTOR inhibitors," Transplantation Reviews, 2014, 28:126-133.

Karlsson et al., "The mTOR effectors 4EBP1 and S6K2 are frequently coexpressed, and associated with a poor prognosis and endocrine resistance in breast cancer: a retrospective study including patients from the randomised Stockholm tamoxifen trials," Breast Cancer Research, 2013, 15:R96, 14 pages.

Kemppainen et al., "Distinguishing Androgen Receptor Agonists and Antagonists: Distinct Mechanisms of Activation by Medroxyprogesterone Acetate and Dihydrotestosterone," Molecular Endocrinology, 1999, vol. 13, No. 3, 440-454.

Kieser et al., "Characterization of the Pharmacophore Properties of Novel Selective Estrogen Receptor Downregulators (SERDs)," Journal of Medicinal Chemistry, 2010, vol. 53, No. 8, pp. 3320-3329.

Kilbourne et al., "Selective androgen receptor modulators for frailty and osteoporosis," Current Opinion in Investigational Drugs, 2007, 8(10):821-829.

Kim et al., "The 4-Para Substituent of S-3-(phenoxy)-2-hydroxy-2-methyl-N(4-nitro-3-trifluoromethyl-phenyl)-propionamides is a Major Structural Determinant of In Vivo Disposition and Activity of Selective Androgen Receptor Modulators," American Society for Pharmacology and Experimental Therapeutics, 2005, 42 pages.

Kinoyama et al., "(+)-(2R,5S)-4-[4-Cyano-3-(trifluotomethyl)phenyl]-2,5-dimethyl-N-[6-(trifluoromethyl)pyridin-3-yl]piperazine-a-carboxamide (YM580) as an Orally Potent and Peripherally Selective Nonsteroidal Androgen Receptor Antagonist," J. Med. Chem., 2006, 49, 716-726.

Kocanova et al., "Ligands specify estrogen receptor alpha nuclear localization and degradation," BMC Cell Biology, 2010, 11:98, 13 pages.

Komm et al., "An overview of current and emerging SERMs," Journal of Steroid Biochemistry and Molecular Biology, 2014, vol. 143, pp. 207-222.

Kono et al., "Impact of Androgen Receptor Expression in Fluoxymesterone-Treated Estrogen receptor-Positive Metastatic Breast Cancer Refractory to Contemporary Hormonal Therapy," Poster No. P3-05-04, SABCS 2016.

Krop et al., "Pictilisib for oestrogen receptor-positive, aromatase inhibitor-resistant, advanced or metastatic breast cancer (FERGI): a randomised, double-blind, placebo-controlled, phase 2 trial," The Lancet, 2016, 17(6):811-821.

Labrie et al., "EM-652 (SCH57068), a pure SERM having complete antiestrogenic activity in the mammary gland and endometrium," Journal of Steroid Biochemistry & Molecular Biology, 2001, 79:213-225.

Lamb et al., "Cell cycle regulators cyclin D1 and CDK4/6 have estrogen receptor-dependent divergent functions in breast cancer migration and stem cell-like activity," Cell Cycle, 2013, 12:15, 2384-2394.

Le Romancer et al., "Cracking the Estrogen Receptor's Post-translational Code in Breast Tumors," Endocrine Reviews, 2011, 32(5):597-622.

Lednicer et al., "A Novel Sequence for the Preparation of 1,2-Disubstituted 3,4-Dihydronaphthalenes," Mammalian Antifertility Agents VI, 1969, vol. 12, pp. 881-885.

Lednicer et al., "Basic 3,4-Dihydronaphthalenes and 1,2,3,4-Tetrahydro-1-naphthols," Mammalian Antifertility Agents IV, 1967, vol. 10, pp. 78-84.

Lenihan et al., "CDK4/6 inhibitor resistant ER-positive cells remain dependent on estrogen signalling and retain sensitivity to endocrine therapy," Poster No. P3-03-12, SABCS 2016.

Lewis-Wambi et al., "Treatment of Postmenopausal Breast Cancer with Selective Estrogen Receptor Modulators (SERMs)," Breast Disease, 2005-2006, 93-105.

Li et al., "Endocrine-Therapy-Resistant ESR1 Variants Revealed by Genomic Characterization of Breast-Cancer-Derived Xenografts," Cell Reports, 2013, 4:1116-1130.

Li et al., "The selective estrogen receptor modulators in breast cancer prevention," Cancer Chemother Pharmacol, 2016, 77:895-903.

Littleton-Kearney et al., "Selective Estrogen Receptor Modulators: Tissue Actions and Potential for CNS Protection," CNS Drug Reviews, 2002, 8(3):309-330.

Loi et al., "Predicting prognosis using molecular profiling in estrogen receptor-positive breast cancer treated with tamoxifen," BMC Genomics, 2008, 9:239, 12 pages.

Lombardi et al., "Estrogens and health in males," Molecular and Cellular Endocrinology, 2001, 178:51-55.

Loose-Mitchell et al., "Estrogens and Progestins," Goodman and Gilman's, The Pharmacological Basis of Therapeutics, 10th Edition, 2001, Chapter 58, pp. 1597-1634.

Lopez-Tarruella et al., "The Dynamics of Estrogen Receptor Status in Breast Cancer: Reshaping the Paradigm," Clin Cancer Res, 2007, 13(23):6921-6925.

Loprinzi et al., "Management of hot flashes in breast-cancer survivors," The Lancet Oncology, 2001, vol. 2, 199-204.

Ma et al., "Raloxifene and teriparatide (hPTH 1-34) have complementary effects on the osteopenic skeleton of ovariectomized rats," J Bone Miner Metab, 2005, 23[Suppl]:62-68.

Macedo et al., "Combination of Anastrozole with Fulvestrant in the Intratumoral Aromatase Xenograft Model," Cancer Res, 2008, 68(9):3516-3522.

(56) References Cited

OTHER PUBLICATIONS

Marino et al., "Estrogen Signaling Multiple Pathways to Impact Gene Transcription," Current Genomics, 2006, 7, 497-508.
Martin et al., "Resistance to palbociclib depends on multiple targetable mechanisms highlighting the potential of drug holidays and drug switching to improve therapeutic outcome," The Institute of Cancer Research, Poster No. P3-03-09, 2016.
Martinborough et al., "Substituted 6-(1-Pyrrolidine)quinolin-2(1H)-ones as Novel Selective Androgen Receptor Modulators," Journal of Medicinal Chemistry, 2007, vol. 50, No. 21, 5049-5052.
Martinkovich et al., "Selective estrogen receptor modulators: tissue specificity and clinical utility," Clinical Interventions in Aging, 2014, 9:1437-1452.
Massarweh et al., "Mechanisms of tumor Regression and Resistance to Estrogen Deprivation and Fulvestrant in a Model of Estrogen Receptor-Positive, HER-2/neu-Positive Breast Cancer," Cancer Res, 2006, 66(16):8266-8273.
Maugeri-Sacca et al., "Presurgical window of opportunity trial design as a platform fortesting anticancer drugs: Pros, cons and a focus on breast cancer," Critical Reviews in Oncology/Hematology, 2016, 106:132-142.
Maximov et al., "The Discovery and Development of Selective Estrogen Receptor Modulators (SERMs) for Clinical Practice," Current Clinical Pharmacology, 2013, 8:135-155.
McDonnell et al., "Oral Selective Estrogen Receptor Downregulators (SERDs), a Breakthrough Endocrine Therapy for Breast Cancer," J. Med. Chem., 2015, 58:4883-4887.
McGinley et al., "Circumventing Anti-Androgen Resistance by Molecular Design," J. Am. Chem. Soc., 2007, 129, 3822-3823.
MedlinePlus, "Autoimmune disorder," U.S. National Library of Medicine, NIH National Institute of Health, <http://www.nlm.nih.gov/medlineplus/ency/article/000816.htm> Jun. 3, 2011.
Mendelsohn et al., "The Protective Effects of Estrogen on the Cardiovascular System," Mechanisms of Disease, 1999, 340(23):1801-1811.
Meng et al., "HER-2 gene amplification can be acquired as breast cancer progresses," PNAS, 2004, 101(25):9393-9398.
Merenbakh-Lamin et al., "D538G Mutation in Estrogen Receptor-α: A Novel Mechanism for Acquired Endocrine Resistance in Breast Cancer," Cancer Res, 2013, 73(23):6856-6864.
Miller et al., "Design, Synthesis, and Preclinical Characterization of Novel, Highly Selective Indole Estrogens," (2001) J Med Chem 44 (11):1654-1657.
Miller et al., "Design, Synthesis, and Preclinical Characterization of the Selective Androgen Receptor Modulator (SARM) RAD140," ACS Med. Chem. Lett., 2010, 6 pages.
Miller et al., "Hyperactivation of phosphatidylinositol-3 kinase promotes escape from hormone dependence in estrogen receptor-positive human breast cancer," The Journal of Clinical Investigation, 2010, 120(7):2406-2413.
Miller et al., "Loss of Phosphatase and Tensin Homologue Deleted on Chromosome 10 Engages ErbB3 and Insulin-Like Growth Factor-I Receptor Signaling to Promote Antiestrogen Resistance in Breast Cancer," Cancer Res, 2009, 69(10):4192-4201.
Miller et al., "Phosphatidylinositol 3-Kinase and Antiestrogen Resistance in Breast Cancer," Journal of Clinical Oncology, 2011, 29(33):4452-4461.
Miller et al., "Synthesis of potent, substitute carbazoles as selective androgen receptor modulators (SARMs)" Bioorganic & Medicinal Chemistry Letters, 2010, 20, 7516-7520.
Mirkin et al., "Selective estrogen receptor modulators (SERMs): A review of clinical data," Maturitas, 2015, 80:52-57.
Mitchell et al., "Design, Synthesis, and Biological Evaluation of 16-Substituted 4-Azasteroids as Tissue-Selective Androgen Receptor Modulators (SARMs)" Journal of Medicinal Chemistry Letter, 2009, 4 pages.
Mohler et al., "Nonsteroidal Selective Androgen Receptor Modulators (SARMs): Dissociating the Anabolic and Androgenic Activities of the Androgen Receptor for Therapeutic Benefit," J. Med. Chem., 2009, 20 pages.
Morello et al., "Pharmacokinetics of Selective Estrogen Receptor Modulators," Clin Pharmacokinet, 2003, 42(4):361-372.
Morikawa et al., "Clinical Trials for Breast Cancer with Brain Metastases: Challenges and New Directions," Current Breast Cancer Reports, 2013, vol. 5, No. 4, pp. 293-301.
Morrow et al., "Utility of the orally bioavailable selective estrogen receptor degrader AZD9496 in ESR1 mutant preclinical models of estrogen receptor positive breast cancer," Poster No. P3-04-10, SABCS 2016.
Muluhngwi et al., "Roles for miRNAs in endocrine resistance in breast cancer," Endocr Relat Cancer, 2015, 22(5):R279-R300.
Murphy et al., "Clinical significance of estrogen receptor phosphorylation," Endocrine-Related Cancer, 2011, 18:R1-R14.
Murray et al., "Intratumoural inflammation and endocrine resistance in breast cancer," Endocrine-Related Cancer, 2015, 22:R51-R67.
Musgrove, "Estrogen receptor degradation: a CUE for endocrine resistance?," Breast Cancer Research, 2011, 13:312.
Nardone et al., "The new oral SERD AZD9496 is efficacious in antagonizing ER and circumventing resistance to endocrine therapy," Poster No. P3-04-07, SABCS 2016.
Neven et al., "The Effect of Raloxifene on the Incident of Ovarian Cancer in Postmenopausal Women," Gynecologic Oncology, 2002, 85:388-390.
Ng et al., "Synthesis and SAR of potent and selective androgen receptor antagonist: 5,6-Dichloro-benzimidazole derivatives," Bioorganic & Medicinal Chemistry Letters 17, 2007, 17, 784-788.
Nicolaus et al., "Symbiotic Approach to Drug Design," Decision Making in Drug Research, 1983, pp. 173-186.
Norris et al., "Peptide Antagonists of the Human Estrogen Receptor," Science (1999) 285(5428):744-6.
Obinata et al., "Stereodivergent Construction of Aminodiols with a CF3 Group," Organic Letters, 2010, vol. 12, No. 19, 4316-4319.
Ohkura et al., "Evaluation of Estrogen Treatment in Female Patients with Dementia of the Alzheimer Type," Endocrine Journal, 1994, 41(4):361-371.
O'Leary et al., "Treating cancer with selective CDK4/6 inhibitors," Nature Reviews Clinical Oncology, 2016, 13, 417-430.
Oregan et al., "The evolution of tamoxifen therapy in breast cancer: selective oestrogen-receptor modulators and downregulators," LancetOnco/2002;3:207-14.
Orlando et al., "Molecularly targeted endocrine therapies for breast cancer," Cancer Treatment Reviews 3653 (2010) 567-571.
Ornoy et al., "Osteoporosis: Animal Models for the Human Disease," Animal Models of Human Related Calcium Metabolic Disorders, 1995, Chapter 5, 105-126.
Osborne et al., "Mechanisms of Endocrine Resistance in Breast Cancer," Annu. Rev. Med., 2011, 62:233-47.
Ostrowski et al., "Pharmacological and X-Ray Structural Characterization of a Novel Selective Androgen Receptor Modulator: Potent Hyperanabolic Stimulation of Skeletal Muscle with Hypostimulation of Prostate in Rats," Endocrinology, 2007, 148(1):4-12.
O'Sullivan, "CDK5/6 Inhibitors for the Treatment of Advanced Hormone Receptor Positive Breast Cancer and Beyond: 2016 Update," Expert Opinion on Pharmacotherapy, 2016, 37 pages.
O'Sullivan, "Overcoming Endocrine Resistance in Hormone-Receptor Positive Advanced Breast Cancer—The Emerging Role of CDK4/6 Inhibitors," Int J Cancer Clin Res., 2015, 2(4):17 pages.
Overmoyer et al., "Treatment With Adjuvant Endocrine Therapy for Early-Stage Breast Cancer: Is it Forever?," Journal of Clinical Oncology, 2015, 33(8):823-828.
Pallet et al., "Adverse events associated with mTOR inhibitors," Expert Opinion on Drug Safety, 2013, vol. 12, issue 2, 177-186.
Pancholi et al., "Impact of oral selective estrogen receptor degrader elacestrant (RAD1901) in models of endocrine sensitive/resistant breast cancer," In: Proceedings of the American Association for Cancer Research Annual Meeting 2017; Apr. 1-5, 2017; Washington, DC. Philadelphia (PA): AACR; Cancer Res, 2017, 77(13 Supplement): Abstract nr 4160.
Pandya et al., "Pilot study using gabapentin for tamoxifen-induced hot flashes in women with breast cancer," Breast Cancer Research and Treatment, 2004, 83:87-89.

(56) References Cited

OTHER PUBLICATIONS

Park et al., "Selective estrogen receptor modulators (SERMs) and their roles in breast cancer prevention," Trends in Molecular Medicine, 2002, 8(2):82-88.
Patani et al., "Differences in the Transcriptional Response to Fulvestrant and Oestrogen Deprivation in ER-Positive Breast Cancer," Clin Cancer Res, 2014, 20(15):3962-3973.
Pearce et al., "Psychological and sexual aspects of the menopause and HRT," Bailliere's Clinical Obstetrics and Gynaecology, 1996, 10(3):385-399.
Peng et al., "Potential of Selective Estrogen Receptor Modulators as Treatments and Preventives of Breast Cancer," Anticancer Agents Med Chem., 2009, 9(5):481-499.
Perey et al., "Clinical benefit of fulvestrant in postmenopausal women with advanced breast cancer and primary or acquired resistance to aromatase inhibitors: final results of phase II Swiss Group for Clinical Cancer Research Trial (SAKK 21/00)," Annals of Oncology, 2007, vol. 18, pp. 64-69.
Perez-Tenorio et al., "Activation of AKT/PKB in breast cancer predicts a worse outcome among endocrine treated patients," British Journal of Cancer, 2002, 86:540-545.
Phillips et al., "Muscle weakness in women occurs at an earlier age than in men, but strength is preserved by hormone replacement therapy," Clinical Science, 1993, 84:95-98.
Piu et al., "Pharmacological characterization of AC-262536, a novel selective androgen receptor modulator," Journal of Steroid Biochemistry & Molecular Biology, 2008, 109, 129-137.
Pors et al., Journal of Neuro-Oncology, vol. 10, pp. 173-177.
Prince et al., "Prevention of Postmenopausal Osteoporosis," The New England Journal of Medicine, 1991, vol. 325, No. 17, 7 pages.
Radius Health, "Radius Initiates Phase 2a Clinical Trial of RAD1901 in Menopausal Hot Flashes," (2009) Radius Health Press Release (2 pages).
Radius, "Radius Presents Positive Phase 2a Study Results Establishing Clinical Proof of Concept for RAD1901 in Reducing Menopausal Hot Flashes," (2010) Radius Press Release (2 pages).
Rao et al., "MicroRNA-221/222 confers breast cancer fulvestrant resistance by regulating multiple signaling pathways," Oncogene, 2011, 30(9): 1082-1097.
Rastelli et al., "Factors predictive of response to hormone therapy in breast cancer," Tumori, 2008, 94:370-383.
Reddy et al., "Synthesis of Indazolo[2, 3-a]quinoles," Indian Journal of Chemistry, 1988, vol. 27B, pp. 563-564.
Reinert et al., "Optimal Management of hormone receptor positive metastatic breast cancer in 2016," Ther Adv Med Oncol, 2015, 7(6):304-320.
Riedmaier et al., "Influence of testosterone and a novel SARM on gene expression in whole blood of *Macaca fascicularis*," Journal of Steroid Biochemistry and Molecular Biology, 2009, 114, 167-173.
Robertson et al., "A Good Drug Made Better: The Fulvestrant Dose-Response Story," Clinical Breast Cancer, 2014, 14(6):381-389.
Robertson et al., "A randomized trial to assess the biological activity of short-term (pre-surgical) fulvestrant 500 mg plus anastrozole versus fulvestrant 500 mg alone or anastrozole alone on primary breast cancer," Breast Cancer Research, 2013, 15:R18.
Robertson, "Estrogen Receptor Downregulators: New Antihormonal Therapy for Advanced Breast Cancer," Clinical Therapeutics, 2002, vol. 24, Suppl. A, A17-A30.
Robertson, "Selective oestrogen receptor modulators/new antioestrogens: aclinical perspective," Cancer Treatment Reviews, 2004, 30:695-706.
Robinson et al., "Activating ESR1 mutations in hormone-resistant metastatic breast cancer," Nat Genet., 2013, 45(12):1446-1451.
Rugo et al., "Endocrine Therapy for Hormone Receptor-Positive Metastatic Breast Cancer: American Society of Clinical Oncology Guideline," Journal of Clinical Oncology, 2016, 34(25):3069-3103.
Saal et al., "Poor prognosis in carcinoma is associated with a gene expression signature of aberrant PTEN tumor suppressor pathway activity," PNAS, 2007, pp. 7564-7569.

Salvati et al., "Identification and optimization of a novel series of [2.2.1]-oxabicyclo imide-based androgen receptor antagonist," Bioorganic & Medicinal Chemistry Letters, 2008, 1910-1915.
Sansone et al., "Self-renewal of CD133$^{hi}$ cells by IL6/Notch3 signalling regulates endocrine resistance in metastatic breast cancer," Nature Communications, 2016, 7:10442, 10 pages.
Santa-Maria et al., "Changing Treatment Paradigms in Metastatic Breast Cancer Lessons Learned," JAMA Oncol., 2015, 1(4):528-534.
Schäfer et al., "Failure is an option: learning from unsuccessful proof-of-concept trials," Drug Discovery Today, 2008, vol. 13, No. 21/22, 913-916.
Selli et al., "Accurate prediction of response to endocrine therapy in breast cancer patients: current and future biomarkers," Breast Cancer Research, 2016, 18:118, 10 pages.
Shang et al., "Cofactor Dynamics and Sufficiency in Estrogen Receptor-Regulated Transcription," Cell, 2000, 103:843-852.
Sharp et al., "Synthetic Connections to the Aromatic Directed Metalation Reaction. Functionalized Aryl Boronic Acids by Ipso Borodesilylation. General Synthesis of Unsymmetrical Biphenyls and m-Terphenyls," Tetrahedron Letters, 1987, 28(43):5093-5096.
Sherwin et al., "Estrogen and/or Androgen Replacement Therapy and Cognitive Functioning in Surgically Menopausal Women," Psychoneuroendocrinology, 1988, 13(4):345-357.
Spoerke et al., "Heterogeneity and clinical significance of ESR1 mutations in ER-positive metastatic breast cancer patients receiving fulvestrant," Nature Communications, 2016, 7:11579.
Stearns et al., "A pilot trial assessing the efficacy of paroxetine hydrochloride (Paxil) in controlling hot flashes in breast cancer survivors," Annals of Oncology, 2000, 11:17-22.
Sun et al., "Discovery of Potent, Orally-Active, and Muscle-Selective Androgen Receptor Modulators Based on an N-Aryl-hydroxybicyclohydantoin Scaffold," J. Med. Chem., 2006, 49, 7596-7599.
Sundar et al., "Spironolactone, a possible selective androgen receptor modulator, should be used with caution in patients with metastatic carcinoma of the prostate," BJM Case Rep, 2012, Abstract.
Swaby et al., "SERMs for the treatment and prevention of breast cancer," Rec Endocr Metab Disord, 2007, 8:229-239.
Thangavel et al., "Therapeutically activating RB: reestablishing cell cycle control in endocrine therapy-resistant breast cancer," Endocr Relat Cancer, 2011, 18(3):333-345.
Thiel, "Structure-aided drug design's next generation," Nature Biotechnology, 2004, vol. 22, No. 5, 513-519.
Toy et al., "ESR1 ligand-binding domain mutations in hormone-resistant breast cancer," Nature Genetics, 2013, 45(12):1439-1447.
Traboulsi et al., "Antiestrogens: Structure Activity Relationships and Use in Breast Cancer Treatment," J Mol Endocrinol, 2016, 41 pages.
Trinh et al., "A phase II study of the combination of endocrine treatment and bortezomib in patients with endocrine-resistant metastatic breast cancer," Oncology Reports, 2012, 27:657-663.
Tryfonidis et al., "Endocrine treatment in breast cancer: Cure, resistance and beyond," Cancer Treatment Reviews, 2016, 50:68-81.
Tsai et al., "Comparative Effects of Teriparatide, Denosumab, and Combination Therapy on Peripheral Compartmental Bone Density and Microarchitecture: the DATA-HRpQCT Study," ASBMR 2013 Annual Meeting, 2013, 3 pages.
Tucker et al., "Nonsteroidal Antiandrogens. Synthesis and Structures-Activity Relationships of 3-Substituted Derivatives of 2-Hydroxypropionanilides," J. Med. Chem., 1988, 31, 954-959.
U.S. Department of Health and Human Services, "Bone Health and Osteoporosis. A Report of the Surgeon General," 2004.
Vajda et al., "Pharmacokinetics and Pharmacodynamics of LGD-3303 [9-Chloro-2-ethyl-1-methyl-3-(2,2,2-trifluoroethyl)-3H-pyrrolo-[3,2-f]quinolin-7(6H)-one], an Orally Available Nonsteroidal-Selective Androgen Receptor Modulator," The Journal of Pharmacology and Experimental Therapeutics, 2009, vol. 328, No. 2, 663-670.
Van Kruchten et al., "Measuring Residual Estrogen Receptor Availability during Fulvestrant Therapy in Patients with Metastatic Breast Cancer," Cancer Discovery, 2015, 5:72-81.

(56) References Cited

OTHER PUBLICATIONS

Van Oeveren et al., "Novel selective androgen receptor modulators: SAR studies on 6-bisalkylamino-2-quinolinones," Bioorganic & Medicinal Chemistry Letters, 2007, 17:1527-1531.
Venkatesh et al., "Role of the Development Scientist in Compound Lead Selection and Optimization," J. Pharm. Sci., 2000, 89(2):145-154.
Vergote et al., "Fulvestrant, a new treatment option for advanced breast cancer: tolerability versus existing agents," Annals of Oncology, 2006, 17:200-204.
Vesuna et al., "Twist contributes to hormone resistance in breast cancer by down-regulating estrogen receptor alpha," Oncogene, 2012, 31(27):3223-3234.
Viedma-Rodriguez et al., "Mechanisms associated with resistance to tamoxifen in estrogen receptor-positive breast cancer (Review)," Oncology reports, 2014, 32:3-15.
Vinayak et al., "mTOR Inhibitors in the Treatment of Breast Cancer," Cancer Network, <http://www.cancernetwork.com/breast-cancer/mtor-inhibitors-treatment-breast-cancer>, 2013.
Vora et al., "CDK 4/6 inhibitors sensitize PIK3CA Mutant Breast Cancer to PI3K inhibitors," Cancer Cell, 2014, 26(1):136-149.
Vranic et al., "ER-α, a novel isoform of ER-α66, is commonly over-expressed in apocrine and adenoid cystic carcinomas of the breast," J Clin Pathol, 2011, 64(1):54-57.
Walsh et al., "Effects of Raloxifene on Serum Lipids and Coagulation Factors in Healthy Postmenopausal Women," JAMA, 1998, 279(18):1445-1451.
Walsh et al., "The Effects of Hormone Replacement Therapy and Raloxifene on C-Reactive Protein and Homocysteine in Healthy Postmenopausal Women: A Randomized, Controlled Trial," The Journal of Clinical Endocrinology & Metabolism, 2000, 85(1):214-218.
Wang et al., "Anti-Inflammatory Properties and Regulatory Mechanism of a Novel Derivative of Artemisinin in Experimental Autoimmune Encephalomyelitis," The Journal of Immunology, 2007, 179:5958-5965.
Wardell et al., "Bazedoxifene Exhibits Antiestrogenic Activity in Animal Models of Tamoxifen-Resistant Breast Cancer: Implications for Treatment of Advanced Disease," (2013) Clin Cancer Res 19 (9): 2420-2431.
Wardell et al., "Efficacy of SERD/SERM Hybrid-CDK4/6 inhibitor combinations in models of endocrine therapy resistant breast cancer," American Association for Cancer Research, 2015, 33 pages.
Wardell et al., "Research Resource: Transcriptional Profiling in a Cellular Model of Breast Cancer Reveals Functional and Mechanistic Differences Between Clinically Relevant SERM and Between SERM/Estrogen Complexes," (2012) Mol Endocrinol 26 (7):1235-1248.
Wardell et al., "The turnover of estrogen receptor a by the selective estrogen receptor degrader (SERD) fulvestrant is a saturable process that is not required for antagonist efficacy," (2011) Biochem Pharmacol 82 (2):122-130.
Weir et al., "AZD9496: An oral estrogen receptor inhibitor that blocks the growth of ER-positive and ESR1 mutant breast tumours in preclinical models," AACR, 2016, 35 pages.
Westbrook et al., "Pharmacogenomics of breast cancer therapy: An update," Pharmacology & Therapeutics, 2013, 13:1-11.
Wittig et al., "Dehydrobenzol und N-Methyl-pyrrol," Chemische Berichte., 1958, 91 (11):2358-2365.
Wittmann et al., "Definition of Functionally Important Mechanistic Differences among Selective Estrogen Receptor Down-regulators," (2007) Cancer Res 67 (19):9549-9560.
Wu and Wu, "Receptor-mediated in Vitro Gene Transformation by a Soluble DNA Carrier System," J. Biol. Chem. (1987) 262:4429-4432.
Xiao et al., "Identification of preclinical mechanisms driving acquired resistance to selective ERα degraders (SERDs), CDK4/6 inhibitors, or to combinations of both agents," Poster No. P3-04-24, SABCS 2016.

Yardley et al., "Everolimus Plus Exemestane in Postmenopausal Patients with HR+ Breast Cancer: BOLERO-2 Final Progression-Free Survival Analysis," Adv Ther, 2013, 30:870-884.
Yardley, "Combining mTOR Inhibitors with Chemotherapy and Other Targeted Therapies in Advanced Breast Cancer: Rationale, Clinical Experience, and Future Directions," Breast Cancer, 2013, 7:7-22.
Yasui et al., "Tumor growth and metastasis of human colorectal cancer cell lines in SCID mice resemble clinical metastatic behaviors," Invasion Metastasis, 1997, 17, 259-269.
Yi et al., "Which threshold for ER positivity? A retrospective study based on 9639 patients," Annals of Oncology, 2014, 25:1004-1011.
Yoon et al., "Gene expression profiling identifies responsive patients with cancer of unknown primary treated with carboplatin, paclitaxel, and everolimus: NCCTG N0871 (alliance)," Ann Oncol., 2016, 27(2):339-344.
Young et al., "Treatment of ESR1 mutant and PIK3CA mutant patient-derived breast cancer xenograft models reveals differential anti-tumor responses to estrogen receptor degraders and PI3K inhibitors in vivo," Poster No. P4-06-05, SABCS 2016.
Zeng et al., "Efficient synthesis of (2R,3S)-2-amino-3-(benzyloxy)-4,4,4-trifluorobutanoic acid (4,4,4-trifluoro-OBn-D-allothreonine)," Tetrahedron Letters, 2010, vol. 51, Issue 41, 5361-5363.
Zhang et al., "An estrogen receptor mutant with strong hormone-independent activity from a metastatic breast cancer," Cancer Research, 1997, 57(7): 1244-9.
Zhang et al., "Elevated insulin-like growth factor 1 receptor signaling induces antiestrogen resistance through the MAPK/ERK and PI3K/Akt signaling routes," Breast Cancer Research, 2011, 12:R52.
Zhang et al., "Synthesis and SAR of novel hydantoin derivatives as selective androgen receptor modulators," Bioorganic & Medicinal Chemistry Letters, 2006, vol. 16, Issue 22, 5763-5766.
International Search Report and Written Opinion for Application No. PCT/US2015/023216 dated Jun. 24, 2015 (12 pages).
International Search Report for Application No. PCT/EP1996/001962 dated Sep. 16, 1996 (3 pages).
International Search Report for Application No. PCT/US1997/022498 dated Dec. 23, 1998 (6 pages).
International Search Report for Application No. PCT/US2006/044921 dated Mar. 15, 2007 (3 pages).
International Search Report and Written Opinion for Application No. PCT/US2007/014598 dated Mar. 28, 2008 (12 pages).
International Search Report and Written Opinion for Application No. PCT/US2009/001035 dated Aug. 7, 2009 (11 pages).
International Search Report and Written Opinion for Application No. PCT/US2009/002885 dated Sep. 10, 2009 (15 pages).
International Search Report and Written Opinion for Application No. PCT/US2009/054348 dated Dec. 9, 2009 (8 pages).
International Search Report and Written Opinion for Application No. PCT/US2010/030480 dated Jun. 9, 2010 (7 pages).
International Search Report and Written Opinion for Application No. PCT/US2011/023768 dated Mar. 25, 2011 (8 pages).
International Search Report for Application No. PCT/US2011/063034 dated Mar. 19, 2012 (6 pages).
International Search Report and Written Opinion for Application No. PCT/US2012/034510 dated Aug. 31, 2012 (8 pages).
International Search Report and Written Opinion for Application No. PCT/US2011/036311 dated Aug. 12, 2011 (10 pages).
International Search Report and Written Opinion for Application No. PCT/US2016/030316 dated Aug. 4, 2016 (10 pages).
International Search Report and Written Opinion for Application No. PCT/US2016/030317 dated Aug. 4, 2016 (7 pages).
International Search Report and Written Opinion for Application No. PCT/US2016/030321 dated Aug. 4, 2016 (10 pages).
International Search Report and Written Opinion for Application No. PCT/US2017/053834 dated Nov. 20, 2017 (9 pages).
Canadian Patent Office Action for Application No. 2,943,611 dated Apr. 13, 2021 (5 pages).
European Patent Office Extended Search Report for Application No. 15769394.6 dated Nov. 2, 2017 (8 pages).
European Patent Office Extended Search Report for Application No. 15769394.6 dated Nov. 29, 2019 (4 pages).

(56) References Cited

OTHER PUBLICATIONS

European Patent Office Extended Search Report for Application No. 21151737.0 dated Apr. 23, 2021 (12 pages).
European Patent Office Action for Application No. 15769394.6 dated May 31, 2021 (5 pages).
United States Patent Office Action for U.S. Appl. No. 14/512,061 dated Feb. 5, 2015 (10 pages).
United States Patent Office Action for U.S. Appl. No. 15/214,187 dated Dec. 28, 2016 (16 pages).
United States Patent Office Final Action for U.S. Appl. No. 14/512,061 dated Sep. 1, 2015 (14 pages).
United States Patent Office Notice of Allowance for U.S. Appl. No. 14/512,061 dated Jun. 14, 2016 (12 pages).
United States Patent Office Action for U.S. Appl. No. 15/214,187 dated Jan. 23, 2018 (14 pages).
United States Patent Office Action for U.S. Appl. No. 15/129,197 dated Aug. 10, 2018 (13 pages).
United States Patent Office Action for U.S. Appl. No. 16/041,416 dated Dec. 31, 2018 (15 pages).
United States Patent Office Action for U.S. Appl. No. 15/129,197 dated Jan. 8, 2019 (11 pages).
United States Patent Office Notice of Allowance for U.S. Appl. No. 15/129,197 dated May 13, 2019 (10 pages).
United States Patent Office Action for U.S. Appl. No. 16/041,416 dated Aug. 19, 2019 (10 pages).
United States Patent Office Action for U.S. Appl. No. 16/721,329 dated Feb. 7, 2020 (20 pages).
United States Patent Office Action for U.S. Appl. No. 16/549,828 dated Jun. 23, 2021 (23 pages).
United States Patent Office Action for U.S. Appl. No. 16/986,492 dated Mar. 16, 2022 (20 pages).
Wong et al., "The development, application and limitations of breast cancer cell lines to study tamoxifen and aromatase inhibitor resistance," Journal of Steroid Biochemistry & Molecular Biology, 2011, 131(3): 83-92.
Hiscox et al., "Aromatase inhibitors in breast cancer," Maturitas, 2009, 63(4): 275-279.
European Patent Office Extended Search Report for Application No. 21215140.1 dated Oct. 28, 2022 (13 pages).

METHOD OF TREATING CANCER USING SELECTIVE ESTROGEN RECEPTOR MODULATORS

CROSS REFERENCE TO RELATED APPLICATIONS

This patent application is a continuation U.S. patent application Ser. No. 16/549,828, filed Aug. 23, 2019, which is a continuation of U.S. patent application Ser. No. 15/129, 197, filed Sep. 26, 2016, issued Sep. 24, 2019 as U.S. Pat. No. 10,420,734, which is the national stage filing under 35 U.S.C. § 371 of International Application No. PCT/US2015/023216, filed on Mar. 28, 2015, which application claims priority to U.S. Provisional Application No. 62/129,379, filed Mar. 6, 2015, and is a continuation-in-part of U.S. patent application Ser. No. 14/512,061, filed Oct. 10, 2014, issued as U.S. Pat. No. 9,421,264, on Aug. 23, 2016, which application claims priority to U.S. Provisional Application No. 61/971,627, filed Mar. 28, 2014, the entire contents of each of which are hereby incorporated by reference.

STATEMENT OF GOVERNMENT INTEREST

This invention was made with government support under R37DK048807 awarded by the National Institutes of Health. The government has certain rights in the invention.

TECHNICAL FIELD

The present invention relates to methods of treating subjects suffering from estrogen receptor positive cancer of the brain by administering a selective estrogen receptor modulator (SERM) to the subject. The present invention also relates to methods of treating subjects suffering from a cancer that is resistant to an estrogen receptor modulator by administering a SERM to the subject.

BACKGROUND

The estrogen receptor (ER) is a ligand dependent transcription factor whose expression confers upon target cells the ability to respond to estrogens. In the absence of an activating ligand, ER resides in the cell in an inactive form within a large inhibitory protein complex. Upon binding ligand, however, the receptor undergoes an activating conformational change resulting in its release from the inhibitory protein complex, spontaneous dimerization and subsequent interaction with enhancers located within target genes. Depending on the promoter context of the bound receptor, and the co factors that are recruited to the receptor in a particular cell, it can either positively or negatively regulate target gene transcription. Thus, the same ER-ligand complex can have very different activities in different cells, an observation that explains how estrogens, generally considered to be reproductive hormones, exhibit activities in bone, the cardiovascular system and in brain that are unrelated to reproductive function.

Whereas the molecular determinants of ER action differ considerably between target cells, it has been anticipated that the exploitation of this complexity will yield pharmaceuticals with process or tissue selective activities. The first evidence in support of this hypothesis came from studies that probed the pharmacological activities of the 'antiestrogen' tamoxifen. Identified as a high affinity antagonist of ER and developed as a treatment for ER-positive breast cancer, it soon became apparent that whereas tamoxifen could oppose estrogen action in the breast it exhibited agonist activity in the bone, uterus and in the cardiovascular system. Reflecting this spectrum of activities, tamoxifen was reclassified as a Selective Estrogen Receptor Modulator (SERM).

Breast cancer remains the most commonly diagnosed cancer among women and a leading cause of cancer mortality. While targeted therapies such as the SERM tamoxifen and aromatase inhibitors are initially effective in the treatment of estrogen receptor alpha (ESR1) positive tumors, de novo and acquired resistance remain an impediment to durable clinical responses, particularly in the setting of advanced disease. ESR1 is a therapeutic target in breast cancers that are resistant to both first and second line endocrine interventions, a finding that has prompted the development of (a) SERMs with a mechanism distinct from tamoxifen and (b) selective estrogen receptor degraders (SERDs), competitive antagonists whose interaction with ESR1 induce its proteasome dependent degradation. Fulvestrant, a SERD, has been effective as both a first- and second-line therapy in advanced breast cancer; however, the pharmaceutical properties of this drug may prove dose-limiting in relapsed/resistant breast tumors bearing ESR1 mutations known to decrease SERD potency. The clinical efficacy of fulvestrant, a Selective Estrogen Receptor Degrader (SERD) that triggers receptor degradation, has confirmed that ESR1 often remains engaged in endocrine therapy resistant cancers.

The increasing incidence of breast cancer brain metastases (BCBM) is an emerging challenge in the treatment of advanced breast cancer patients. The growing success of improved treatments of systemic disease has allowed the manifestation of BCBM that previously would not have impacted the morbidity and mortality associated with breast cancer. The privileged environment of the brain, maintained by the relatively non-porous blood brain barrier, presents a significant impediment to the successful targeting of BCBM, leading to the use of gamma knife surgery and/or whole brain radiation in an attempt to shrink or ablate brain lesions. The benefit of these treatments must be carefully balanced with neurological deficit as a result of treatment.

Although considerable advances have been made in targeting the estrogen signaling axis for the treatment of breast cancer and osteoporosis, similar progress has unfortunately not yet been accomplished in the development of safe and effective treatments for the climacteric conditions or vasomotor disturbances that are associated with estrogen deprivation. There is considerable interest in developing novel SERMs that can be used to treat vasomotor symptoms but which do not exhibit mitogenic activities in the breast or the uterus.

While tamoxifen and aromatase inhibitors have proven effective in the treatment of estrogen receptor positive (ER+) breast cancer, the incidence of resistance remains significant, particularly in the advanced/metastatic breast cancer setting. An additional class of estrogen receptor targeting therapy, selective estrogen receptor degraders (SERDs), has recently come to prominence. These agents have proven effective in pre-clinical models of breast cancers that are resistant to tamoxifen or aromatase inhibitors, leading to their evaluation in clinical trials. However, these agents also do not readily pass the blood brain barrier, suggesting that they will be ineffective in targeting BCBM. It would be beneficial to have other treatment options that can penetrate the blood brain barrier and/or selectively target tissue specific activities responsive to ER activation.

SUMMARY

The present invention is directed to a method of treating estrogen receptor positive cancers of the brain in a subject.

The method comprises administering a compound represented by the following formula I:

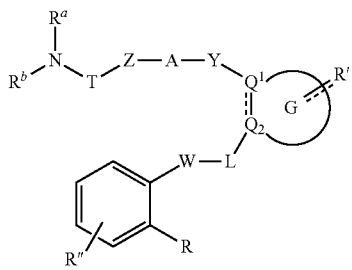
(I)

wherein

TZ represents a $C_1$-$C_4$ alkylene group or —CR$^{f'}$R$^{g'}$—CH$_2$—O— wherein R$^{f'}$ and R$^{g'}$ independently represent hydrogen or a C1-C6 alkyl group;

A represents a 5- to 14-membered heteroarylene group which may have a substituent or a $C_6$-$C_{14}$ arylene group which may have a substituent;

Y represents —CH$_2$—NR$^c$— wherein R$^c$ represents hydrogen or a $C_1$-$C_6$ alkyl group which may have a substituent;

ring G represents the following formula:

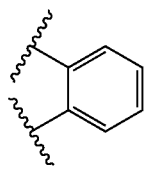 [SMILES: *c1ccccc1*]

R' represents 1 to 4 substituents independently selected from a hydrogen atom, a $C_1$-$C_6$ alkoxy group, and a hydroxyl group;

a partial structure in formula (I) represented by the following formula:

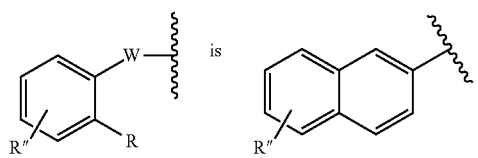

R" represents hydrogen, a hydroxyl group that may be further protected by a protecting group or a $C_1$-$C_6$ alkoxy group which may have a substituent; and R$^a$ and R$^b$ are the same as or different from each other and each represents a hydrogen atom, a $C_1$-$C_6$ alkyl group which may have a substituent, or a $C_3$-$C_8$ cycloalkyl group which may have a substituent, or when R$^a$ and R$^b$ are bonded together, they may form, together with the nitrogen atom that is adjacent to R$^a$ and R$^b$, a 4- to 10-membered single ring which may have a substituent; and L represents a single bond, or a salt thereof.

The cancer may be Breast cancer brain metastases, Astrocytoma, Atypical Teratoid Rhabdoid Tumor (ATRT), Chondrosarcoma, Choroid Plexus Carcinoma, Craniopharyngioma, Ependymoma, Germ Cell Tumor, Glioblastoma, Glioma, Hemangioma, Juvenile Pilocytic Astrocytoma, Medulloblastoma, Meningioma, Neurofibroma, Neuronal and Mixed Neuronal-Glial Tumors, Oligoastrocytoma, Oligodendroglioma, Pineal Tumor, Pituitary Tumor, PNET—(primitive neuroectodermal tumor), Schwannoma, and Leptomeningeal metastases. Ra and Rb independently may represent a hydrogen atom, a methyl group, an ethyl group, a n-propyl group, an iso-propyl group, a n-butyl group, an iso-butyl group, or a tert-butyl group. -T-Z— may represents —CH$_2$CH$_2$— or —C(CH$_3$)$_2$CH$_2$O—. Y may represent —CH$_2$—N(CH$_2$CH$_3$)— or —CH$_2$—N(CH$_2$CH$_2$OH)—. Each of R" independently may represents a hydrogen atom or a methoxy group. R" may represents a hydroxyl group. A may represents a phenylene group. The compound may be (R)-6-{2-{ethyl[4-(2-ethylaminoethyl)benzyl]amino}-4-methoxyphenyl}-5,6,7,8-tetrahydronaphthalen-2-ol. An effective amount of the compound may be administered. The effective amount may comprise a high dosage. The high dosage may be more than about 20 mg/kg. The high dosage may be about 20 mg/kg to about 100 mg/kg. The compound may be administered by oral administration, intravenous administration, intradermal injection, intramuscular injection, or subcutaneous injection. The method may further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

The present invention is directed to a method of treating breast cancer brain metastasis in a subject. The method comprises administering a compound represented by the following formula I:

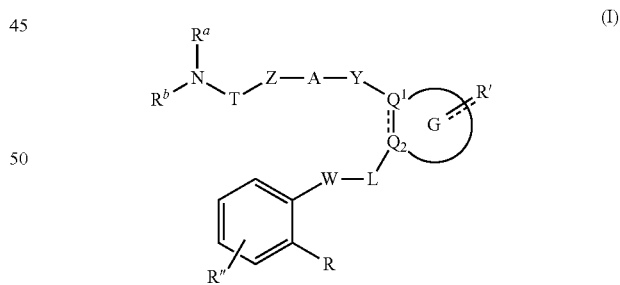
(I)

wherein

TZ represents a $C_1$-$C_4$ alkylene group or —CR$^{f'}$R$^{g'}$—CH$_2$—O— wherein R$^{f'}$ and R$^{g'}$ independently represent hydrogen or a $C_1$-$C_6$ alkyl group;

A represents a 5- to 14-membered heteroarylene group which may have a substituent or a $C_6$-$C_{14}$ arylene group which may have a substituent;

Y represents —CH$_2$—NR$^c$— wherein R$^c$ represents hydrogen or a $C_1$-$C_6$ alkyl group which may have a substituent;

ring G represents the following formula:

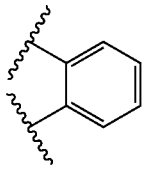 [SMILES: *c1ccccc1*]

R' represents 1 to 4 substituents independently selected from a hydrogen atom, a $C_1$-$C_6$ alkoxy group, and a hydroxyl group;

a partial structure in formula (I) represented by the following formula:

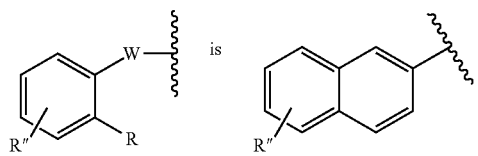

R" represents hydrogen, a hydroxyl group that may be further protected by a protecting group or a $C_1$-$C_6$ alkoxy group which may have a substituent; and $R^a$ and $R^b$ are the same as or different from each other and each represents a hydrogen atom, a $C_1$-$C_6$ alkyl group which may have a substituent, or a $C_3$-$C_8$ cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and L represents a single bond, or a salt thereof.

$R^a$ and $R^b$ independently may represent a hydrogen atom, a methyl group, an ethyl group, a n-propyl group, an iso-propyl group, a n-butyl group, an iso-butyl group, or a tert-butyl group. -T-Z— may represents —$CH_2CH_2$— or —$C(CH_3)_2CH_2O$—. Y may represent —$CH_2$—N($CH_2CH_3$)— or —$CH_2$—N($CH_2CH_2OH$)—. Each of R" independently may represents a hydrogen atom or a methoxy group. R" may represents a hydroxyl group. A may represents a phenylene group. The compound may be (R)-6-{2-{ethyl[4-(2-ethylaminoethyl)benzyl]amino}-4-methoxyphenyl}-5,6,7,8-tetrahydronaphthalen-2-ol. An effective amount of the compound may be administered. The effective amount may comprise a high dosage. The high dosage may be more than about 20 mg/kg. The high dosage may be about 20 mg/kg to about 100 mg/kg. The compound may be administered by oral administration, intravenous administration, intradermal injection, intramuscular injection, or subcutaneous injection. The method may further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

The present invention is directed to a method of treating a cancer in a subject, wherein the cancer is resistant to an estrogen receptor modulator. The method comprises administering a compound represented by the following formula I:

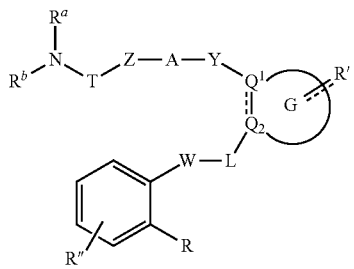

wherein

TZ represents a $C_1$-$C_4$ alkylene group or —$CR^{f'}R^{g'}$—$CH_2$—O— wherein $R^{f'}$ and $R^{g'}$ independently represent hydrogen or a $C_1$-$C_6$ alkyl group;

A represents a 5- to 14-membered heteroarylene group which may have a substituent or a $C_6$-$C_{14}$ arylene group which may have a substituent;

Y represents —$CH_2$—$NR^c$— wherein $R^c$ represents hydrogen or a $C_1$-$C_6$ alkyl group which may have a substituent;

ring G represents the following formula:

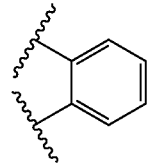 [SMILES: *c1ccccc1*]

R' represents 1 to 4 substituents independently selected from a hydrogen atom, a $C_1$-$C_6$ alkoxy group, and a hydroxyl group;

a partial structure in formula (I) represented by the following formula:

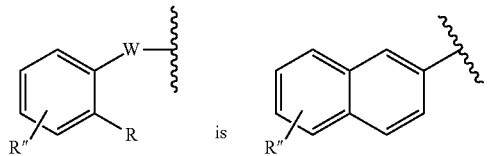

R" represents hydrogen, a hydroxyl group that may be further protected by a protecting group or a $C_1$-$C_6$ alkoxy group which may have a substituent; and $R^a$ and $R^b$ are the same as or different from each other and each represents a hydrogen atom, a $C_1$-$C_6$ alkyl group which may have a substituent, or a $C_3$-$C_8$ cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and L represents a single bond, or a salt thereof.

The cancer may be de novo resistant to the estrogen receptor modulator. The resistance to the estrogen receptor modulator may be acquired. The estrogen receptor modulator may be a selective estrogen receptor modulator (SERM). The SERM may be tamoxifen, idoxifene, raloxifene or ICI 182,780. The cancer may be breast, endometrial or ovarian cancer. The cancer may be breast cancer. $R^a$ and $R^b$ independently may represent a hydrogen atom, a methyl group, an ethyl group, a n-propyl group, an iso-propyl group, a n-butyl group, an iso-butyl group, or a tert-butyl group. -T-Z— may represents —$CH_2CH_2$— or —$C(CH_3)_2CH_2O$—. Y may represent —$CH_2$—N($CH_2CH_3$)— or —$CH_2$—N($CH_2CH_2OH$)—. Each of R" independently may represents a hydrogen atom or a methoxy group. R''' may represents a hydroxyl group. A may represents a phenylene group. The compound may be (R)-6-{2-{ethyl[4-(2-ethylaminoethyl)benzyl]amino}-4-methoxyphenyl}-5,6,7,8-tetrahydronaphthalen-2-ol. An effective amount of the compound may be administered. The effective amount may comprise a high dosage. The high dosage may be more than about 20 mg/kg. The high dosage may be about 20 mg/kg to about 100 mg/kg. The compound may be administered by oral administration, intravenous administration, intradermal injection, intramuscular injection, or subcutaneous injection. The method may further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows MCF7 breast cancer cells were treated 4 hours as indicated prior to western blot detection of ER and loading control cytokeratin (CK) 18. FIG. 1B shows ovariectomized mice bearing MCF7 xenograft tumors were treated daily with RAD1901 ("RAD") or tamoxifen ("Tam") in the context of continued estrogen treatment.

FIG. 2A shows ERα protein expression in whole cell extracts pre-treated with transcription or translation inhibitors before treatment with RAD1901, analyzed by immunoblot. FIG. 2B shows ERα mRNA expression in similarly treated cells.

DETAILED DESCRIPTION

Figures 1A, 1B:
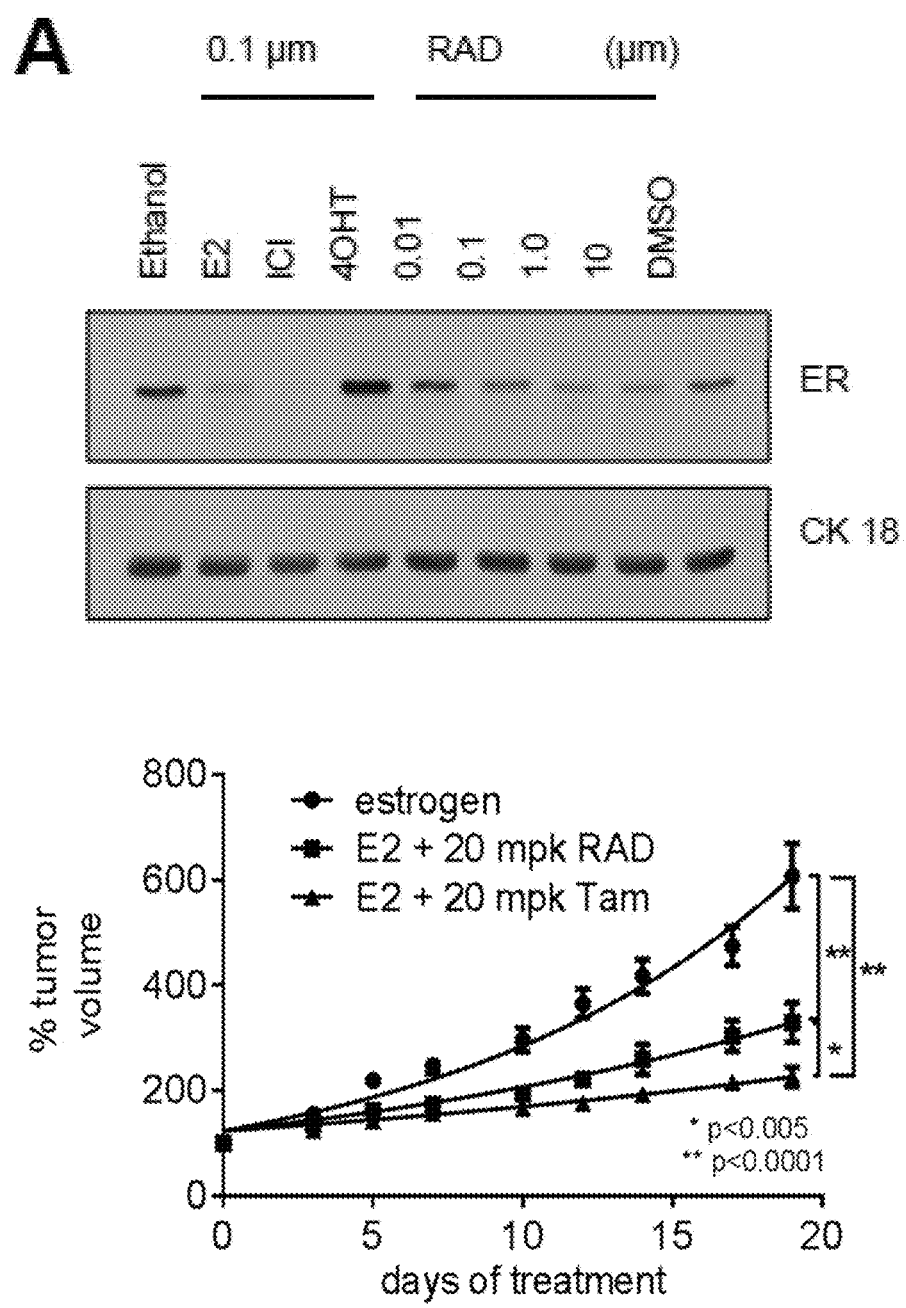
FIGS. 1A-1B show treatment with (R)-6-{2-{ethyl[4-(2-ethylaminoethyl)benzyl]amino}-4-methoxyphenyl}-5,6,7,8-tetrahydronaphthalen-2-ol ("RAD1901") results in a dose dependent reduction in ER expression and activity.

The present disclosure provides a method of treating a subject suffering from estrogen receptor positive cancer of the brain, such as BCBM, or a cancer that is resistant to an estrogen receptor modulator, such as tamoxifen resistant breast cancer. The methods involve administering to the subject a SERM, such as RAD1901. RAD1901 is a SERM/SERD hybrid that exhibits complex and unique pharmacology in breast cancer models, having dose-dependent agonist/antagonist activity displayed in a tissue-selective manner. RAD1901 exhibits desired pharmacological activities and exhibits significant brain penetrance when evaluated in postmenopausal women, in particular a unique dose response, with lower doses of the drug being more effective at relieving hot flashes. RAD1901 induces hot flashes in healthy postmenopausal women in a dose dependent manner, thus RAD1901 may effectively inhibit estrogen receptor action in the brain.

Turnover of ERα is significantly increased upon binding RAD1901, an activity that is more pronounced at higher drug concentrations (FIG. 1). This drug exhibits some of the characteristics that are generally attributed to selective estrogen receptor degraders (SERDs). Thus, at lower doses RAD1901 exhibits partial agonist activity, i.e., SERM activity, allowing for relief of hot flashes, but the SERD activity of the compound dominates when the receptor is exposed to higher concentrations. The present disclosure describes in vitro the mechanism by which RAD1901 impacts ER expression and investigates the possible result of such action in vivo.

As exemplified below, RAD1901 surprisingly has the ability to degrade the estrogen receptor. Both in vitro and in vivo studies have since shown that the antagonist activity of this ligand correlates with estrogen receptor degradation in a dose dependent manner. RAD1901 also inhibits estrogen dependent growth of breast cancer xenograft tumors and may be used to treat breast cancer, such as tamoxifen resistant breast cancer.

RAD1901 is unique among both SERMs and SERDs in that this drug accumulates in the brain, an environment in which SERM penetration has been historically regarded as quite low. Estrogen receptor activity has been found to be important in the growth of tumors resistant to aromatase inhibitors and/or tamoxifen, and treatment with SERDs has been shown to have clinical benefit. While the revelation that RAD1901 exhibits SERD activity certainly suggests potential utility in the treatment of progressing ER+ breast tumors, which was unappreciated prior to the present disclosure, the targeting of ER activity for the treatment of ER+ brain cancers represents a new frontier for the use of both SERMs and SERDs, as RAD1901 represents the first SERM/SERD that can sufficiently penetrate the brain to exhibit efficacy. Because BCBM is generally diagnosed late in the disease progression of ER+ metastatic breast cancer, patients will in general have already been treated with endocrine therapeutics (i.e. tamoxifen or aromatase inhibitors). Thus, while SERMs such as tamoxifen have low brain penetration and have exhibited efficacy in anecdotal cases of BCBM that are detailed in the literature, the SERD activity of RAD1901 becomes key to the therapeutic potential of this compound for treatment of BCBM, as SERDs have been found to be effective in breast cancers that are resistant to SERM or aromatase inhibitor therapy.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "administration" or "administering," as used herein refers to providing, contacting, and/or delivery of the SERM by any appropriate route to achieve the desired effect. These agents may be administered to a subject in numerous ways including, but not limited to, orally, ocularly, nasally, intravenously, topically, as aerosols, suppository, etc. and may be used in combination.

"Aromatase inhibitor" as used herein refers to a compound that targets aromatase, which is an enzyme involved in the biosynthesis of estrogen. Aromatase inhibitors may block the production of estrogen or block the action of estrogen on receptors.

"Blood brain barrier" or "BBB" as used herein refers to a highly selective permeability barrier that separates the circulating blood from the brain extracellular fluid in the central nervous system. The blood brain barrier may prevent the certain drugs from entering brain tissue and is a limiting factor in the delivery of many peripherally-administered agents to the central nervous system.

"Breast cancer" as used herein refers to a type of cancer that originates from and develops in the breast. "Metastatic breast cancer" refers to breast cancer that spreads outside the breast to the lymph nodes, bones, or other areas.

"Breast Cancer Brain Metastases" and "BCBM" as used interchangeably herein refer to breast cancer that has metastasized to the brain. BCBM may occur in up to 10-15% of breast-cancer patients. BCBM may progress rapidly and can produce life-threatening complications such as increased intracranial pressure, herniation of the brain and seizures. Radiotherapy is a treatment of BCBM as it halts tumor progression quickly and can induce a response in the majority of patients.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

The term "effective dosage" as used herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of the estrogen receptor. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the SERM may be administered at various times during the course of treatment of the subject. The times of administration and dosages used will depend on several factors, such as the goal of treatment (e.g., treating v. preventing), condition of the subject, etc. and can be readily determined by one skilled in the art.

"Estrogen dependent cancer" or "estrogen receptor positive cancer" as used interchangeably herein refers to a tumor that contains estrogen receptor (ER) positive cells, i.e., cells that have estrogen receptors, and respond to the presence of estrogen with increased proliferation. Estrogen dependent cancers may include breast cancer, ovarian cancer, or endometrial cancer. "Estrogen receptor positive breast cancer" is a type of breast cancer that is sensitive to estrogen.

"Estrogen receptor" or "ER" as used interchangeably herein refers to a receptor that is activated by the hormone estrogen and is a member of the nuclear hormone family of intracellular receptors. There are two different isoforms of estrogen receptor, referred to as α (also referred to as "ERa") and β (also referred to as "ERb"). ERa and ERb genes are encoded by ESR1 and ESR2 gene, respectively. Hormone-activated estrogen receptors form dimers and may form homodimers or heterodimers. Both ERs are widely expressed in different tissue types.

"Estrogen-receptor downregulators" as used herein refers to a drug or compound which binds and down-regulates the expression of an estrogen-receptor.

"Estrogen receptor negative breast cancer" or "Estrogen independent breast cancer" as used interchangeably herein refers to a tumor that does not contain estrogen receptor positive cells, i.e., cells that lack estrogen receptors, and does not depend on the presence of estrogen for ongoing proliferation.

"HER2 intervention drug" or "HER2 inhibitor" as used interchangeably herein refers to a compound that targets human Epidermal Growth Factor Receptor 2 (HER2). HER2 is a member of the epidermal growth factor receptor family and is involved in the development and progression of certain aggressive types of breast cancer, such as estrogen dependent breast cancer. A HER2 inhibitor may be a tyrosine kinase or a monoclonal antibody.

"Metastatic cancer" as used herein refers to a cancer that has spread from the part of the body where it started (the primary site) to other parts of the body.

"Progesterone receptor positive cancer" as used herein refers to a tumor that contains progesterone receptor positive (PR+) cells, i.e., cells that have progesterone receptors, which respond to the presence of progesterone with increased proliferation.

"Selective estrogen receptor degraders" or "SERDs" as used interchangeably herein refers to a compound that interacts with an ER and induce a conformational change that results in the degradation of the receptor.

"Selective estrogen receptor modulators" or "SERMs" as used interchangeably herein refers to a compound that interacts with an ER and whose relative agonist/antagonist activities are manifest in a cell selective manner. The prevention of estrogen binding to the estrogen receptor may lead to decreased proliferation of estrogen dependent cancer cells.

The term "subject", "patient" or "subject in the method" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus or rhesus monkey, chimpanzee, etc.) and a human).

In some embodiments, the subject or subject may be a human or a non-human. In some embodiments, the subject may be a human subject at risk for developing or already suffering from cancer.

"Tamoxifen resistant breast cancer" as used herein refers to a breast cancer that does respond to treatment with tamoxifen.

"Treat," "treating," or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of the SERM to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

2. Methods of Treating Cancer with a SERM

The present invention is directed to methods of treating a subject suffering from cancer. The methods include administering a compound, i.e., SERM, having formula I:

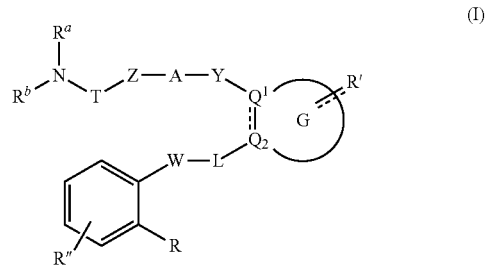

wherein
TZ represents a $C_1$-$C_4$ alkylene group or —$CR^{f'}R^{g'}$—$CH_2$—O— wherein $R^{f'}$ and $R^{g'}$ independently represent hydrogen or a $C_1$-$C_6$ alkyl group;
A represents a 5- to 14-membered heteroarylene group which may have a substituent or a $C_6$-$C_{14}$ arylene group which may have a substituent;
Y represents —$CH_2$—$NR^c$— wherein $R^c$ represents hydrogen or a $C_1$-$C_6$ alkyl group which may have a substituent;
ring G represents the following formula:

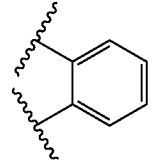 [SMILES: *c1ccccc1*]

R' represents 1 to 4 substituents independently selected from a hydrogen atom, a $C_1$-$C_6$ alkoxy group, and a hydroxyl group;
a partial structure in formula (I) represented by the following formula:

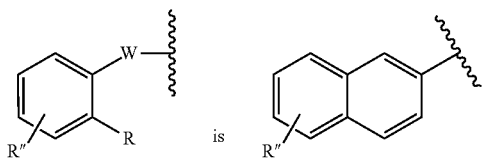

R" represents hydrogen, a hydroxyl group that may be further protected by a protecting group or a $C_1$-$C_6$ alkoxy group which may have a substituent; and $R^a$ and $R^b$ are the same as or different from each other and each represents a hydrogen atom, a $C_1$-$C_6$ alkyl group which may have a substituent, or a $C_3$-$C_8$ cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and L represents a single bond, or a salt thereof.

In certain embodiments, $R^a$ and $R^b$ independently may represent a hydrogen atom, a methyl group, an ethyl group, a n-propyl group, an iso-propyl group, a n-butyl group, an iso-butyl group, or a tert-butyl group. -T-Z— may represent —$CH_2CH_2$— or —$C(CH_3)_2CH_2O$—. Y may represent —$CH_2$—$N(CH_2CH_3)$— or —$CH_2$—$N(CH_2CH_2OH)$—. Each of R" independently may represents a hydrogen atom or a methoxy group. R" may represents a hydroxyl group. In certain embodiments, the compound may be (R)-6-{2-{ethyl [4-(2-ethylaminoethyl)benzyl]amino}-4-methoxyphenyl}-5,6,7,8-tetrahydronaphthalen-2-ol. Examples of other SERMS are described in U.S. Pat. No. 7,612,114, U.S. U.S. Pat. Nos. 7,960,412, 8,399,520, U.S. Patent Publication No. US 2009-0325930, and U.S. Patent Publication No. US 2006-0116364, the contents of which are incorporated by reference in their entirety. An effective amount of the compound may be administered.

(a) Dosages

In general, the dosage of administered SERM will vary depending upon such factors as the patient's age, weight, height, sex, general medical condition, and previous medical history. Typically, it is desirable to provide the recipient with a dosage of SERM, which is in the range of from about 1 pg/kg to 10 mg/kg (amount of agent/body weight of patient), although a lower or higher dosage also may be administered as circumstances dictate. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of the SERM is a dose of between 0.1 and 200 mg/kg, for example between 0.1 and 10 mg/kg, or about 20 mg/kg to about 100 mg/kg. The therapeutically or prophylactically effective amount of the SERM may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated.

In some embodiments, the SERM can be administered to a patient in an amount of about 10 mg/day to about 500 mg/day, about 10 mg/day to about 200 mg/day (e.g., 10, 20, 30, 40, 50, 60, 70, 80, 90, 100, 110, 120, 130, 140, 150, 160, 170, 180, 190, or 200 mg/day), 20 mg/day to about 100 mg/day, 100 mg/day to about 200 mg/day, or about 200 mg/day to about 500 mg/day (e.g., 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 mg/day), inclusive of any single or multi-dose daily administration regimen that falls within that total daily dose range. In some embodiments, the dose is from about 20 mg/day to about 100 mg/day. Additionally, one of ordinary skill in the art would also know how to adjust or modify variables such as dosage, dosage schedules, and routes of administration, as appropriate, for a given subject.

Further, the SERM dose may be determined by a person skilled in the art and may vary according to factors such as the disease state, age, sex, and weight of the individual, and the ability of the SERM to elicit a desired response in the individual. The dose is also one in which toxic or detrimental effects, if any, of the SERM are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

(b) Rad 1901

The SERM may be RAD 1901. Although RAD 1901 may effectively treat vasomotor symptoms, its pharmacology is complex. Treatment of ER positive breast cancer cells with RAD 1901 in MCF7 and BT483 cells resulted in a pronounced dose dependent down regulation of the receptor expression. RAD 1901 is a unique SERM in that it apparently has a relative agonist/antagonist activity in the brain that is determined by dose. At low doses RAD 1901, behaves as a SERM as it exhibits estrogenic activity. At high doses, RAD 1901 may function as a SERD, reversing the response.

While targeting of the estrogen signaling axis has proven effective in the treatment of breast cancer and osteoporosis, implementing a safe therapy that mitigates the vasomotor. While efforts are being made to address this unmet medical need using tissue specific estrogen complexes (TSECs) that combine estrogens and SERMs with the intention of inhibiting estrogen action only in some tissues (i.e., breast and uterus), preliminary clinical data suggest that RAD 1901 may accomplish the same medical goal without exposing the patient to estrogen. The apparent dose dependent down regulation of ER by RAD1901 suggest that at a therapeutic (low) dose, RAD1901 may be mediating some level of agonist activity, while a higher dose results in more extensive SERM activity and an effective blockade in estrogen signaling, thereby exacerbating vasomotor symptoms.

The binding of RAD1901 enables the presentation of protein-protein interaction surfaces within the hinge region (flexible structure linking the DNA and hormone binding domains) of ESR1 that are involved with transcriptional activity. Identification of the coregulators that interact with these surfaces on ESR1 enable a definition of their importance in RAD1901 pharmacology. As the occupancy of the receptor increases, it is targeted for degradation, which results in a quantitative inhibition of ESR1 signaling. This pharmacological profile resembles that of a classical agonist, such as 17β-estradiol, where the agonist signal is terminated by proteasome-dependent receptor degradation. The pharmacological actions of RAD1901 represent an uncoupling of ESR1-dependent transcriptional activation from degradation. At appropriate doses, the SERD activity manifested by RAD1901 may result in useful clinical activity in breast cancer.

As disclosed herein, RAD1901 inhibited estrogen activation of ESR1 in vitro and in vivo, inhibited estrogen-dependent breast cancer cell proliferation and xenograft tumor growth, and mediated dose-dependent downregulation of ESR1 protein. Doses of RAD1901 that were insufficient to induce ESR1 degradation were shown to result in activation of ESR1 target genes and in stimulation of xenograft tumor growth. RAD1901 may be used as targeted therapy for the treatment of breast cancer brain metastases.

In some embodiments, a low dose of RAD 1901 may be about 0 mg/kg to about 25 mg/kg, about 0 mg/kg to about 20 mg/kg, about 0 mg/kg to about 15 mg/kg, about 0 mg/kg to about 10 mg/kg, about 0 mg/kg to about 5 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 2 mg/kg to about 25 mg/kg, about 2 mg/kg to about 20 mg/kg, about 2 mg/kg to about 15 mg/kg, about 2 mg/kg to about 10 mg/kg, about 2 mg/kg to about 5 mg/kg, about 3 mg/kg to about 25 mg/kg, about 3 mg/kg to about 20 mg/kg, about 3 mg/kg to about 15 mg/kg, about 3 mg/kg to about 10 mg/kg, about 3 mg/kg to about 5 mg/kg, about 4 mg/kg to about 25 mg/kg, about 4 mg/kg to about 20 mg/kg, about 4 mg/kg to about 15 mg/kg, about 4 mg/kg to about 10 mg/kg, about 4 mg/kg to about 5 mg/kg, about 5 mg/kg to about 25 mg/kg, about 5 mg/kg to about 20 mg/kg, about 5 mg/kg to about 15 mg/kg, about 5 mg/kg to about 10 mg/kg, about 5 mg/kg to about 7.5 mg/kg. In some embodiments, a low dose of RAD 1901 may be less than about 25 mg/kg, about 24 mg/kg, about 23 mg/kg, about 22 mg/kg, about 21 mg/kg, about 20 mg/kg, about 19 mg/kg, about 18 mg/kg, about 17 mg/kg, about 16 mg/kg, about 15 mg/kg, about 14 mg/kg, about 13 mg/kg, about 12 mg/kg, about 11 mg/kg, about 10 mg/kg, about 9 mg/kg, about 8 mg/kg, about 7 mg/kg, about 6 mg/kg, about 5 mg/kg, about 4 mg/kg, about 3 mg/kg, about 2 mg/kg, or about 1 mg/kg.

In some embodiments, a high dose of RAD 1901 may be about 15 mg/kg to about 500 mg/kg, about 15 mg/kg to about 250 mg/kg, about 15 mg/kg to about 200 mg/kg, about 15 mg/kg to about 150 mg/kg, about 15 mg/kg to about 100 mg/kg, about 15 mg/kg to about 75 mg/kg, about 20 mg/kg to about 500 mg/kg, about 20 mg/kg to about 250 mg/kg, about 20 mg/kg to about 200 mg/kg, about 20 mg/kg to about 150 mg/kg, about 20 mg/kg to about 100 mg/kg, about 20 mg/kg to about 75 mg/kg, about 25 mg/kg to about 500 mg/kg, about 25 mg/kg to about 250 mg/kg, about 25 mg/kg to about 200 mg/kg, about 25 mg/kg to about 150 mg/kg, about 25 mg/kg to about 100 mg/kg, or about 25 mg/kg to about 75 mg/kg. In some embodiments, a high dose of RAD 1901 may be more than about 15 mg/kg, 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 105 mg/kg, about 110 mg/kg, about 115 mg/kg, about 120 mg/kg, about 125 mg/kg, about 130 mg/kg, about 135 mg/kg, about 140 mg/kg, about 145 mg/kg, about 150 mg/kg, about 155 mg/kg, about 160 mg/kg, about 165 mg/kg, about 170 mg/kg, about 175 mg/kg, about 180 mg/kg, about 185 mg/kg, about 190 mg/kg, about 195 mg/kg, about 200 mg/kg, about 250 mg/kg, about 300 mg/kg, about 350 mg/kg, about 400 mg/kg, about 450 mg/kg or about 500 mg/kg.

In some embodiments, RAD1901 can be administered to a patient in an amount of about 10 mg/day to about 500 mg/day, about 10 mg/day to about 200 mg/day (e.g., 10, 20, 30, 40, 50, 60, 70, 80, 90, 100, 110, 120, 130, 140, 150, 160, 170, 180, 190, or 200 mg/day), 20 mg/day to about 100 mg/day, 100 mg/day to about 200 mg/day, or about 200 mg/day to about 500 mg/day (e.g., 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 mg/day), inclusive of any single or multi-dose daily administration regimen that falls within that total daily dose range. In some embodiments, the dose is from about 20 mg/day to about 100 mg/day. Additionally, one of ordinary skill in the art would also know how to adjust or modify variables such as dosage, dosage schedules, and routes of administration, as appropriate, for a given subject.

3. Methods of Treating Estrogen Receptor Positive Cancer of the Brain

The methods described above may be used to treat an estrogen receptor positive cancer of the brain. In some embodiments, the cancer may include subtypes of brain tumors that may express ER, such as Breast Cancer Brain Metastases (BCBM), Astrocytoma, Chondrosarcoma, Craniopharyngioma, Glioblastoma, Glioma, Hemangioma, Medulloblastoma, Meningioma, Neurofibroma, Neuronal and Mixed Neuronal-Glial Tumors, Oligoastrocytoma, Pituitary Tumor, PNET—(primitive neuroectodermal tumor), Schwannomak, or Leptomeningeal metastases. In some embodiments, the cancer may be other cancers such as Atypical Teratoid Rhabdoid Tumor (ATRT), Choroid Plexus Carcinoma, Ependymoma, Germ Cell Tumor, Juvenile Pilocytic Astrocytoma, Oligodendroglioma, or Pineal Tumor.

(a) Breast Cancer Brain Metastases

The methods described above may be used to treat a subject suffering from breast cancer brain metastases. 10-20% of breast cancer patients ultimately experience breast cancer metastasis to the brain, i.e., BCBM. 30-40% of BCBM express ER. ER expression is retained in 50-65% of BCBM that arise from ER+/PR+ tumors, despite treatment of the initial tumor with endocrine therapies. As many as 50% of BCBM express the estrogen receptor, and the brain is an environment rich in aromatase activity, suggesting that estrogen levels and signaling may be of importance in the establishment and maintenance of BCBM. Therefore, the availability of the SERM, such as RAD 1901 or a similar SERM with significant brain penetrance, that can induce estrogen receptor turnover in BCBM may provide therapeutic benefit in the treatment of BCBM.

Few treatments can access the brain, one of three most frequent sites of metastasis for breast cancer, leaving targeted or whole brain radiation as the standard of care for patients diagnosed by BCBM. In the majority of BCBM occurring in patients diagnosed with ESR1-positive breast tumors, ESR1 expression is retained, and the high expression of aromatase in the brain suggests that the disruption of ESR1 signaling may be beneficial in this setting. Therefore, the availability of the SERM, such as RAD1901 or a similar SERM with significant brain penetrance, that can induce estrogen receptor turnover in BCBM may provide therapeutic benefit in the treatment of BCBM.

(b) Astrocytoma

Astrocytoma is a type of cancer of the brain that originate in astrocytes, which are a particular kind of glial cells, start-shaped brains cells in the cerebrum. Low ERb expression has been shown to be associated with the progression of astrocytoma.

(c) Chondrosarcoma

Chondrosarcoma is a type of tumor that affects the bones and joints. Chondrosarcoma grow from the types of cells that make cartilage in the skull. In the head, these tumors grow inside the bones at the base of the back part of the skull and may be very close to the nerves and blood vessels around the brainstem. ER is present and active in chondrosarcoma tumors.

(d) Craniopharyngioma

Craniopharyngioma is a benign tumor that develops near the pituitary gland. ER may be present in craniopharyngioma and may be associated with improved disease prognosis.

(e) Glioblastoma Multiforme

Glioblastoma multiforme, also known as "glioblastoma," is the most common and most aggressive malignant primary brain tumor in humans, involving glial cells and accounting for 52% of all functional tissue brain tumor cases and 20% of all intracranial tumors. Glioblastoma may express both ERs, which may play a role in etiology and treatment.

(f) Glioma

Glioma is a type of tumor that starts in the brain or spine and arises from glial cells. Gliomas make up approximately 30% of all brain and central nervous system tumors and 80% of all malignant brain tumors. Glioma may express both ERs, which may play a role in etiology and treatment. Glioma may be responsive to tamoxifen treatment.

(g) Hemangioma

Hemangioma is a benign and usually self-involuting tumor (swelling or growth) of the endothelial cells that line blood vessels. Hemangioma is characterized by increased number of normal or abnormal vessels filled with blood. Human vascular endothelial cells express ER isoforms and are responsive to tamoxifen treatment. Hemangioma may be intracranial hemangiomas or cutaneous hemangiomas.

(h) Medulloblastoma

Medulloblastoma is a highly malignant primary brain tumor that originates in the cerebellum or posterior fossa. Medulloblastomas may originate from immature or embryonal cells at their earliest stage of development. Medulloblastoma may express ER isoforms. ER isoforms are associated with growth and migration of these cells.

(i) Meningioma

Meningiomas are a diverse set of tumors arising from the meninges, i.e., the membranous layers surrounding the central nervous system. Meningioma may express both ER isoforms. Meningioma may be responsive to tamoxifen treatment.

j) Neurofibroma

Neurofibroma is a benign nerve sheath tumor in the peripheral nervous system.

Neurofibromas arise from nonmyelinating-type Schwann cells that exhibit biallelic inactivation of the NF1 gene that codes for the protein neurofibromin. Neurofibroma may be ER positive.

(k) Neuronal & Mixed Neuronal-Glial Tumors

Neuronal & Mixed Neuronal-Glial Tumors are rare, benign tumors that come from ganglion-type cells, i.e., groups of nerve cells. ER may be present in these tumors.

(l) Oligoastrocytoma

Oligoastrocytomas are a subset of brain tumors that present with an appearance of mixed glial cell origin, astrocytoma and oligodendroglioma. Oligoastrocytoma may have a lasting response to tamoxifen treatment.

(m) Pituitary Tumor

A pituitary tumor is an abnormal growth in the pituitary gland. Both ERα and ERb may be detected in pituitary tumors.

(n) Primitive Neuroestodermal Tumor (PNET)

Primitive neuroestodermal tumor is a neural crest tumor. The majority of the cells in the PNET are derived from neuroectoderm but have not developed and differentiated in the way a normal neuron would, and so the cells appear "primitive. ERa may be present and may increase metastatic potential via extracellular signal-regulated Kinase (ERK) activation.

(o) Schwannoma

Schwannoma (also known as an "neurilemmoma," "neurinoma," "neurolemmoma," and "Schwann cell tumor") is a benign nerve sheath tumor composed of Schwann cells, which normally produce the insulating myelin sheath covering peripheral nerves. Schwannoma may express ERα.

(p) Leptomeningeal Metastases

Leptomeningeal metastasis is breast cancer metastasis to the membranes (meninges) surrounding the brain and spinal cord. A durable response has been observed in patient(s) treated with aromatase inhibitors, which suggests possible responsiveness to ER targeted therapies.

4. Methods of Treating a Cancer that is Resistant to an Estrogen Receptor Modulator The methods described above may be used to treat a cancer that is resistant to an estrogen receptor modulator. The resistance to the estrogen receptor modulator may be acquired. The estrogen receptor modulator may be a selective estrogen receptor modulator (SERM). The SERM may be tamoxifen, idoxifene, raloxifene, or ICI 182,780. The cancer may be breast, endometrial or ovarian cancer. The cancer may be tamoxifen resistant breast cancer.

Because patients diagnosed with BCBM are likely to have already progressed following endocrine therapies, RAD1901 may be used in breast tumors resistant to tamoxifen and/or aromatase inhibitors. RAD1901 may be beneficial in the BCBM setting when combined with additional therapeutic(s) that will ensure the inhibition of growth of peripheral metastases.

5. Mechanisms of Delivery

The SERM may be formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the SERM is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Various delivery systems are known and can be used to administer one or more SERMs or the combination of one or more SERMs and a prophylactic agent or therapeutic agent useful for preventing, managing, treating, or ameliorating a disorder or one or more symptoms thereof, e.g., encapsulation in liposomes, microparticles, microcapsules, receptor-mediated endocytosis (see, e.g., Wu and Wu, *J. Biol. Chem.* 262:4429-4432 (1987)), etc. Methods of administering a prophylactic or therapeutic agent of the SERM include, but are not limited to, parenteral administration (e.g., intradermal, intramuscular, intraperitoneal, intravenous and subcutaneous), epidural administration, intratumoral administration, and mucosal administration (e.g., intranasal and oral routes).

6. Combination Treatments

The methods described above may include a combination treatment of the compound of formula I with other drugs and/or other conventional cancer therapies, such as hormone therapy.

(a) Combination Drugs

The methods may further include administering an effective amount of at least one compound of a cyclin-dependent kinase 4 and 6 inhibitor (CDK4/6 inhibitor), an antiestrogen, a ligand of retinoic acid or retinoic X receptor, an antiprogestin, an antiandrogen, vitamin D or metabolite thereof, a farnesyl transferase inhibitor, a PPARα or gamma agonist and a MAP kinase inhibitor.

(b) Conventional Cancer Therapies

Conventional cancer therapies may include surgery, radiation therapy, chemotherapy, hormone therapy, and targeted therapy. Examples of surgery include open craniotomy with maximal excision, which may be followed by radiation therapy. Examples of radiation therapy include whole-brain irradiation, fractionated radiotherapy, and radiosurgery, such as stereotactic radiosurgery, e.g., Gamma Knife radiosurgery. Examples of chemotherapy include anthracyclines, such as doxorubicin (Adriamycin, Doxil), epirubicin (Ellence), and daunorubicin (Cerubidine, DaunoXome), capecitabine (Xeloda), carboplatin (Paraplatin), cisplatin, cyclophosphamide (Cytoxan), eribulin (Halaven), fluorouracil (also called 5-fluorouracil or 5-FU; Adrucil), gemcitabine (Gemzar), ixabepilone (Ixempra), methotrexate (Amethopterin, Mexate, Folex), mitoxantrone (Novantrone), mutamycin (Mitomycin), taxanes, such as paclitaxel (Taxol, Abraxane), and docetaxel (Taxotere), thiotepa (Thioplex), vincristine (Oncovin, Vincasar PES, Vincrex), and vinorelbine (Navelbine). Examples of targeted therapy include trastuzumab (Herceptin), lapatinib (Tykerb), bevacizumab (Avastin), pertuzumab (Perjeta), and everolimus (Afinitor).

i. Endocrine Therapy (Hormone Therapy)

Endocrine therapy, also known as hormonal therapy, hormone therapy, and hormone treatment, is a treatment that adds, blocks, or removes hormones. For example, hormones may be given to adjust low hormone levels. Synthetic hormones or other drugs may be given to block the body's natural hormones to slow or stop the growth of certain cancers (such as prostate and breast cancer). Endocrine therapy may also include surgery to remove the gland that makes a certain hormones.

Examples of hormone therapy include selective estrogen receptor modulators (SERMs), such as tamoxifen, raloxifene, endoxifene, toremifene, lasofoxifene, pipendoxifene, bazedoxifene, and ospemifene, aromatase inhibitors, such anastrozole, letrozole, exemestane, formestane, fadrozole, aminoglutethimide, and testolactone, a HER2 intervention drug, such as a HER2 inhibitor, such as Herceptin (trastuzumab), pertuzumab, and lapatinib, and estrogen-receptor downregulators, such as fulvestrant (ICI 182,780).

7. Subject or Subject in the Method

The methods described above are directed to treating a subject with a SERM. The subject treated by the methods described above may be a subject or patient suffering from or at risk of suffering from an estrogen receptor positive cancer of the brain, such as BCBM, or a cancer that is resistant to an estrogen receptor modulator, such as tamoxifen resistant breast cancer. The subject may be diagnosed or identified as having or at risk of having cancer using known methods and assays, such as a biopsy. The subject may be treated with SERM alone or in combination with another drug and/or conventional cancer therapy, as described above. The subject may be treated with the SERM as a neoadjuvant therapy or post-surgery. The present invention has multiple aspects, illustrated by the following non-limiting examples.

EXAMPLES

The foregoing may be better understood by reference to the following examples, which are presented for purposes of illustration and are not intended to limit the scope of the invention.

Example 1

In Vitro Analysis of ER Degradation 48 hours prior to treatment, MCF7 cells were plated in phenol red free DMEM/F12 media supplemented with 8% charcoal stripped fetal bovine serum, non-essential amino acids, and sodium pyruvate. After 20 hours of treatment with the indicated ligands, i.e., estradiol ("E2"; Sigma-Aldrich), antiestrogen ICI 182,780 ("ICI"; Sigma-Aldrich), and 4-hydroxytamoxifen ("4OHT"; Sigma-Aldrich), (0-1 µM), cells were washed and lysed in RIPA lysis buffer (50 mM Tris, pH 8, 150 mM NaCl, 1% IGEPAL, 0.02% SDS, 0.5% sodium deoxycholate, 1 mM EDTA). 50 µg of cleared lysate was resolved by SDS-PAGE and analyzed by immunoblot detection of ERα or cytokeratin 18 (loading control), as illustrated in FIG. 1A.

Example 2

In Vivo Analysis of RAD1901 in MCF7 Xenograft Tumors

A total of 90 female Nu/Nu mice were ovariectomized and implanted subcutaneous simultaneously with an estrogen pellet (Innovative Research of America) releasing 0.72 mg estradiol (E2) over 60 days. 2 days later an approximately 6 mm3 fragment of an MCF7 xenograft tumor (isolated from a recently sacrificed estrogen treated nu/nu mouse) was inserted subcutaneous into the axial mammary gland. Tumor growth (by caliper measurement) and animal body weight were monitored 3× weekly until tumor volume reached ~0.2 cm$^3$. Mice (n~10) were randomized to the following groups: estrogen control (corn oil vehicle), E2+RAD1901 (20 mg/kg; Radius Health, Inc.), E2+Tamoxifen (20 mg/kg; Sigma-Aldrich). Treatments were formulated in sterile corn oil and were administered daily by subcutaneous injection. After 3 weeks of treatments, animals were euthanized and serum and tissues saved for analysis. FIG. 1B depicts tumor volume analyzed using non-linear curve fit and exponential growth calculation (Graphpad Prism), followed by two-way ANOVA and Bonferroni analysis.

Example 3

Mechanism by which RAD1901 Downregulates ER Expression

Figure 2A:
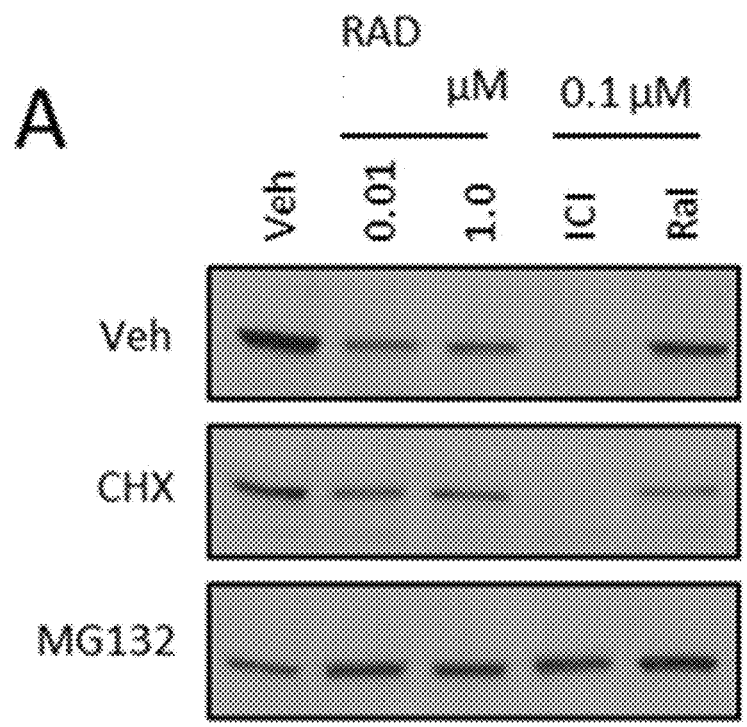
FIGS. 2A-2B show the mechanism by which RAD1901 downregulates ER expression.
Figure 2B:
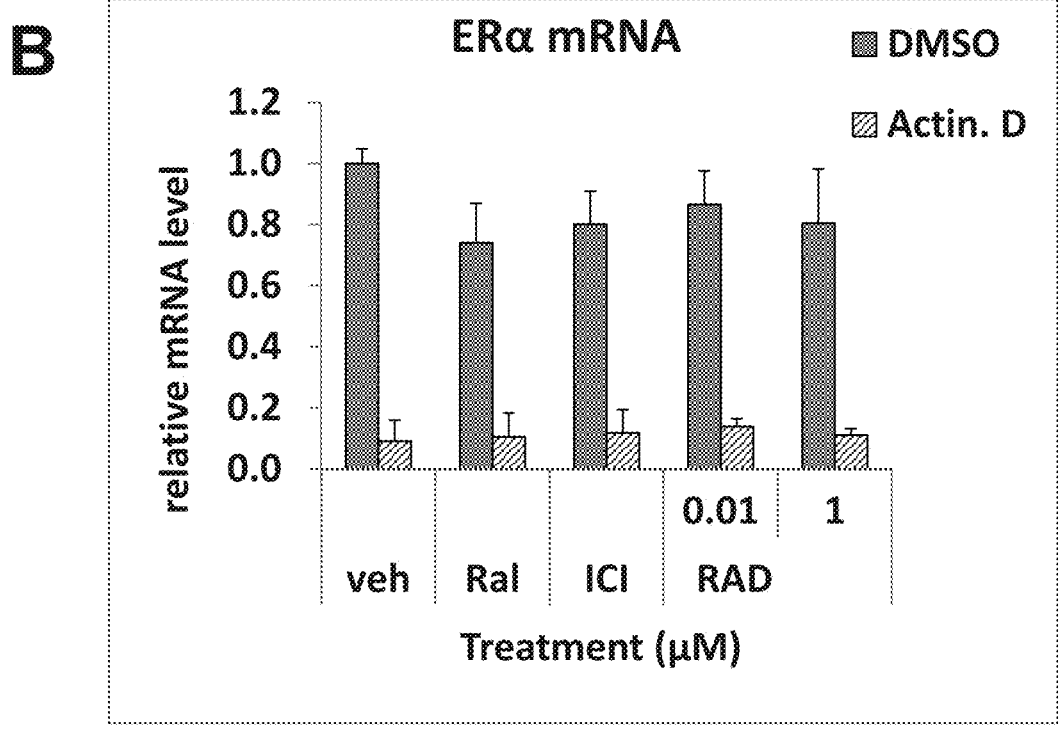

While the reduced levels of ER following treatment with RAD1901 results in receptor degradation, whether the drug influences the transcriptional activity of the gene encoding ER was determined (FIG. 2). MCF7 cells were pre-treated with Vehicle (Veh) or translation (cyclohexamide—CHX, 10 µg/ml), proteasome (MG132, 30 µM) or transcription (Actinomycin D—Actin. D, 100 ng/ml) inhibitors for 2 hours prior to 6 hours of treatment with RAD1901 (0.1 or 1 µM), or 0.1 µM ICI 182,780 (ICI) or raloxifene (Ral). FIG. 2A shows ERα protein expression in whole cell extracts was analyzed by immunoblot, as in Example 1. FIG. 2B shows cells treated, as indicated, were washed in PBS prior to lysis. RNA isolation (BioRad) and reverse transcription (iScript; BioRad) were performed per kit manufacturer's instructions. qRT-PCR of cDNA was done using iQ SYBR Green Supermix (Bio-Rad) per kit instructions and performed using the iCycler optical system with associated software (Bio-Rad). mRNA abundance was calculated using the ΔΔCT method to normalize ERα mRNA expression to similarly detected housekeeping gene 36B4.

Example 4

Conformational Changes Induced in ER as a Consequence of Binding of RAD1901

A series of short peptides whose ability to interact with ERα is influenced by the nature of the bound ligand were previously identified (see Chang et al. *Methods Enzymol.* (2003) 364: 118-42; Huang et al. *Mol Endocrinol.* (2002) 16(8): 1778-92; Connor et al. *Cancer Res.* (2001) 61(7): 2917-22; Chang et al. *Mol Cell Biol.* (1999) 19(12):8226-39; and Norris et al. *Science* (1999) 285(5428): 744-6). The interaction of these "conformational probes" can be measured in vitro or within intact cells and thus enables the definition of ligand induced conformational changes in the receptor. This is significant, since differences in receptor conformation facilitate the engagement of different coregulatory proteins resulting in different pharmacological activities. Application of this technology has led to the determination that their impact on receptor structure is a distinguishing feature of ER ligands.

Figure 3:
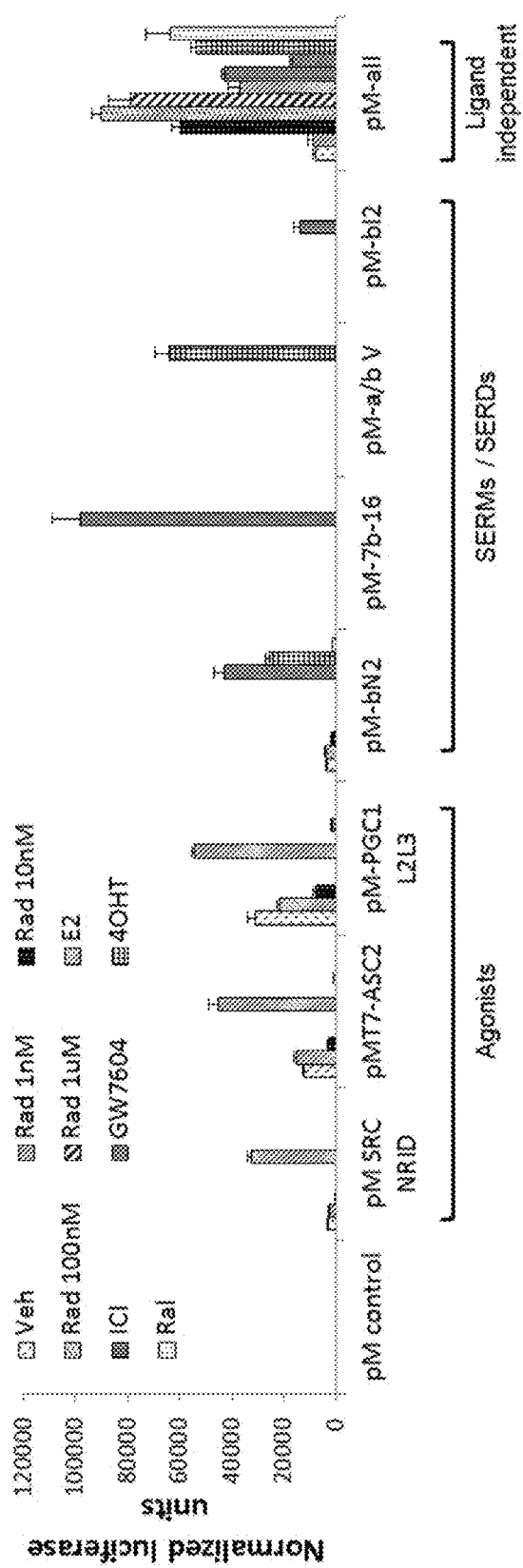
FIG. 3 shows the interaction between ER and conformation-specific peptides in mammalian two-hybrid system.

FIG. 3 shows that RAD1901 induces a unique conformation of ERα as shown in the interaction between ER and conformation-specific peptides in a mammalian two-hybrid system. Triplicate wells of SKBR3 cells were transfected (Lipofectin per manufacturer's instructions) with plasmids expressing ERα fused to VP16 together with Gal4DBD alone (control) or fused to ER interacting peptides noted on the horizontal axis. Cells were then treated with RAD1901 (1 nM-1 µM) or the indicated ER ligands (100 nM). Interaction of ERα with the Gal4DBD peptide constructs was detected through activation of a Gal4 responsive luciferase reporter construct and was normalized to detected β-galactosidase activity generated by a co-transfected constitutive expression vector. Ligand classes recognized by each probe are indicated below the graph.

Example 5

RAD1901 Possesses Dose Dependent Agonist and/or Antagonist Potential

Figure 4A:
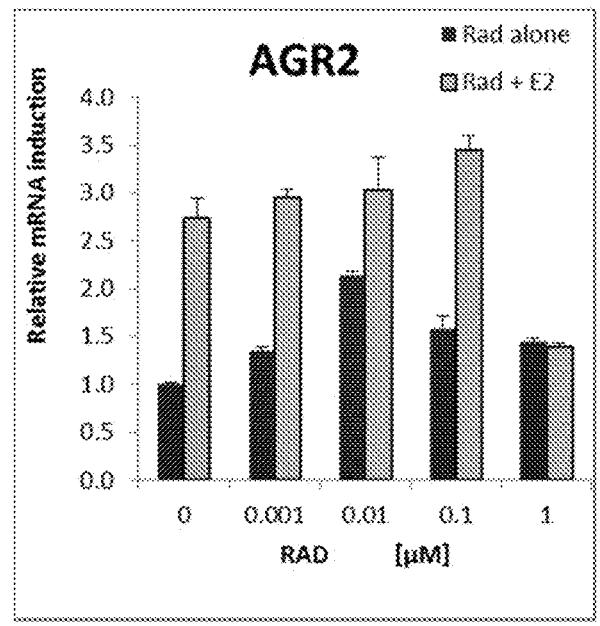
FIGS. 4A-4B show RAD1901 exhibits dose dependent agonist/antagonist regulation of ER transactivation of target genes.
Figure 4B:
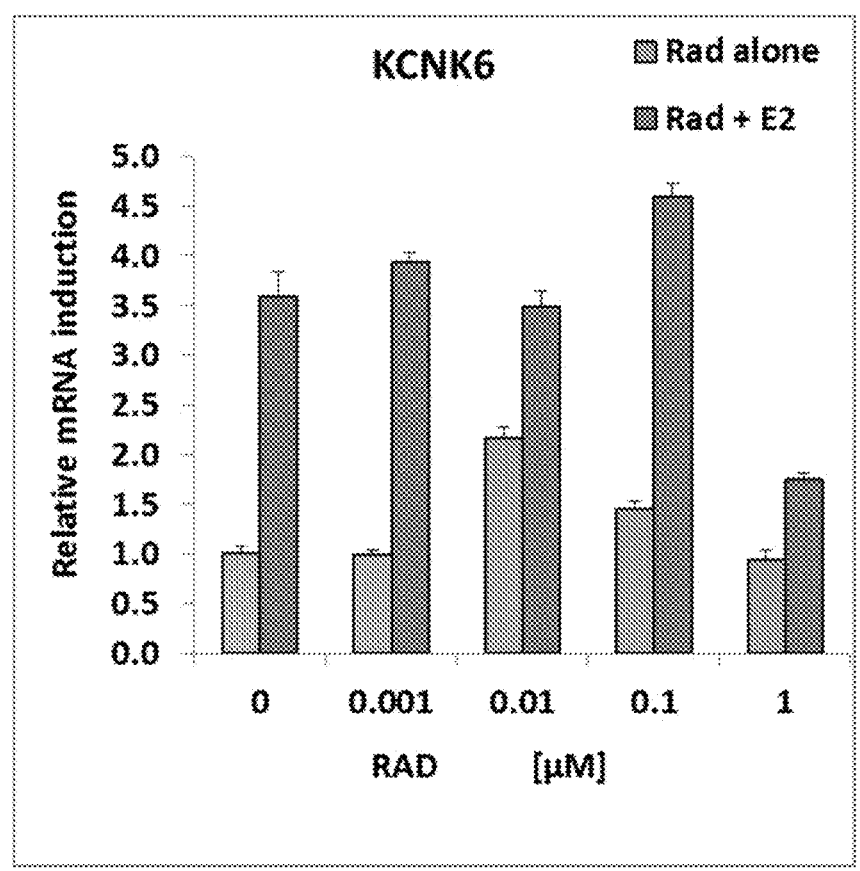

The complex pharmacological activities exhibited by RAD1901 suggest that it will exhibit a unique gene expression profile in target cells. A recent extensive microarray analysis has identified "sentinel" subsets of ER-responsive genes that can differentiate between ER agonists, SERMs and SERDs. For example, some of these are responsive to only the SERM tamoxifen, while others display a graded response to SERMs with varying agonist/antagonist potential, and yet others are repressed by agonists or SERMs and are induced only by SERDs. RAD1901 exhibits dose dependent agonist/antagonist regulation of ER transactivation of target genes (FIG. 4). MCF7 breast cancer cells were treated 24 hours with RAD1901 (0-1 µM) in the presence or absence of 17β-estradiol (1 nM). RNA isolation and the analysis of the expression of target genes Anterior gradient protein 2 (AGR2) and KCNK6 was conducted as in Example 3.

Example 6

Materials and Methods

Reagents. Purchased ESR1 ligands included 17β-estradiol (Sigma), ICI 182,780 (Tocris), tamoxifen (Sigma), raloxifene (Tocris), and 4-hydroxytamoxifen (Sigma). (R)-6-(2-(N-(4-(2-(ethylamino)ethyl)benzyl)-N-ethylamino)-4-methoxyphenyl)-5,6,7,8-tetrahydronaphthalen-2-ol dihydrochloride was provided by Radius Pharmaceuticals. Bazedoxifene and GW7604 were synthesized as previously described (Miller et al., (2001) *J Med Chem* 44 (11):1654-1657; U.S. Pat. No. 5,681,835). Ligands were dissolved in ethanol or DMSO.

Cell culture. MCF7 and SKBR3 cell lines were maintained in DMEM/F12 or RPMI media (Invitrogen), respectively, supplemented with 8% fetal bovine serum (FBS, Gemini), non-essential amino acids (Invitrogen), and sodium pyruvate (Invitrogen). Unless otherwise indicated, cells were plated for experiments in media lacking phenol red and supplemented with 8% charcoal stripped FBS (CFS, Gemini). LTED MCF7 cells were maintained and plated for experiments in phenol red free DMEM/F12 media supplemented with 8% CFS that had been charcoal stripped twice. 48 hours after plating, cells were treated with ESR1 ligands as indicated, and were harvested for immunoblot or real time quantitative PCR analysis 24 hours after treatment. Cell lines were authenticated by STR analysis performed by ATCC in 2013.

Immunoblot analysis. Protein expression was analyzed as described (Wittmann et al., (2007) *Cancer Res* 67 (19):9549-9560) using antibodies purchased from Sigma-Aldrich—A5441 (β-actin) and Santa Cruz Biotechnology—sc-6259 (cytokeratin 18), sc-20680 (lamin A), sc-5546 (α-tubulin) and sc-8005 (ESR1).

RNA isolation and real time quantitative PCR. RNA isolation and analysis was performed as described (Wardell et al., (2001) *Biochem Pharmacol* 82 (2):122-130). mRNA abundance was calculated using the ΔΔCT method (Wardell et al., (2001) *Biochem Pharmacol* 82 (2):122-130). Primer sequences are available upon request.

Proliferation assays. Assays evaluating the effects of SERDs and SERMs on cell proliferation were performed as described (Wardell et al., (2013) *Clin Cancer Res* 19 (9): 2420-2431).

Transfections. Mammalian 2-hybrid analysis of VP16-ESR1 with conformation-selective peptide probes was performed essentially as previously described (Wardell et al., (2012) *Mol Endocrinol* 26 (7):1235-1248).

In vivo studies. All applicable international, national, and/or institutional guidelines for the care and use of animals were followed. All procedures performed in studies involving animals were in accordance with the ethical standards of the Duke University Institutional Animal Care and Use Committee.

Uterine wet weight analysis: Ovariectomized (10 days prior) female C57Bl/6 mice (Charles River) were treated daily (n=5) for 3 days with vehicle or estradiol benzoate (10 μg/kg sc) as well as vehicle, raloxifene (10 mg/kg sc), or RAD1901 (0.1-100 mg/kg sc). Ligands were dissolved in corn oil (Spectrum chemicals). On day 4, mice were euthanized, and tissues were retained for analysis. Uterine wet weight was calculated as a ratio of uterus weight upon removal to body weight post-mortem.

Xenograft tumor analysis: Estrogen-stimulated MCF7 tumors were initiated in the axial mammary gland of 6-week old estrogen-treated (0.72 mg/60 days pellet sc, Innovative Research of America) ovariectomized female NU/NU mice (in-house colony) by serial transfer and were measured as described (Wardell et al., (2013) *Clin Cancer Res* 19 (9): 2420-2431). FIG. 5: At ~0.1 cm$^3$ tumor volume, mice were randomized (n=9-10) to daily treatment with vehicle, RAD1901 (20 mg/kg), or tamoxifen (20 mg/kg). FIG. 9: At ~0.1 cm$^3$ tumor volume, the estrogen pellet was surgically removed, and mice were randomized (n=6-10) to daily treatment with vehicle or RAD1901 (0.3-10 mg/kg). Treatments were formulated as above. Animal tissues were processed and analyzed as described (Wardell et al., (2013) *Clin Cancer Res* 19 (9):2420-2431).

Example 7

RAD1901 Inhibits ESR1 Activity In Vitro and In Vivo

Figures 5A, 5B, 5C, 5D, 5E, 5F:
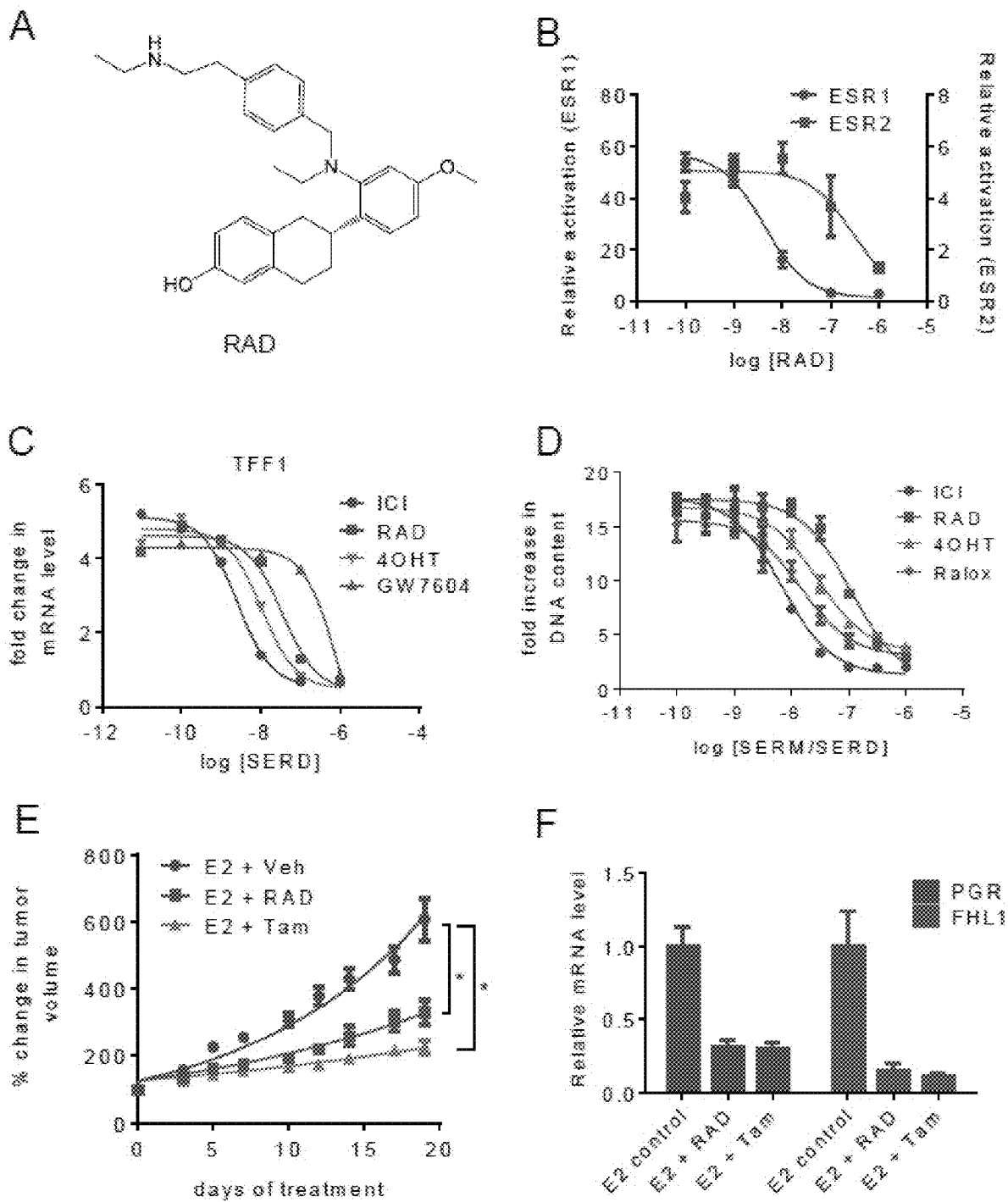
FIGS. 5A-5F show that RAD1901 inhibited ESR1 activity in vitro and in vivo.

The ability of RAD1901 (FIG. 5A) to modulate the 17-β estradiol (E2) dependent transcriptional activity of the human estrogen receptor alpha (ESR1) and human estrogen receptor beta (ESR2) was assessed in transiently transfected SKBR3 cells using a synthetic reporter gene. FIG. 5A shows the chemical structure of the SERM RAD1901. For FIG. 5B, SKBR3 cells were plated in phenol red free media supplemented with charcoal stripped FBS (CFS) 24 hours prior to transfection with an ERE-luciferase reporter together with ESR1 or ESR2 expression vectors. 24 hours after transfection, cells were treated with E2 (10 nM) together with RAD1901 ($10^{-10}$-$10^{-6}$ M) for 24 hours prior to harvest and analysis of luciferase activity normalized to co-transfected β-galactosidase control. For FIG. 5C, MCF7 cells were plated in phenol red free media supplemented with CFS 48 hours prior to treatment with $10^{-9}$ M E2 together with ICI 182,780 (ICI), RAD1901 (RAD), GW7604, or 4-hydroxytamoxifen (4OHT) ($10^{-11}$-$10^{-6}$ M) for 24 hours. mRNA levels of ESR1 target gene trefoil factor 1 (TFF1) were assessed using RT qPCR following RNA isolation. mRNA expression was normalized to the similarly detected 36B4 housekeeping gene, and expression levels are presented as fold change as compared to the vehicle-treated control. For FIG. 5D, MCF7 cells were plated in phenol red free media supplemented with CFS 24 hours prior to treatment, and were treated with $10^{-9}$ M E2 as well as with the indicated ligands ($10^{-11}$-$10^{-6}$ M) on days 1, 4, and 6 of an 8 day proliferation assay. DNA content as assessed by fluorescence was measured as a surrogate for cell proliferation. The relative increase in DNA fluorescence was calculated by normalizing to baseline values detected in a duplicate plate of cells that was harvested on day 1 prior to the initial treatment. Data are representative of at least 3 independent experiments. For FIGS. 5E-5F, MCF7 cell derived tumors were implanted into ovariectomized estrogen-treated nu/nu mice. When tumor volume reached ~0.1 cm$^3$, animals (n=9-10) were randomized to receive daily treatment with vehicle, tamoxifen (Tam, 20 mg/kg sc) or RAD1901 (RAD) (20 mg/kg sc). For FIG. 5E, mean tumor volume±SEM per day of treatment was presented. Significance (2-way ANOVA of matched values followed by Bonferroni comparison) as compared to the vehicle control was indicate d (*p<0.0001). For FIG. 5F, expression of ESR1 target genes in tumors was analyzed essentially as in (C).

In this analysis it was determined that although RAD1901 effectively inhibited E2-dependent activation of an ERE-luciferase reporter by either isoform, it was a more potent inhibitor of ESR1 (100-fold) (FIG. 5B). Similarly, it was demonstrated in MCF7 breast cancer cells that RAD1901 inhibited E2-dependent (a) induction of target gene transcription and (b) stimulation of cell proliferation with an efficacy and potency similar to that of the SERMs 4-hydroxytamoxifen (4OHT) and raloxifene (Ralox) and the SERDs ICI 182,780 (ICI, fulvestrant) and GW7604 (FIG. 5C-5D). To assess the activity of RAD1901 in vivo, a xenograft tumor study was conducted in estrogen-treated immunocompromised mice using the well-characterized ESR1-dependent MCF7 cell model. In this study, it was observed that RAD1901 (20 mg/kg) inhibited E2-stimulated growth of the tumors with efficacy similar to tamoxifen (20 mg/kg). RAD1901 and tamoxifen were also shown to suppress the expression of the ESR1-target genes PGR and FHL1 to the same degree in treated tumors, a result that confirms target engagement (FIGS. 5E-5F).

Example 8

RAD1901 Exhibits the Pharmacological Properties of a Selective Estrogen Receptor Degrader (SERD)

RAD1901 not only functioned as an ESR1 antagonist, but also downregulated the expression of this receptor. ESR1 expression was significantly downregulated in MCF-7 cells treated with RAD1901. For FIG. 6A, MCF7 cells were treated for 24 hours with ICI ($10^{-13}$-$10^{-7}$ M) or RAD1901 (RAD), ($10^{-11}$-$10^{-5}$ M). Expression of ESR1 and loading control cytokeratin 18 (CK18—FIG. 7A) in whole cell extracts were detected by immunoblot (top). ESR1 levels relative to CK18 were quantitated by densitometry using Adobe Photoshop (bottom). For FIG. 6B, MCF7 cells were plated as in FIG. 5B prior to 1 hour pre-treatment with vehicle or MG132 (10 μg/ml), followed by 6 hours of treatment with $10^{-7}$ M vehicle, ICI, Ral or RAD1901 (RAD), ($10^{-8}$-$10^{-6}$). ESR1 expression was detected as in FIG. 6A. For FIGS. 6C-6D, LTED MCF7 cells were plated in phenol red free media supplemented with FBS that was stripped of growth factors twice using charcoal. For FIG. 6C, after 48 hours, cells were treated for 24 hours with E2 ($10^{-7}$ M) or SERDs ($10^{-6}$ M) and ESR1 was analyzed as in FIG. 6A. For FIG. 6D, LTED MCF7 cells were treated with ICI or RAD1901 (RAD), ($10^{-11}$-$10^{-6}$ M) on days 1, 4, and 6 of an 8 day proliferation assay and analyzed as in FIG. 5.

Figures 6A, 6B, 6C, 6D:
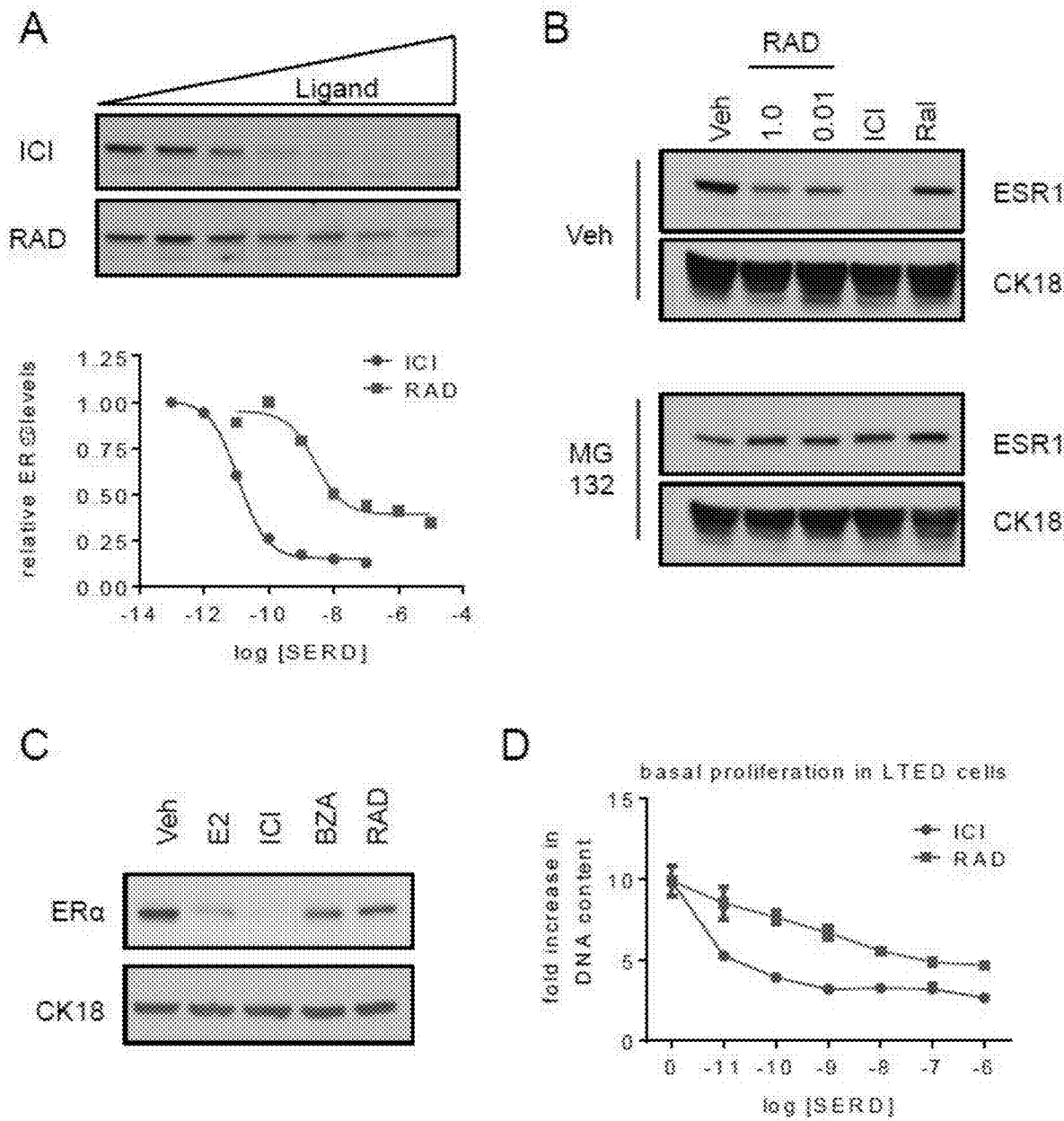
FIGS. 6A-6D show that RAD1901 downregulated ESR1 expression through receptor degradation.
Figures 7A, 7B, 7C:
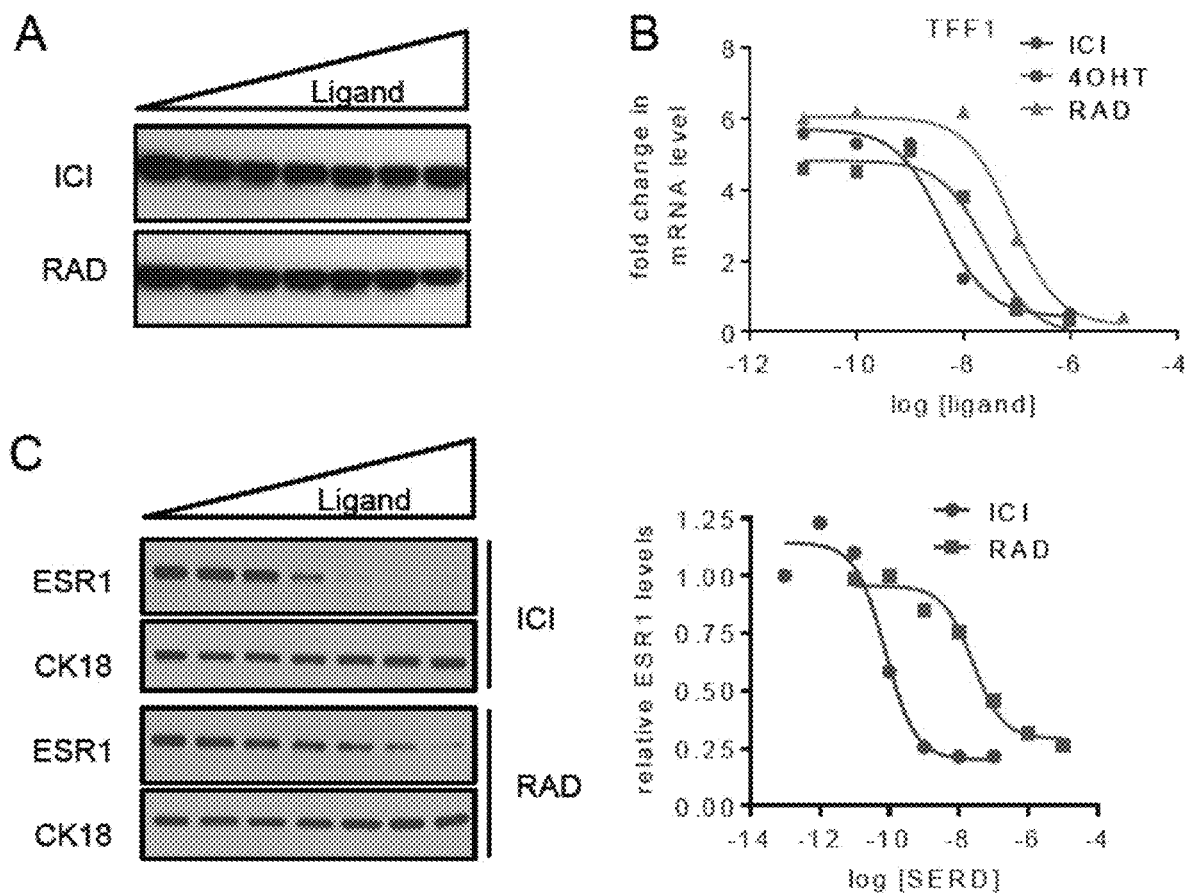
FIGS. 7A-7D show that the effects of RAD1901 on BT483 breast cancer cells were similar to those observed in MCF7 cells.

For FIG. 7A, cytokeratin 18 (CK18) loading control was detected for samples illustrated in FIG. 6A. For FIG. 7B, BT483 cells were plated in phenol red free media supplemented with CFS 48 hours prior to treatment with $10^{-9}$ M E2 together with ICI 182,780 (ICI), RAD1901 (RAD), GW7604, or 4-hydroxytamoxifen (4OHT) ($10^{-11}$-$10^{-6}$ M) for 24 hours. mRNA levels of ESR1 target gene trefoil factor 1 (TFF1) were assessed using RT qPCR following RNA isolation. mRNA expression was normalized to the similarly detected 36B4 housekeeping gene, and expression levels are presented as fold change as compared to the vehicle-treated control. For FIG. 7C, BT483 cells were treated for 24 hours with ICI ($10^{-13}$-$10^{-7}$ M) or RAD1901 (RAD), ($10^{-11}$-$10^{-5}$ M). Expression of ESR1 and loading control cytokeratin 18 in whole cell extracts were detected by immunoblot (right). ESR1 levels relative to CK18 were quantitated by densitometry using Adobe Photoshop (left). For FIG. 7D, BT483 cells were plated in phenol red free media supplemented with CFS 24 hours prior to treatment, and were treated with $10^{-9}$ M E2 as well as with the indicated ligands ($10^{-11}$-$10^{-6}$ M) on days 1, 4, and 6 of an 8 day proliferation assay. DNA content as assessed by fluorescence was measured as a surrogate for cell proliferation. The relative increase in DNA fluorescence was calculated by normalizing to baseline values detected in a duplicate plate of cells that was harvested on day 1 prior to the initial treatment. Data are representative of at least 3 independent experiments.

Figure 7D:
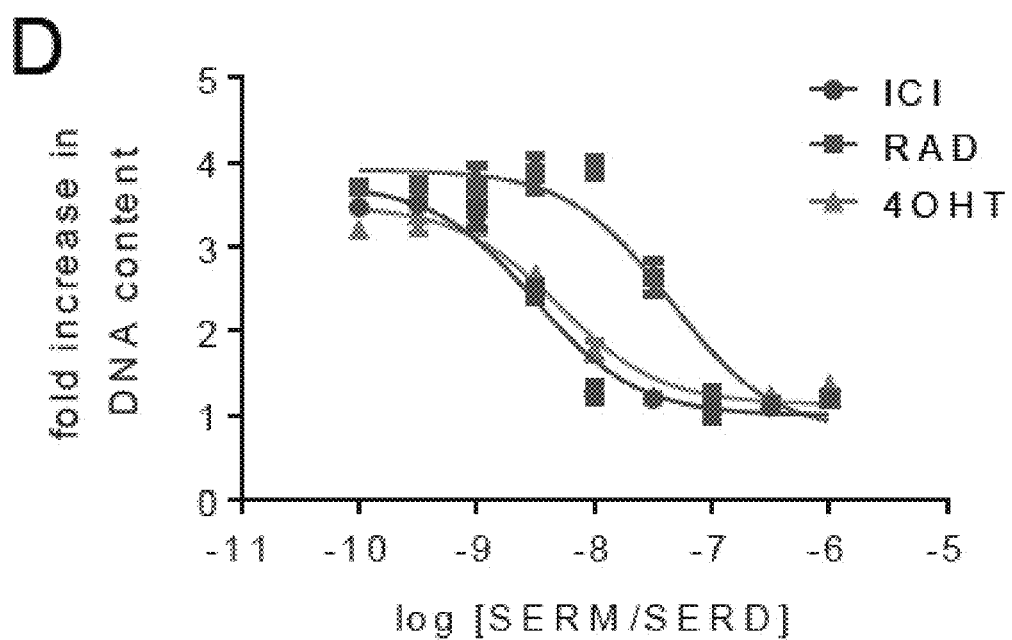

The downregulation of the ESR1 by RAD1901 was a significant contributor to its antagonist efficacy (FIG. 6A). RAD1901 had no effect on ESR1 mRNA expression (not shown). However, as observed in ICI-treated cells, the downregulation of ESR1 by RAD1901 was completely blocked by pre-treatment of cells with the proteasome inhibitor MG132 (FIG. 6B). Similar results were obtained in the BT483 breast cancer cell line (FIGS. 7B-7D). For comparative purposes, ESR1 expression levels were evaluated in cells treated with tamoxifen, which stabilizes ESR1 expression, and SERDs bazedoxifene (BZA), GW7604 and ICI. These studies revealed that the degree of downregulation of ESR1 by RAD1901 was similar to that achieved by BZA under the same conditions (FIG. 6C).

To assess the potential significance of this SERD activity, the activity of RAD1901 was evaluated in LTED MCF7 cells, an accepted model of aromatase resistance in which compounds with ER-antagonist activity alone, like tamoxifen, were minimally effective (not shown). In this assay, it was demonstrated that, like ICI and BZA, RAD1901 downregulated ESR1 expression and inhibited cell proliferation (FIG. 6D). Thus, considering its antagonist activity in several models of breast cancer and its ability to downregulate ESR1, it was appropriate to classify RAD1901 as a SERD.

Example 9

RAD1901 Exhibits Dose Dependent SERD Activity In Vivo

The observation that RAD1901 exhibited the pharmacological properties of a SERD was unexpected given that it was (a) identified in screens for compounds that manifest ESR1 agonist activity in the CNS and (b) evaluated in clinical trials as a potential treatment for the vasomotor symptoms (hot flashes) associated with menopause, an indication for which only estrogens have proven effective. However, the results of the clinical trials for hot flashes revealed that RAD1901 exhibited a complex pharmacology. At the lowest dose tested it appeared to effectively suppress hot flashes but was ineffective at the higher doses tested. This inverted U-shaped pharmacology suggested that at low doses this compound may have favorable agonist activity, but at higher doses the ability of RAD1901 to induce ESR1 turnover dominates. A series of studies was performed to explore the functional consequences of the complex pharmacological activities of RAD1901 in vivo.

As a first step, the impact of RAD1901 on uterine wet weight in mice was evaluated. For this study, increasing doses of RAD1901 was administered daily to ovariectomized C57Bl/6 mice receiving vehicle alone or E2 (10 μg/kg; a physiological replacement dose). A group of mice receiving 10 mg/kg of raloxifene was included for comparative purposes and for reference. Ovariectomized C57Bl/6 mice (n=5) were treated daily for 3 days with (FIG. 8A) vehicle or (FIG. 8B) estradiol (10 μg/kg) together with vehicle, Ralox (10 mg/kg) or RAD1901 (RAD), (0.3-100 mg/kg). At euthanasia, body weight as well as uterine wet weight was measured prior to cryopreservation of the uterus. When administered as a single agent, a statistically significant increase in uterine weight was observed in those animals receiving the lowest dose of RAD1901 (0.3 mg/kg). For FIG. 8C, ESR1 and β-actin expression in extracts made from pulverized uterine tissues were analyzed by immunoblot as in FIG. 5 (left). ESR1 expression relative to β-actin was quantitated as in FIG. 6 (right). Significant downregulation ($*p<0.05$) of ESR1 was determined by ANOVA followed by Bonferroni comparison.

Figures 8A, 8B, 8C:
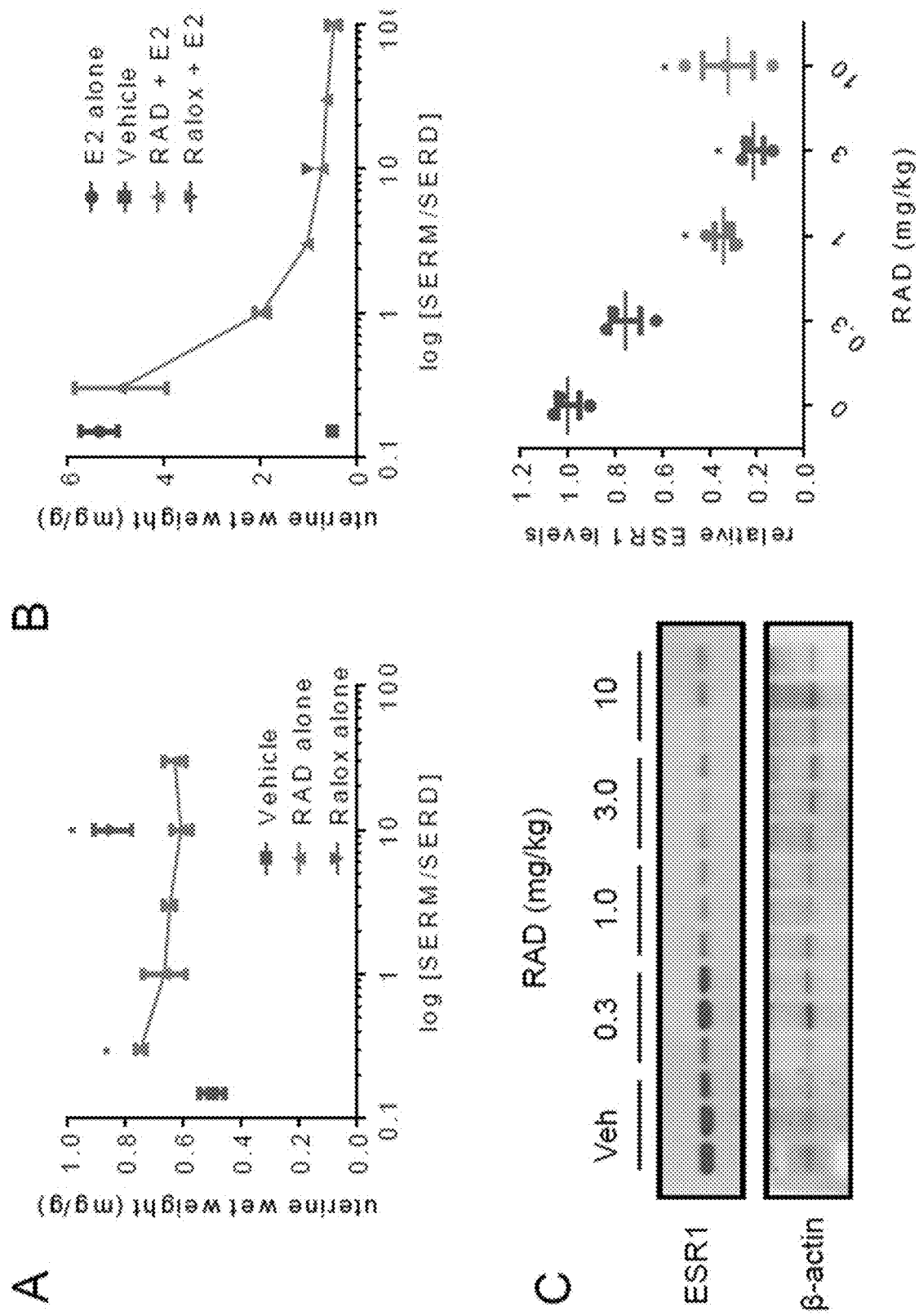
FIGS. 8A-8C show that the in vivo pharmacology of RAD1901 was influenced by SERD activity.

At doses of 1 mg/kg and above, the uterine wet weights of treated animals were indistinguishable from vehicle treated animals (FIG. 8A). Further, RAD1901 administration was shown to inhibit E2-dependent increases in uterine wet weight (FIG. 8B), an activity that tracked with the dose dependent downregulation of ESR1 expression (FIG. 8C). Notably, no decrease in ESR1 expression was observed in animals treated with 0.3 mg/kg, the dose where the agonist activity of RAD1901 in the uterine wet weight assay was observed (FIG. 8C). As observed in clinical trial for hot flashes, RAD1901 exhibited a complex biphasic pharmacology that manifests as antagonist activity at the higher doses.

Example 10

RAD1901 Exhibits Biphasic Activity with Respect to ESR1-Dependent Tumor Growth

As shown above, high dose RAD1901 (20 mg/kg) inhibited the growth of ESR1-dependent MCF7-cell derived tumors in mice. However, the observation that uterine wet weight was increased in mice treated with doses of RAD1901 that were lower than that required to effect ESR1 turnover highlighted the need to examine whether a similar biphasic pharmacology was manifest in breast tumors. To further evaluate the pharmacology of RAD1901, a second xenograft tumor study was conducted in which MCF7 tumors were established under estrogen stimulation. For FIG. 9A, MCF7 xenograft tumors were initiated in ovariectomized female nu/nu mice as in FIG. 5. Estrogen pellets were surgically removed when tumors reached ~0.1 cm$^3$ volume, and animals (n=6-10) then received daily treatment with vehicle or RAD1901 (RAD), (0.3-10 mg/kg sc). Mean tumor volume±SEM per day of treatment was presented. Significance as compared to the vehicle (2-way ANOVA of matched values followed by Bonferroni comparison) was indicated ($*p<0.05$, $**p<0.0005$). For FIG. 9B, uterine wet weight at sacrifice (measured as in FIG. 8) and % change in tumor volume (as compared to size at randomization) calculated using the final measurement recorded for mice in (FIG. 9A) are graphically presented. For FIGS. 9C-9D, expression of ESR1 target genes in tumors was analyzed essentially as in FIG. 5. Estrogen only samples from FIG. 5D were included for comparison. For FIG. 9E, ESR1 levels in tumor tissues were analyzed as in FIG. 8 and were normalized to similarly detected Lamin-A. Significant downregulation (*p<0.05) was determined by ANOVA followed by Bonferroni comparison.

Figures 9A, 9B, 9C, 9D, 9E:
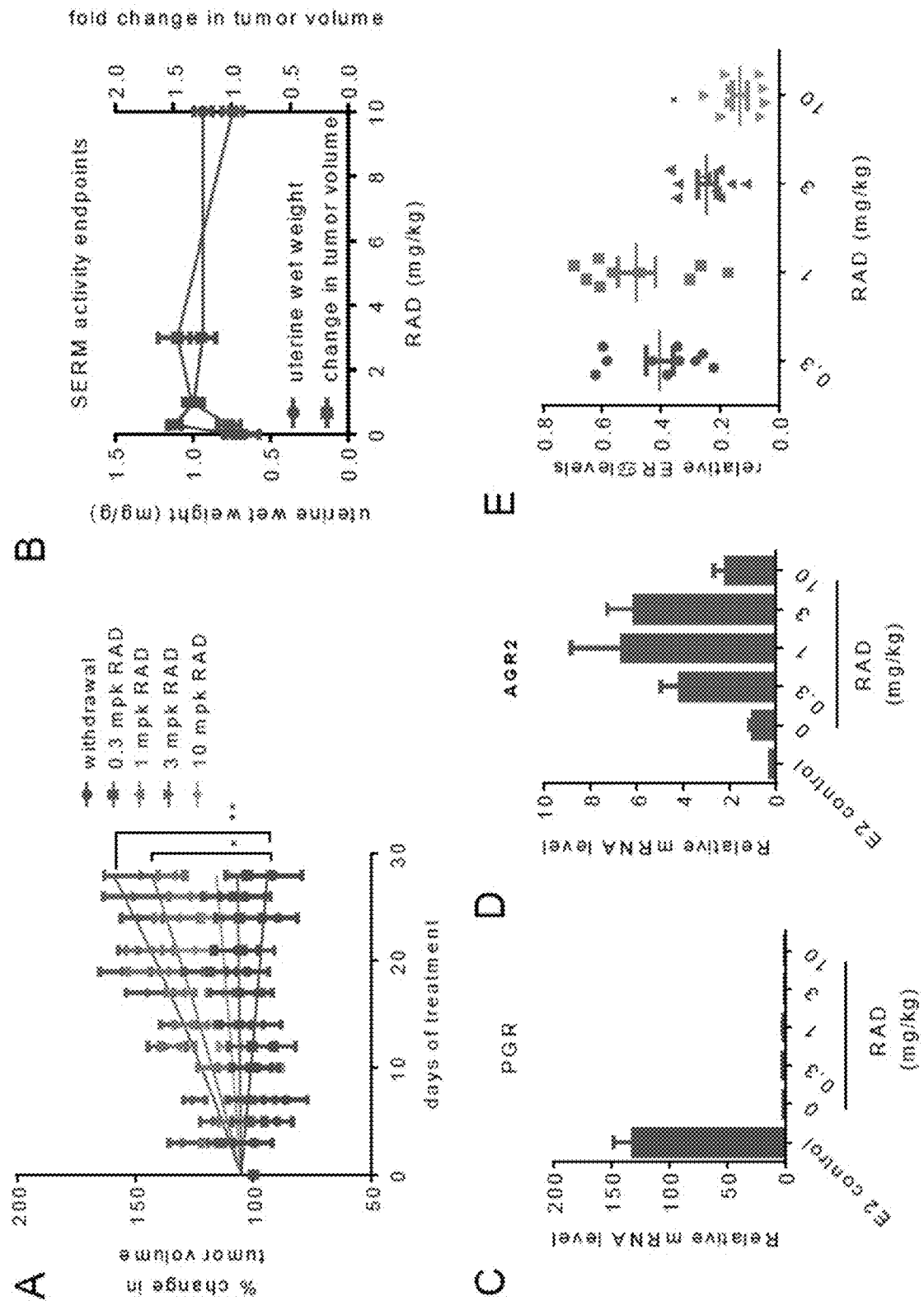
FIGS. 9A-9E show that RAD1901 exhibited dose dependent growth stimulation of MCF7 xenograft tumors.

When tumors reached ~0.1 cm$^3$ volume, estrogen was discontinued and animals were randomized to treatment with vehicle or RAD1901 (0.3, 1, 3, or 10 mg/kg). As observed in the uterine weight assay, RAD1901 exhibited a biphasic response, in that significant stimulation of tumor growth was observed in animals treated with 1 or 3 mg/kg RAD1901 that was not apparent at the higher dose (FIG. 9A). Although certainly less than that which was observed following E2 stimulation (FIG. 5E), the increased tumor volume in the 1 and 3 mg/kg groups was significant and of similar magnitude to that for partial ESR1 agonists. Interestingly, an evaluation of the final tumor size and uterine wet weight of these animals at sacrifice revealed that the pharmacology of RAD1901 was affected by both dose and tissue. Specifically, as reported above in a different strain of mice, stimulation of uterine weight was apparent in mice treated with only the 0.3 mg/kg dose of RAD1901, while tumor size was significantly increased in 1 or 3 mg/kg RAD1901 groups (FIG. 9B). Whereas the expression of classical ESR1 target genes such as PGR was not observed in the tumors in the 1 or 3 mg/kg treatment groups (FIG. 9C), the expression of AGR2 (FIG. 9D) and others SERM-regulated genes associated with tamoxifen resistance (not shown) was observed. Immunoblot analysis of tumor extracts revealed a dose-dependent downregulation of ESR1 by RAD1901 that reflected its actions as an inhibitor of tumor growth (FIG. 9E). Together these data highlight the complex pharmacology of RAD1901 and stress the importance of developing biomarkers that read on the partial agonist activity of the drug and which can be used for dose optimization in clinical studies.

Example 11

Elucidation of the Mechanisms that Distinguish RAD1901 from Other SERDs

Whether the dose-dependent agonist/antagonist activity of RAD1901 could be observed at the level of target gene regulation was determined. Specific sets of ESR1 target genes whose expression was differentially regulated by estrogens and SERMs and which could be used to distinguish between different SERMs and SERDs have been identified. A subset of these genes, those regulated by (a) agonists (with no or minimal response to SERMs), (b) SERMs (with no or little response to E2), or (c) either agonists or SERMs, were selected to profile RAD1901 activity.

Figures 10A, 10B, 10C:
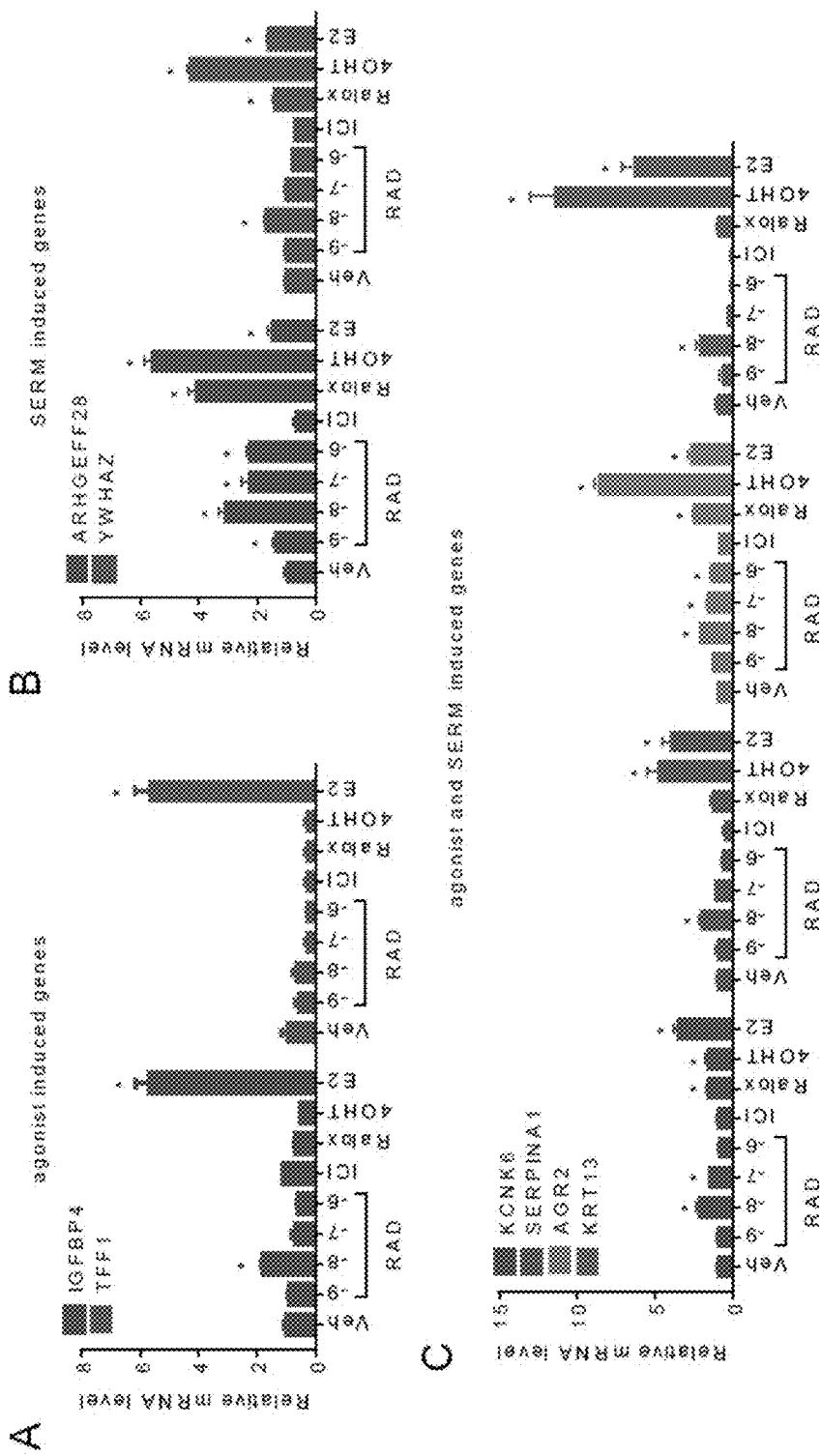
FIGS. 10A-10E show that RAD1901 exerted biphasic agonist/antagonist activity on ESR1 in a dose dependent manner.
Figures 10D, 10E:
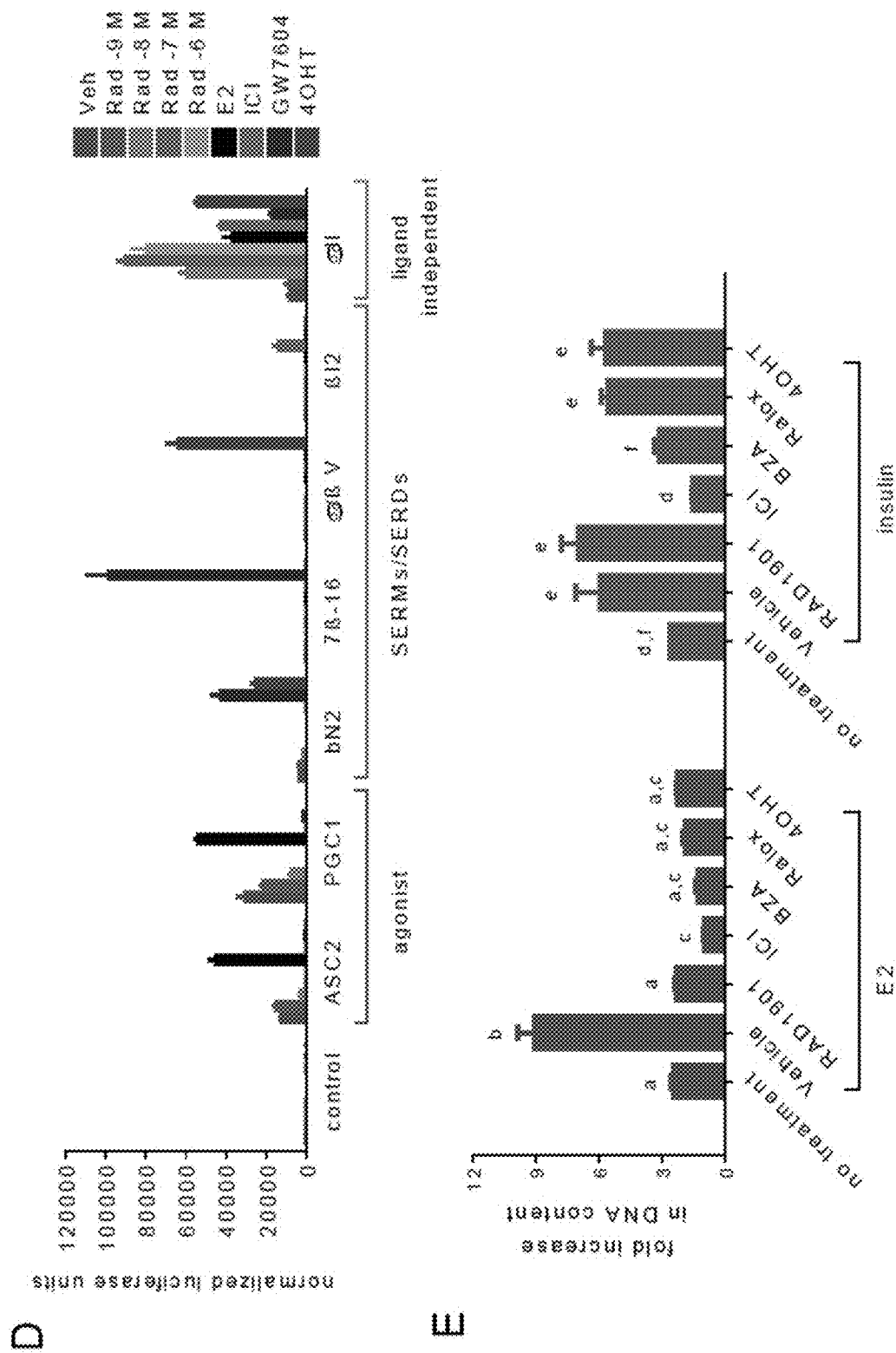
Figure 11:
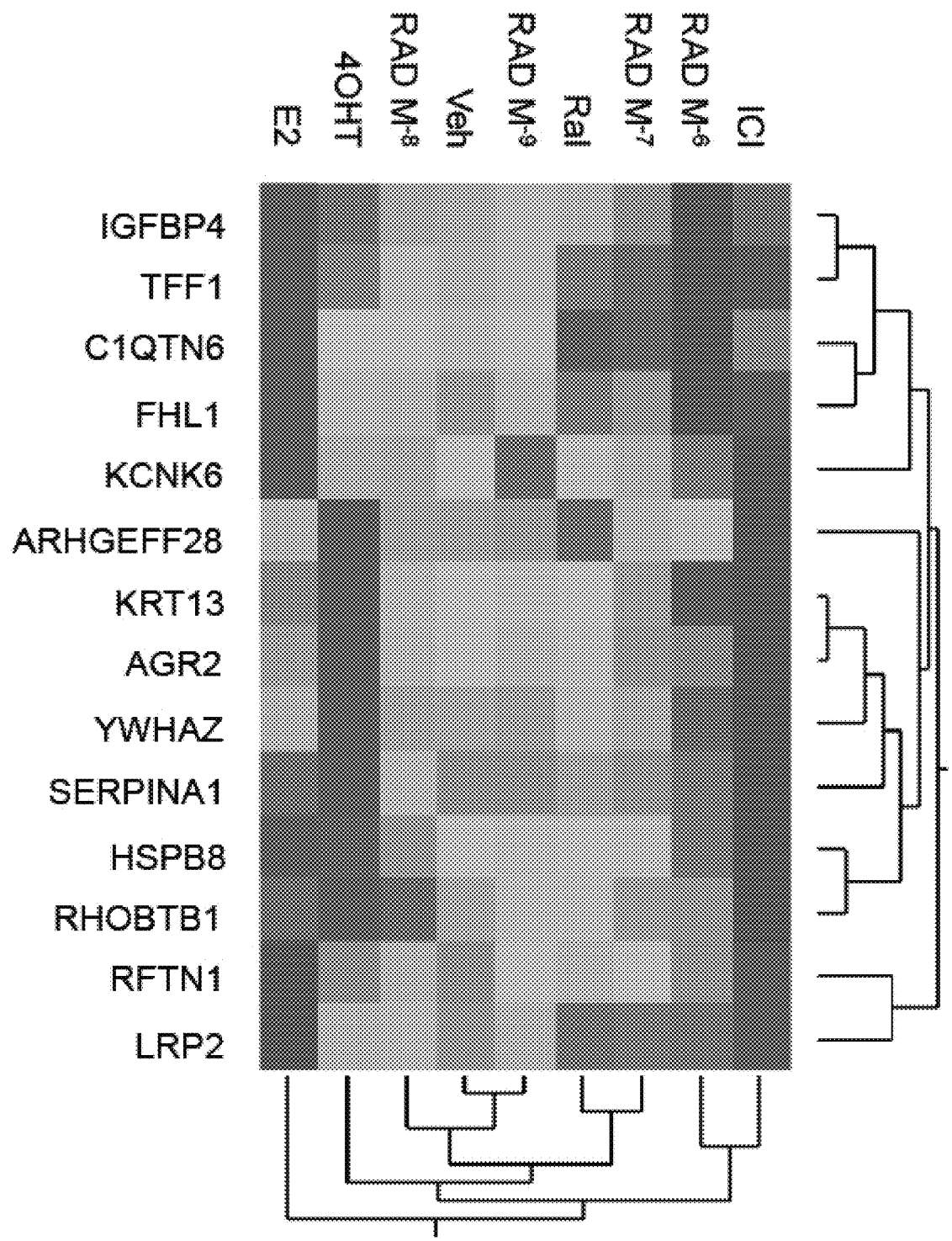
FIG. 11 shows the relative change in expression of ESR1 target genes and additional target genes responsive to agonists, primarily SERMs, or SERMs and agonists.

MCF7 cells were treated for 24 hours with $10^{-7}$ M vehicle (Veh), ICI, 4OHT, raloxifene (Ralox), E2 ($10^{-9}$ M) or RAD1901 ($10^{-9}$-$10^{-6}$ M). The expression of ESR1 target genes responsive to (FIG. 10A) agonists, (FIG. 10B) primarily SERMs, or (FIG. 10C) SERMs and agonists was analyzed as in FIG. 5. Relative changes of these and additional target genes designed to evaluate dose dependent response to RAD1901 are presented in FIG. 11. Significant target gene regulation (*p<0.05) as compared to the vehicle control was detected by 2-way ANOVA followed by Fisher's LSD (Graphpad Prism 6). FIG. 10D shows the interaction between ESR1 and conformation-specific peptides in a mammalian two-hybrid system. Triplicate wells of SKBR3 cells were transfected with plasmids expressing ESR1 fused to VP16 together with Gal4DBD alone (control) or Gal4DBD fused to ESR1 interacting peptides noted on the horizontal axis. Cells were then treated with the indicated ESR1 ligands ($10^{-7}$ M unless otherwise indicated). Interaction of ESR1 with the Gal4DBD peptide constructs was detected through activation of a Gal4-responsive luciferase reporter construct and was normalized to detected β-galactosidase activity expressed in a constitutive manner using a second vector. Normalized response was expressed as fold increase over the detected level of interaction between Gal4DBD alone and ESR1-VP16 in the absence of ligand (Veh). For FIG. 10E, the effect of SERMs and SERDs ($10^{-6}$ M) on the proliferation of MCF7 cells in response to E2 ($10^{-9}$ M) or insulin ($2 \times 10^{-9}$ M) was evaluated as in FIG. 5. Statistically similar treatments (2-way ANOVA followed by Bonferroni comparison) are indicated by letters. For FIG. 11, MCF7 cells were treated for 24 hours with $10^{-7}$ M vehicle (Veh), ICI, 4OHT, raloxifene (Ralox), E2 ($10^{-9}$ M) or RAD1901 ($10^{-9}$-$10^{-6}$ M). The expression of ESR1 target genes responsive to (A) agonists, (B) primarily SERMs, or (C) SERMs and agonists was analyzed using RT qPCR following RNA isolation. mRNA expression was normalized (ΔΔCT analysis) to the similarly detected 36B4 housekeeping. The profiles presented in dendogram format were analyzed with the Ward hierarchical clustering algorithm (JMP 11) using standardized data.

Reflecting the pharmacology observed in vivo, the expression pattern of these target genes exhibited a biphasic response to RAD1901 with agonist activity been observed at lower doses and more complete antagonist activity apparent at higher doses (FIGS. 10A-10C and FIG. 11). These data confirmed the unique pharmacology of RAD1901 and suggested that this drug may function by a mechanism that was distinct from other ESR1 downregulators.

The pharmacology of ESR1 ligands reflects their influence on the overall structure of the receptor and on the impact which this has on coregulator recruitment. Given the distinct pharmacology exhibited by RAD1901, it may enable ESR1 to adopt a unique conformation. A conformational profiling tool was used to interrogate the ESR1-RAD1901 complex. In this assay a modified two-hybrid assay was used to assess the binding of a series of short peptides that survey the protein-protein interaction surfaces on ESR1 that were presented when occupied by different ligands. As shown in FIG. 10D, the interaction profile observed in the presence of RAD1901 was completely distinct from any other known ligand. Notable was the ability of RAD1901 to disengage the classical coregulator-binding surface (AF2) as indicated by the decreased interaction with the peptides that report on "agonist activity" (ASC1 and PGC1). No interaction was observed with peptides that report on the ESR1 structures adopted upon binding tamoxifen (αβV) or ICI (βI2). There was significant interaction of all in the presence of RAD1901, a peptide that reports on a cryptic protein-protein interaction surface in the hinge region of the receptor. RAD1901 enabled ESR1 to assume a unique conformation that was distinct from that apparent upon binding agonists, the SERM tamoxifen, and other known SERDs (FIG. 10D).

In addition to classical agonists, ESR1 transcriptional activity can also be induced by treating cells with growth factors such as EGF, IGF1 or insulin. Whereas the mechanisms underlying this "ligand-independent" activity were likely to be complex, this alternate pathway of activation contributes to resistance to endocrine therapy in breast cancer. The comparative pharmacology of RAD1901 was evaluated for its ability to suppress growth factor dependent activation of ESR1. In this assay, it was determined that although all of the SERMs and SERDs tested inhibited E2-stimulated proliferation, only BZA and ICI efficiently inhibited insulin-stimulated proliferation, while 4OHT, Ralox, and RAD1901 were without effect (FIG. 10E). These results confirm the unique mechanism of action of RAD1901. RAD1901 may be delivered in combination with another drug that inhibits ligand-independent activation of ESR1 to achieve maximal clinical response.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method of treating estrogen receptor positive cancers of the brain in a subject, the method comprising administering a compound represented by the following formula I:

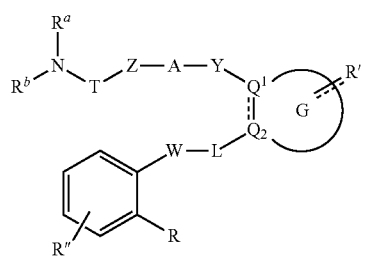

(I)

wherein
TZ represents a $C_1$-$C_4$ alkylene group or —$CR^fR^{g'}$—$CH_2$—O— wherein $R^f$ and $R^{g'}$ independently represent hydrogen or a $C_1$-$C_6$ alkyl group;
A represents a 5- to 14-membered heteroarylene group which may have a substituent or a $C_6$-$C_{14}$ arylene group which may have a substituent;
Y represents —$CH_2$—$NR^c$— wherein $R^c$ represents hydrogen or a $C_1$-$C_6$ alkyl group which may have a substituent;
ring G represents the following formula:

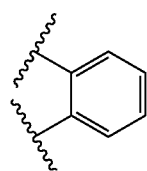

R' represents 1 to 4 substituents independently selected from a hydrogen atom, a $C_1$-$C_6$ alkoxy group, and a hydroxyl group;

a partial structure in formula (I) represented by the following formula:

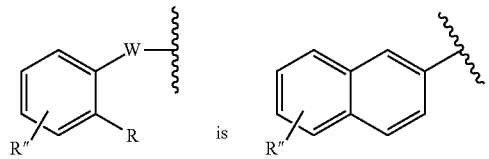

R" represents hydrogen, a hydroxyl group that may be further protected by a protecting group or a $C_1$-$C_6$ alkoxy group which may have a substituent; and
$R^a$ and $R^b$ are the same as or different from each other and each represents a hydrogen atom, a $C_1$-$C_6$ alkyl group which may have a substituent, or a $C_3$-$C_8$ cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and
L represents a single bond,
or a salt thereof.

Clause 2. The method of clause 1, wherein the cancer is Breast cancer brain metastases, Astrocytoma, Atypical Teratoid Rhabdoid Tumor (ATRT), Chondrosarcoma, Choroid Plexus Carcinoma, Craniopharyngioma, Ependymoma, Germ Cell Tumor, Glioblastoma, Glioma, Hemangioma, Juvenile Pilocytic Astrocytoma, Medulloblastoma, Meningioma, Neurofibroma, Neuronal and Mixed Neuronal-Glial Tumors, Oligoastrocytoma, Oligodendroglioma, Pineal Tumor, Pituitary Tumor, PNET—(primitive neuroectodermal tumor), Schwannoma, and Leptomeningeal metastases.

Clause 3. A method of treating breast cancer brain metastasis in a subject, the method comprising administering a compound represented by the following formula I:

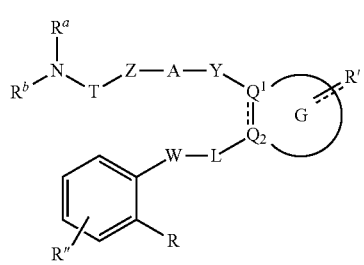

(I)

wherein
TZ represents a $C_1$-$C_4$ alkylene group or —$CR^fR^{g'}$—$CH_2$—O— wherein $R^f$ and $R^{g'}$ independently represent hydrogen or a $C_1$-$C_6$ alkyl group;
A represents a 5- to 14-membered heteroarylene group which may have a substituent or a $C_6$-$C_{14}$ arylene group which may have a substituent;
Y represents —$CH_2$—$NR^c$— wherein $R^c$ represents hydrogen or a $C_1$-$C_6$ alkyl group which may have a substituent;

ring G represents the following formula:

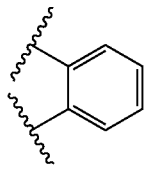 [SMILES: *c1ccccc1*]

R' represents 1 to 4 substituents independently selected from a hydrogen atom, a $C_1$-$C_6$ alkoxy group, and a hydroxyl group;
a partial structure in formula (I) represented by the following formula:

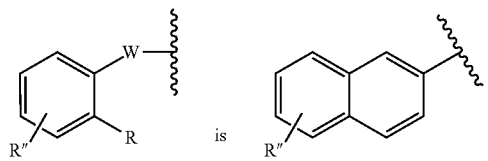

R" represents hydrogen, a hydroxyl group that may be further protected by a protecting group or a $C_1$-$C_6$ alkoxy group which may have a substituent; and
$R^a$ and $R^b$ are the same as or different from each other and each represents a hydrogen atom, a $C_1$-$C_6$ alkyl group which may have a substituent, or a $C_3$-$C_8$ cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and
L represents a single bond,
or a salt thereof.

Clause 4. A method of treating a cancer in a subject, wherein the cancer is resistant to an estrogen receptor modulator, the method comprising administering a compound represented by the following formula I:

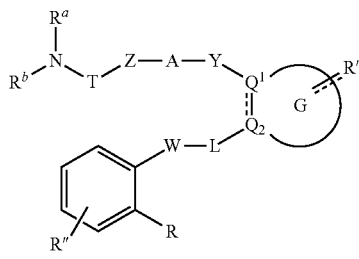

wherein
TZ represents a $C_1$-$C_4$ alkylene group or —$CR^fR^{g'}$—$CH_2$—O— wherein $R^{f'}$ and $R^{g'}$ independently represent hydrogen or a $C_1$-$C_6$ alkyl group;
A represents a 5- to 14-membered heteroarylene group which may have a substituent or a $C_6$-$C_{14}$ arylene group which may have a substituent;
Y represents —$CH_2$—$NR^c$— wherein $R^c$ represents hydrogen or a $C_1$-$C_6$ alkyl group which may have a substituent;

ring G represents the following formula:

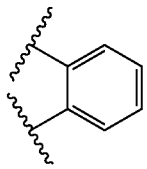

R' represents 1 to 4 substituents independently selected from a hydrogen atom, a $C_1$-$C_6$ alkoxy group, and a hydroxyl group;
a partial structure in formula (I) represented by the following formula:

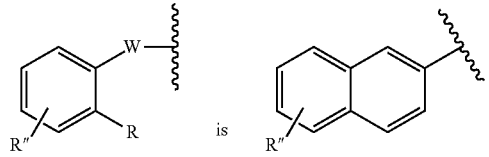

R" represents hydrogen, a hydroxyl group that may be further protected by a protecting group or a $C_1$-$C_6$ alkoxy group which may have a substituent; and
$R^a$ and $R^b$ are the same as or different from each other and each represents a hydrogen atom, a $C_1$-$C_6$ alkyl group which may have a substituent, or a $C_3$-$C_8$ cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and
L represents a single bond,
or a salt thereof.

Clause 5. The method of clause 4, wherein the cancer is de novo resistant to the estrogen receptor modulator.

Clause 6. The method of clause 4, wherein the resistance to the estrogen receptor modulator is acquired.

Clause 7. The method of clause 4, wherein the estrogen receptor modulator is a selective estrogen receptor modulator (SERM).

Clause 8. The method of clause 7, wherein the SERM is tamoxifen, idoxifene, raloxifene or ICI 182,780.

Clause 9. The method of any one of clauses 4-8, wherein the cancer is breast, endometrial or ovarian cancer.

Clause 10. The method of any one of clauses 4-9, wherein the cancer is breast cancer.

Clause 11. The method of any one of clauses 1-10, wherein $R^a$ and $R^b$ independently represent a hydrogen atom, a methyl group, an ethyl group, a n-propyl group, an iso-propyl group, a n-butyl group, an iso-butyl group, or a tert-butyl group.

Clause 12. The method of any one of clauses 1-10, wherein -T-Z— represents —$CH_2CH_2$— or —$C(CH_3)_2CH_2O$—.

Clause 13. The method of any one of clauses 1-10, wherein Y represents —$CH_2$—$N(CH_2CH_3)$— or —$CH_2$—$N(CH_2CH_2OH)$—.

Clause 14. The method of any one of clauses 1-10, wherein each of R" independently represents a hydrogen atom or a methoxy group.

Clause 15. The method of any one of clauses 1-10, wherein R" represents a hydroxyl group.

Clause 16. The method of any one of clauses 1-10, wherein A represents a phenylene group.

Clause 17. The method of any one of clauses 1-10, wherein the compound is (R)-6-{2-{ethyl[4-(2-ethylaminoethyl)benzyl]amino}-4-methoxyphenyl}-5,6,7,8-tetrahydronaphthalen-2-ol.

Clause 18. The method of any one of clauses 1-10, wherein an effective amount of the compound is administered.

Clause 19. The method of any one of clauses 1-10, wherein the effective amount comprises a high dosage.

Clause 20. The method of clause 19, wherein the high dosage is more than about 20 mg/kg.

Clause 21. The method of clause 19 or 20, wherein the high dosage is about 20 mg/kg to about 100 mg/kg.

Clause 22. The method of any one of clauses 1-10, wherein the compound is administered by oral administration, intravenous administration, intradermal injection, intramuscular injection, or subcutaneous injection.

Clause 23. The method of any one of clauses 1-10, further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

What is claimed is:

1. A method of treating an estrogen receptor positive breast cancer in a subject, wherein the estrogen receptor positive breast cancer is resistant to one or more aromatase inhibitors, the method comprising administering to a subject a compound, (R)-6-{2-{ethyl[4-(2-ethylaminoethyl)benzyl]amino}-4-methoxyphenyll-5,6,7,8-tetrahydronaphthalen-2-ol, which has the structure

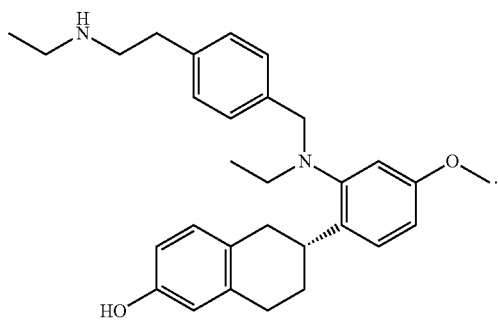 [SMILES: CCNCCc1ccc(CN(CC)c2cc(OC)ccc2[C@@H]2CCc3cc(O)ccc3C2)cc1]

2. The method of claim 1, wherein the compound is administered as part of a pharmaceutical composition.

3. The method of claim 2, wherein the composition is administered daily as a single dose.

4. The method of claim 2, wherein the composition is administered daily as a multi-dose.

5. The method of claim 1, wherein the one or more aromatase inhibitor(s) is selected from the group consisting of anastrozole, letrozole, exemestane, formestane, fadrozole, aminoglutethimide, testolactone, and combinations thereof.

6. The method of claim 5, wherein the one or more aromatase inhibitor(s) is selected from anastrozole, letrozole, exemestane, and combinations thereof.

7. The method of claim 1, wherein an effective amount of the compound is administered.

8. The method of claim 7, wherein the effective amount is from about 200 mg/day to about 500 mg/day.

9. The method of claim 8, wherein the effective amount is about 400 mg/day.

10. The method of claim 7, wherein the compound is administered by oral administration, intravenous administration, intradermal injection, intramuscular injection or subcutaneous injection.

11. The method of claim 10, wherein the compound is administered by oral administration.

12. The method of claim 1, further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARa or gamma agonist and a MAP kinase inhibitor.

13. The method of claim 12, wherein the at least one compound is a CDK4/6 inhibitor.

14. The method of claim 12, wherein the at least one compound is an antiestrogen.

\* \* \* \* \*